United States Patent
Shi et al.

(10) Patent No.: US 10,550,073 B2
(45) Date of Patent: Feb. 4, 2020

(54) BENZAMIDE DERIVATIVE

(71) Applicant: CSPC ZHONGQI PHARMACEUTICAL TECHNOLOGY (SHIJIAZHUANG) CO., LTD., Shijiazhuang, Hebei (CN)

(72) Inventors: Ying Shi, Hebei (CN); Yi Mi, Hebei (CN); Hanyu Yang, Hebei (CN); Xuliang Wang, Hebei (CN); Denghuang Gong, Hebei (CN); Min Bai, Hebei (CN); Xiaozhuo Chen, Hebei (CN); Yujie Chen, Hebei (CN); Xuejiao Zhang, Hebei (CN); Yuxiu Ma, Hebei (CN); Qingzhi Gao, Hebei (CN)

(73) Assignee: CSPC Zhongqi Pharmaceutical Technology (Shijiazhuang) Co., Ltd. (CN)

( * ) Notice: Subject to any disclaimer, the term of this patent is extended or adjusted under 35 U.S.C. 154(b) by 0 days.

(21) Appl. No.: 15/763,807

(22) PCT Filed: Sep. 30, 2016

(86) PCT No.: PCT/CN2016/101038
§ 371 (c)(1),
(2) Date: Mar. 27, 2018

(87) PCT Pub. No.: WO2017/054765
PCT Pub. Date: Apr. 6, 2017

(65) Prior Publication Data
US 2018/0312462 A1 Nov. 1, 2018

(30) Foreign Application Priority Data

Sep. 30, 2015 (CN) .......................... 2015 1 0638788
Jun. 3, 2016 (CN) .......................... 2016 1 0390661

(51) Int. Cl.
| | | |
|---|---|---|
| C07C 235/84 | (2006.01) |
| C07D 403/12 | (2006.01) |
| C07D 237/24 | (2006.01) |
| C07C 231/12 | (2006.01) |
| C07C 237/38 | (2006.01) |
| C07C 237/42 | (2006.01) |
| C07C 273/18 | (2006.01) |
| C07C 275/38 | (2006.01) |
| C07D 211/16 | (2006.01) |
| C07D 211/46 | (2006.01) |
| C07D 213/81 | (2006.01) |
| C07D 213/82 | (2006.01) |
| C07D 277/82 | (2006.01) |
| C07D 295/192 | (2006.01) |

(Continued)

(52) U.S. Cl.
CPC .......... *C07C 235/84* (2013.01); *C07C 231/12* (2013.01); *C07C 237/38* (2013.01); *C07C 237/42* (2013.01); *C07C 273/1854* (2013.01); *C07C 275/38* (2013.01); *C07D 211/16* (2013.01); *C07D 211/46* (2013.01); *C07D 213/81* (2013.01); *C07D 213/82* (2013.01); *C07D 237/24* (2013.01); *C07D 277/82* (2013.01); *C07D 295/192* (2013.01); *C07D 333/38* (2013.01); *C07D 401/06* (2013.01); *C07D 401/12* (2013.01); *C07D 403/12* (2013.01); *C07D 409/06* (2013.01); *C07C 2601/02* (2017.05); *C07C 2601/08* (2017.05); *C07C 2601/14* (2017.05)

(58) Field of Classification Search
CPC ............ C07C 235/84; C07C 273/1854; C07C 2601/08; C07C 231/12; C07C 237/38; C07C 237/42; C07C 275/38; C07C 2601/14; C07C 2601/02; C07C 233/65; C07C 235/60; C07C 275/42; C07D 333/38; C07D 401/12; C07D 295/192; C07D 277/82; C07D 213/82; C07D 409/06; C07D 213/81; C07D 211/16; C07D 211/46; C07D 401/06; C07D 403/12; C07D 237/24; A61K 31/50; A61K 31/44
See application file for complete search history.

(56) References Cited

FOREIGN PATENT DOCUMENTS

| WO | WO-03068747 A1 * | 8/2003 | ........... C07D 213/82 |
|---|---|---|---|
| WO | WO 2004/089874 A1 | 10/2004 | |
| WO | WO 2004/089876 A1 | 10/2004 | |

OTHER PUBLICATIONS

Norman, P., "Investigational p38 inhibitors for the treatment of chronic obstructive pulmonary disease." Expert opinion on investigational drugs 24.3 (2015): 383-392.*

(Continued)

*Primary Examiner* — John M Mauro
(74) *Attorney, Agent, or Firm* — Lewis Roca Rothgerber Christie LLP

(57) ABSTRACT

The present invention relates to a benzamide derivative of general formula I, a drug composition containing same and a use thereof as a drug, wherein the definitions of $R_1$, Z and Q are as described in the description.

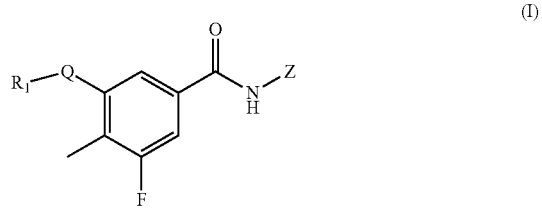

(I)

22 Claims, No Drawings

(51) Int. Cl.
*C07D 333/38* (2006.01)
*C07D 401/12* (2006.01)
*C07D 409/06* (2006.01)
*C07D 401/06* (2006.01)

(56) References Cited

OTHER PUBLICATIONS

Aston, N. M., "p38α mitogen-activated protein kinase inhibitors: optimization of a series of biphenylamides to give a molecule suitable for clinical progression." Journal of medicinal chemistry 52.20 (2009): 6257-6269; Supporting Information p. S1-S4.*
Aston, et al., "p38r Mitogen-Activated Protein Kinase Inhibitors: Optimization of a Series of Biphenylamides to Give a Molecule Suitable for Clinical Progression," J. Med. Chem., vol. 52, No. 20, Sep. 22, 2009, pp. 6257-6269.

* cited by examiner

BENZAMIDE DERIVATIVE

CROSS-REFERENCE TO RELATED APPLICATION(S)

This application is a National Phase Patent Application and claims priority to and the benefit of International Application Number PCT/CN2016/101038, filed on Sep. 30, 2016, which claims priority to Chinese Patent Application Number 201510638788.3, filed on Sep. 30, 2015, and Chinese Patent Application Number 201610390661.9, filed on Jun. 3, 2016, the entire contents of all of which are incorporated herein by reference.

TECHNICAL FIELD

The present invention belongs to the technical field of medicine and relates to a new benzamide derivative, a pharmaceutical composition containing the same, a preparation method thereof and a use thereof as a drug.

BACKGROUND ART

Mitogen-activated protein kinase (MAPK), which belongs to serine/threonine kinases, is an important molecule which can receive signals delivered by a receptor and bring the signals into the cell nucleus, has an important mechanism for participating in the regulation of gene expression, cell proliferation and death, and plays a key role in many receptor signaling pathways. P38 kinase, an important member in the mitogen-activated protein kinase (MAPK) family, is considered as an important part of the cell factor-mediated immune response mechanism, the p38 kinase not only plays an important role in inflammatory and stress reaction but also participates in the processes of cell survival, differentiation and apoptosis, therefore, it is considered as an important protein in numerous cell signaling pathways. It is known that p38 kinase can phosphorylate some intracellular proteins, which involve in the cascade of the enzymatic step and can result in the biological synthesis and release of cytokines (such as TNF-α and IL-1). Research finds that p38 kinase has an obvious regulation effect on the occurrence of many diseases, and particularly plays a core role in the regulation of inflammatory response diseases. The inflammatory response is essentially an important component of human autoimmune system, if an exception occurs, a series of serious diseases, such as rheumatoid arthritis, chronic lung obstruction, cardiovascular disease, gout, psoriasis, asthma, tumor, diabetes mellitus, arteriosclerosis, Crohn's disease and the like will be caused.

It is well known that cytokines are produced by a variety of cells (such as single cell and macrophages), which can result in a number of physiological effects, these physiological effects are considered to be very important in diseases (such as inflammation and immunoregulation). Cytokines are also considered to affect the generation and the development of diseases.

Tumor necrosis factor-α (TNF-α) and interleukin-1 (IL-1) are two important proinflammatory cytokines, they are considered as the main medium for activating the cell cascade reactions and play a leading role in the systemic inflammatory response, which is described in Charles A. Dinarello et al., *inflammatory cytokines: interleukin-1 and tumor necrosis factor as effect or molecules in autoimmune diseases*, Current Opinion in Immunology, 1991, 3(6), 941-948. Research shows that when a specific inhibitor acts on the p38 kinase, the expression quantity of the proinflammatory cytokines such as TNF-α and the like is remarkably reduced, this indicates that the over-expression of TNF-α and the like in inflammatory reactions is closely related to the activity of p38 kinase. P38 kinase participates in the inflammatory reaction process by controlling and modulating the synthesis and the release process of proinflammatory cytokines such as tumor necrosis factor-α (TNF-α), interleukin-1β (IL-1β) and anti-inflammatory factors such as interleukin-10 and the like. Therefore, cytokines (such as TNF-α and IL-1) are considered to participate in mediating many diseases, and it is expected that the inhibition on the generation and/or the effect of these cytokines may help prevent, control or treat these diseases.

Non-steroidal anti-inflammatory drugs (NSAIDs) are the most common anti-inflammatory drugs, however, many individuals cannot tolerate the dosage required by long-time treatment of the diseases, the use of such drugs often cause serious toxic and side effects, such as the damage of gastrointestinal tract, kidney and liver, and sometimes may induce cardiovascular adverse events. In the biological treatment field of anti-inflammatory cytokines, great successes have been achieved in the use of the biological agents such as Etanercept, Infliximab, Adalimumab, Anakinra and the like for treating inflammatory patients, to whom the non-steroidal anti-inflammatory drugs are ineffective or inconvenient. However, as macromolecular drugs, the biological agents have many defects such as relatively long research period, being difficult to industrialize, relatively high production cost, and being inconvenient to use as an injection preparation and the like, therefore, there is a need for new oral anti-inflammatory drugs which are convenient to use and have good curative effect in the field of anti-inflammatory therapy. Since p38 kinase is considered to be a key anti-inflammatory target, it regulates TNF, IL-1 and other inflammatory factors and plays an important biological role in regulating the inflammatory response, as a small chemical molecule substance, the p38 kinase inhibitor has the potential to be developed into a novel small molecular drug for treating inflammatory diseases. However, poor oral bioavailability and high toxicity have been the main problem in preventing these compounds from becoming drugs.

SUMMARY OF THE INVENTION

In one aspect, the present invention provides a compound of formula I, or a tautomer, an optical isomer and a pharmaceutically acceptable salt thereof:

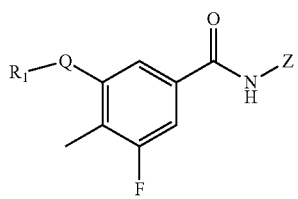

wherein:
Q is selected from the group consisting of

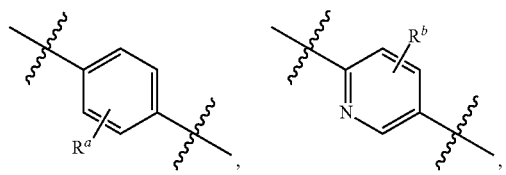

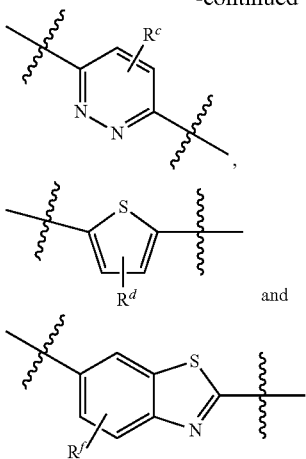

$R^{a-f}$ is independently selected from the group consisting of H, halogen, hydroxyl, amino, $C_{1-6}$alkyl and $C_{1-6}$alkoxy, wherein the alkyl and the alkoxy may be optionally substituted by one or more substituents selected from the group consisting of halogen, hydroxyl and amino, the amino may be optionally substituted by one or two $C_{1-6}$alkyl;

$R_1$ is:

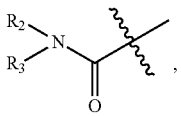

(1)

$R_2$ and $R_3$ are independently selected from the group consisting of H, $C_{1-6}$alkyl, $(CH_2)_{0-3}$-3~7-membered (such as $(CH_2)_{0-3}$-5~7-membered)cycloalkyl and heterocycloalkyl containing 1 or 2 heteroatoms, and $R_2$ and $R_3$ are not hydrogen at the same time; wherein the $C_{1-6}$alkyl may be optionally substituted by one or more substituents selected from the group consisting of halogen, hydroxyl, amino, cyano, $C_{1-6}$alkoxy, $(C_{0-6}$ alkyl) $(C_{0-6}$ alkyl) amino, $(C_{0-6}$ alkyl) thio, $(C_{1-6}$ alkyl)carbonyl and $(C_{1-6}$ alkyl) sulfonyl; the 3~7-membered (such as 5~7-membered)cycloalkyl or heterocycloalkyl is substituted by one $R'''$, wherein the $R'''$ is selected from the group consisting of hydrogen, $C_{1-6}$alkyl, hydroxyl, halogen and amino, the heteroatom of the heterocycloalkyl is selected from O, N, and S; or $R_2$ and $R_3$, together with the atoms attached thereto, form a 5, 6 or 7-membered ring, wherein, the 5, 6 or 7-membered ring is substituted by one $R''$, wherein the $R''$ is selected from hydrogen, $C_{1-6}$alkyl, hydroxyl, halogen and amino;

the 5, 6 or 7-membered ring, in addition to the N atom attaching to $R_2$ and $R_3$d, further contains 0, 1 or 2 heteroatoms selected from O, N, and S;

(2)

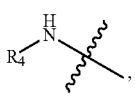

$R_4$ is selected from the group consisting of $C_{1-6}$alkyl, —$(CH_2)_{0-1}$-5~7-membered cycloalkyl, —$CO(CH_2)_{0-1}$—$R_5$ and —CONH—$R_6$.

$R_5$ and $R_6$ are independently selected from $C_{1-6}$alkyl and —$(CH_2)_{0-1}$-5~7-membered cycloalkyl;

Z is —$(CH_2)_{0-3}$—Y; Y is selected from the group consisting of 3~7-membered cycloalkyl, heterocycloalkyl containing 1 or 2 heteroatoms, hydroxyl. $C_{1-6}$alkoxy, halogen, amino, cyano, nitro, alkenyl and alkynyl; wherein, the cycloalkyl, heterocycloalkyl, amino, alkenyl and alkynyl are optionally substituted by the substituents selected from the group consisting of $C_{1-6}$alkyl, $C_{1-6}$alkoxy, halogen, hydroxyl, amino, cyano and nitro; the heteroatom of the heterocycloalkyl is selected from N, S and O;

with the proviso that the compound of formula I does not contain the following compounds:

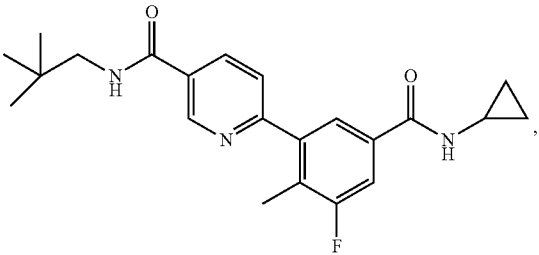

-continued
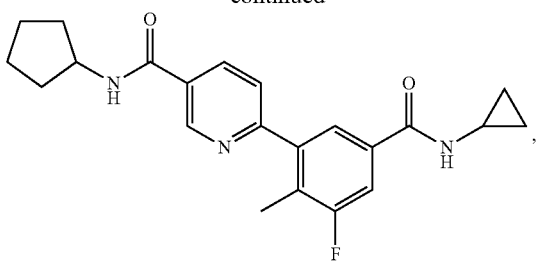
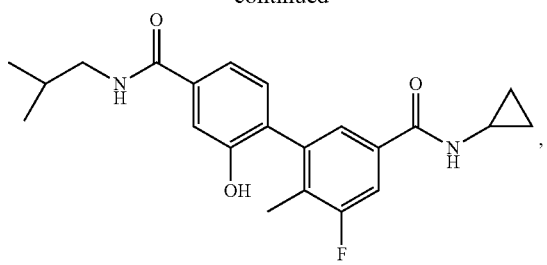
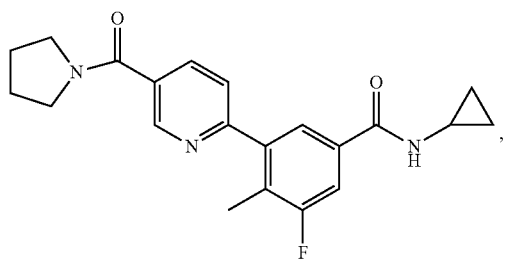
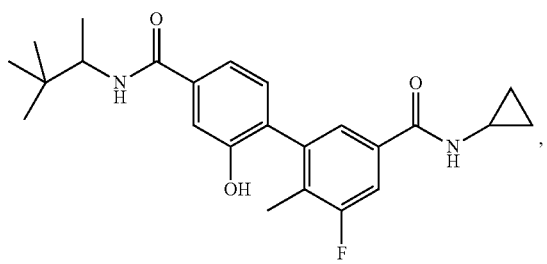
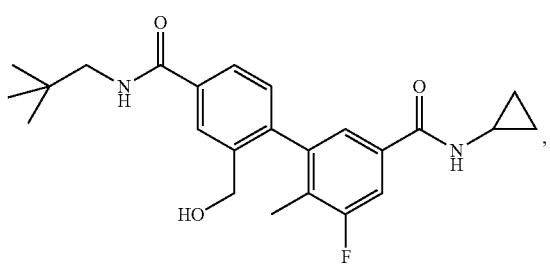
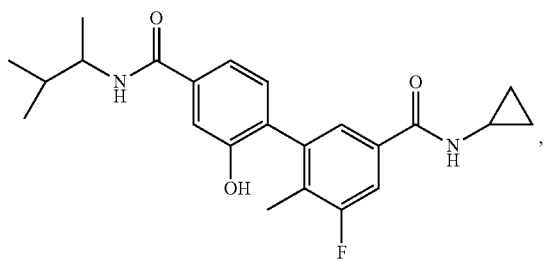
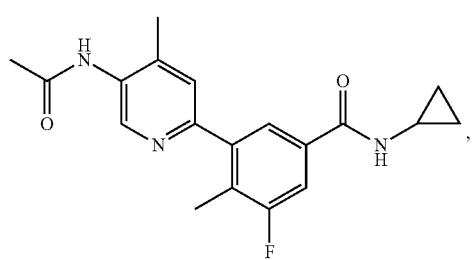
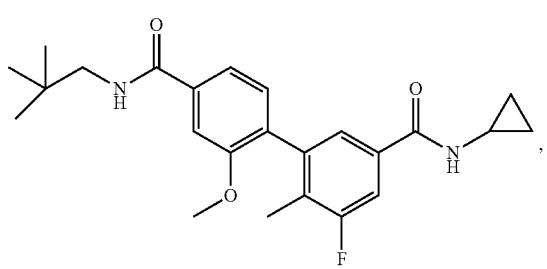
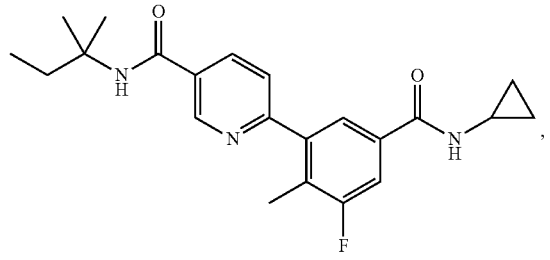
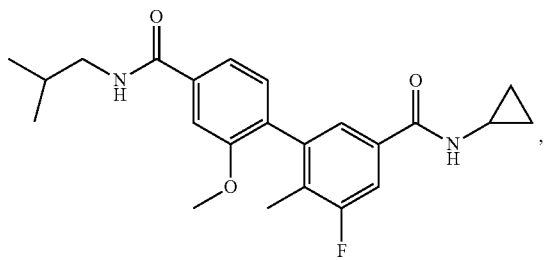
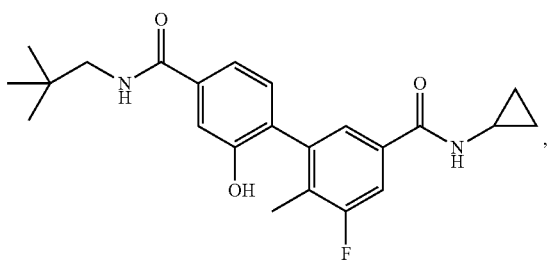

7
-continued
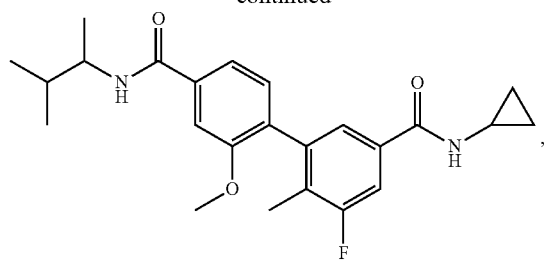
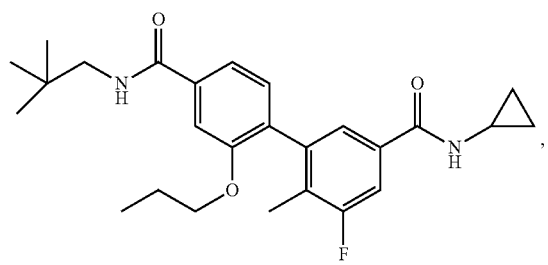
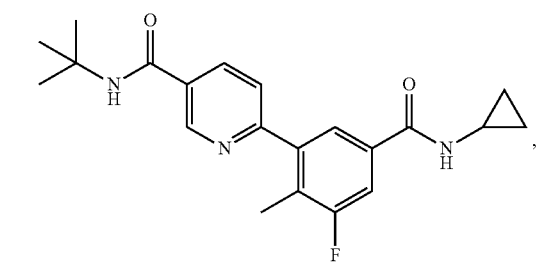
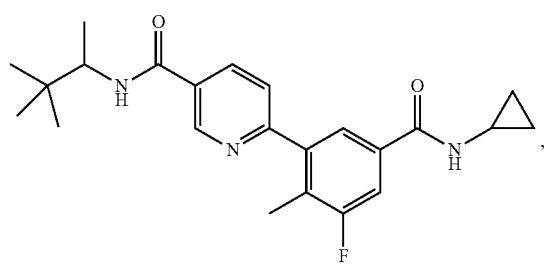
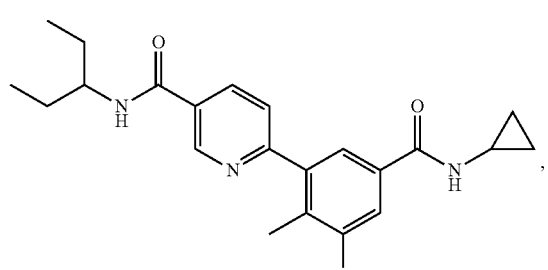
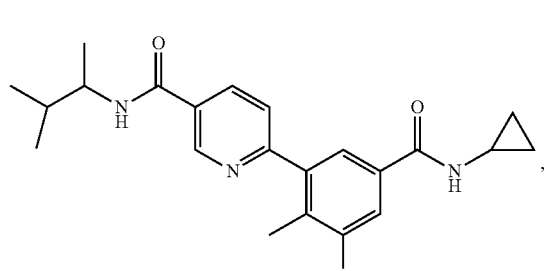
8
-continued
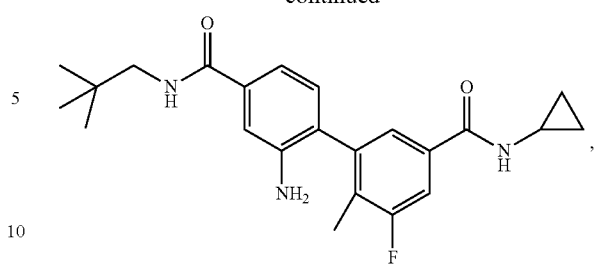
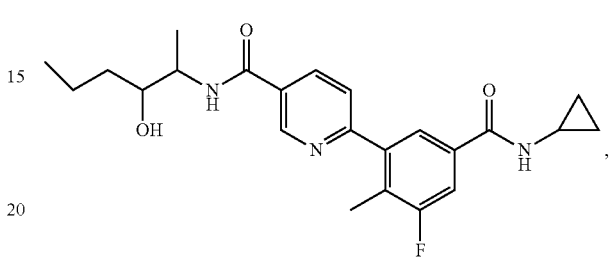
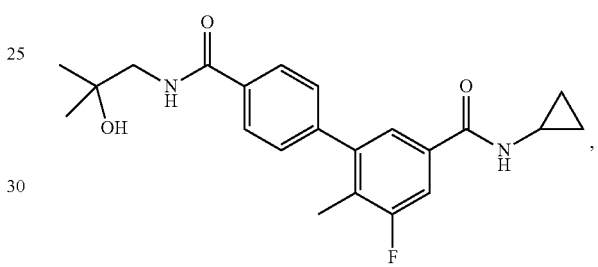
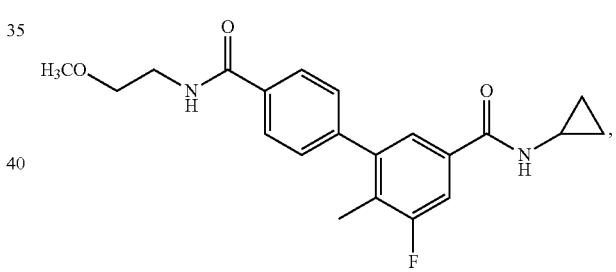
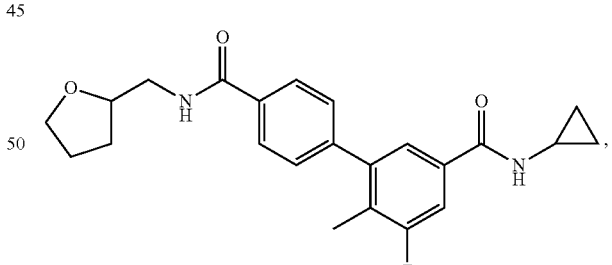
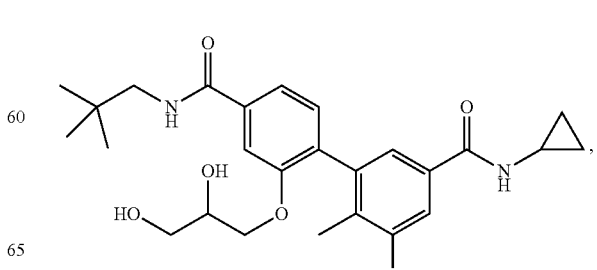

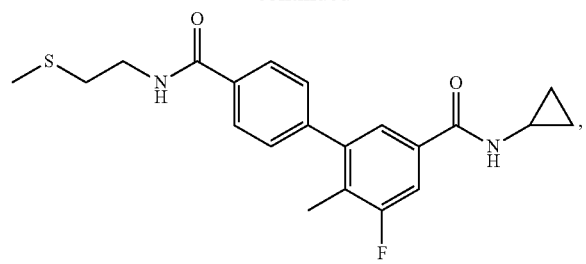
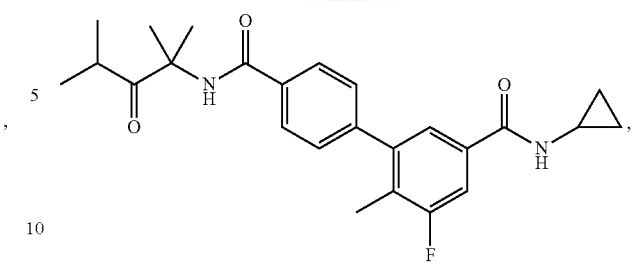
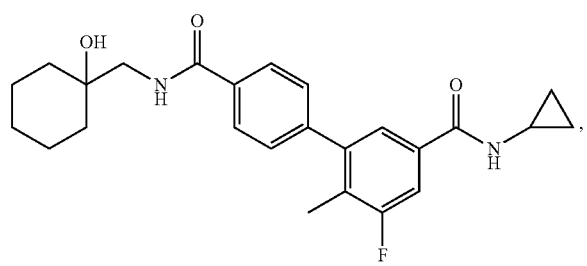
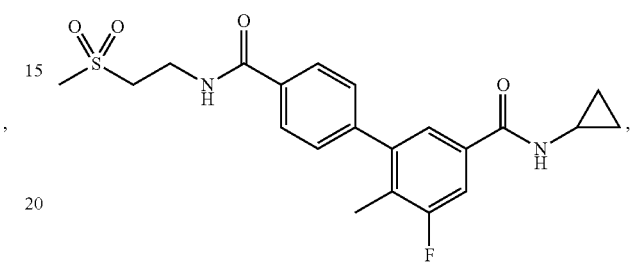
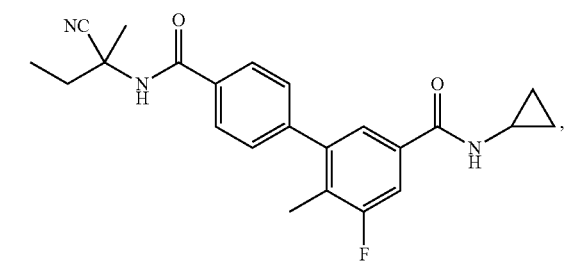
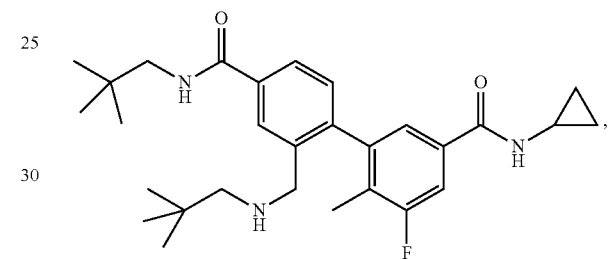
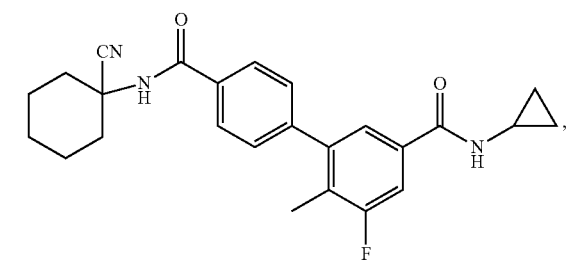
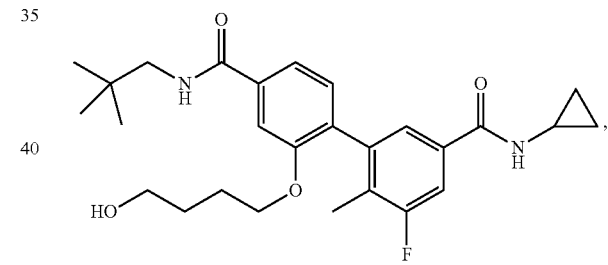
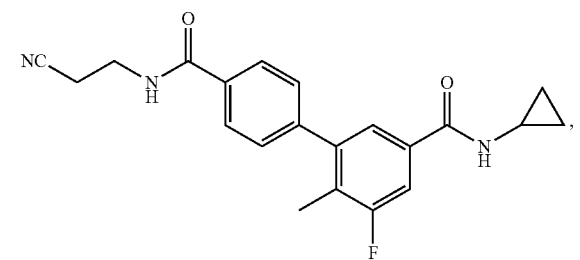
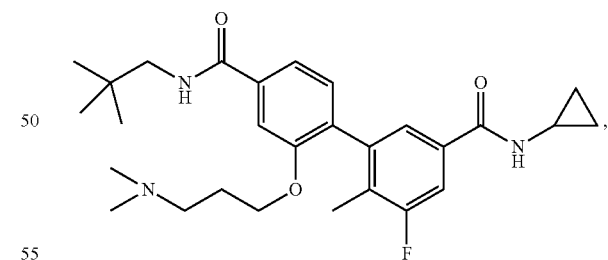
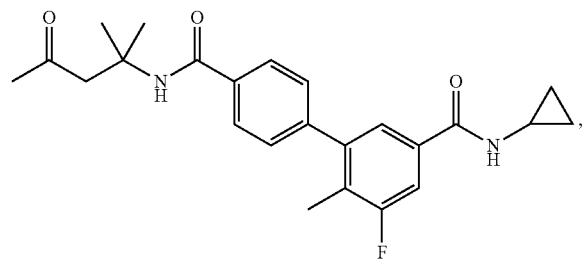
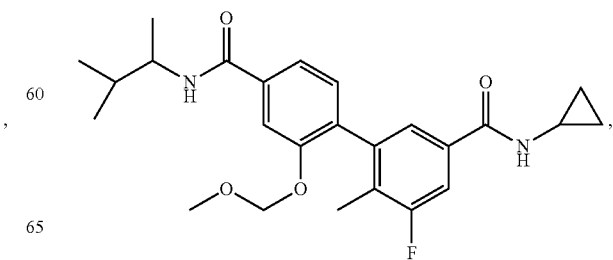

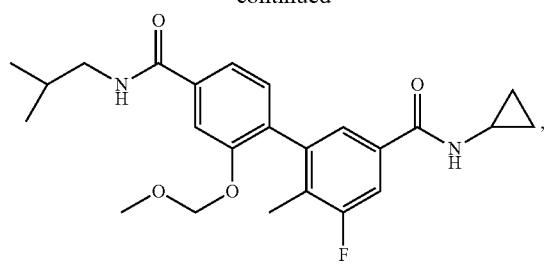
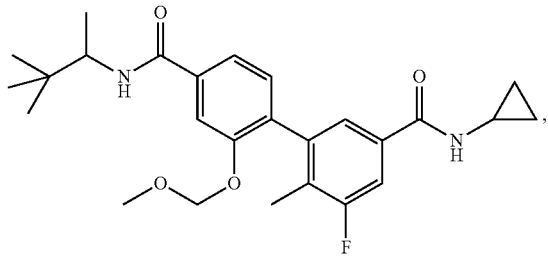
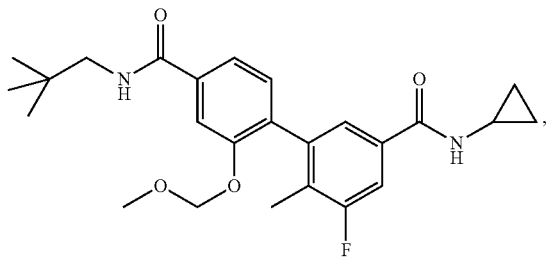
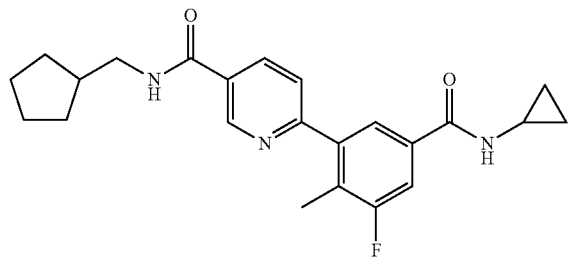
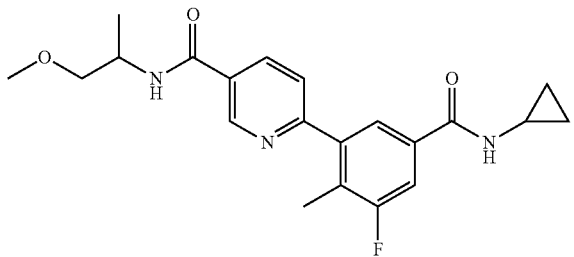
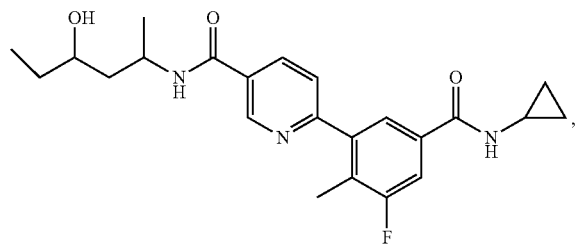
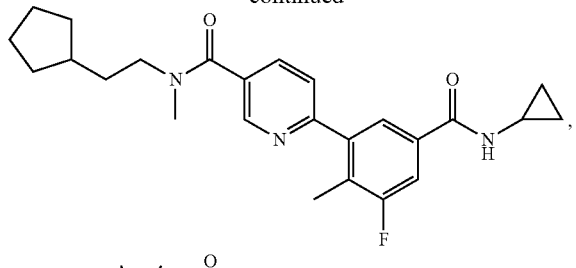
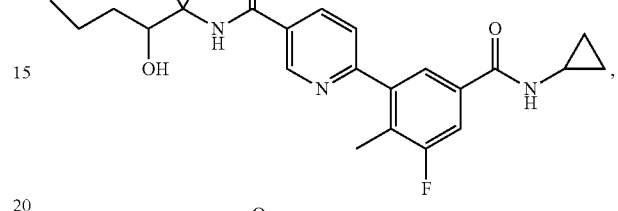
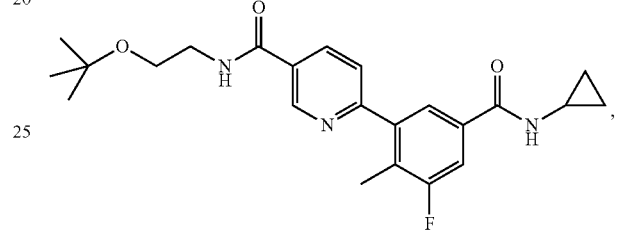
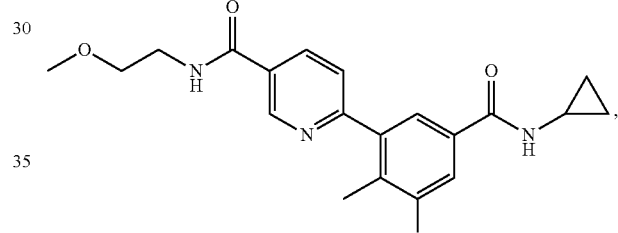
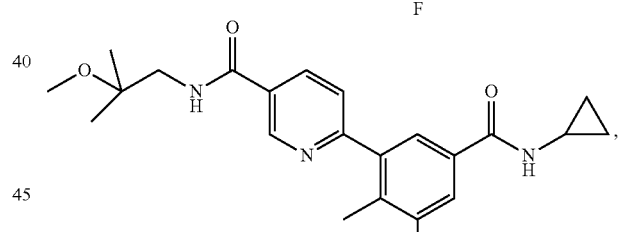
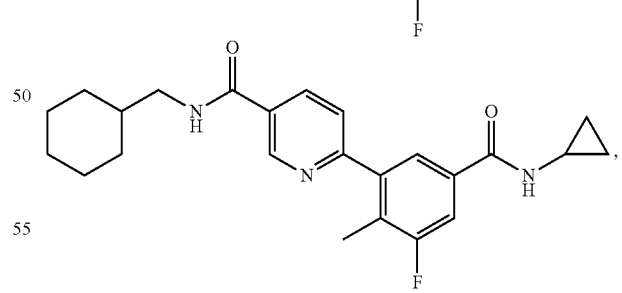
6-{5-[(cyclopropylamino)carbonyl]-3-fluoro-2-methylphenyl}-N-(1-methylbutyl) nicotinamide,
6-{5-[(cyclopropylamino)carbonyl]-3-fluoro-2-methylphenyl}-N-isobutyl-N-methyl nicotinamide,
6-{5-[(cyclopropylamino)carbonyl]-3-fluoro-2-methylphenyl}-N-(1,3-dimethylbutyl) nicotinamide,
N-cyclopentyl-6-{5-[(cyclopropylamino)carbonyl]-3-fluoro-2-methylphenyl}-N-methyl nicotinamide, 6-{5-[(cyclopropylamino)carbonyl]-3-fluoro-2-methylphenyl}-N-(3,3-dimethylbutyl) nicotinamide,
6-{5-[(cyclopropylamino)carbonyl]-3-fluoro-2-methylphenyl}-N-ethyl-N-isopropyl nicotinamide,
6-{5-[(cyclopropylamino)carbonyl]-3-fluoro-2-methylphenyl}-N-(tertpentyl) nicotinamide,
6-{5-[(cyclopropylamino)carbonyl]-3-fluoro-2-methylphenyl}-N-(3,3,3-trifluoropropyl) nicotinamide,
6-{5-[(cyclopropylamino)carbonyl]-3-fluoro-2-methylphenyl}-N-(1,1-dimethyl butyl) nicotinamide,
N-cyclohexyl-6-{5-[(cyclopropylamino)carbonyl]-3-fluoro-2-methylphenyl}-N-ethyl nicotinamide,
6-{5-[(cyclopropylamino)carbonyl]-3-fluoro-2-methylphenyl}-N-methyl-N-(1-methylcyclopentyl) nicotinamide,
6-{5-[(cyclopropylamino)carbonyl]-3-fluoro-2-methylphenyl}-N-isopropyl-N-methyl nicotinamide,
6-{5-[(cyclopropylamino)carbonyl]-3-fluoro-2-methylphenyl}-N-(3,3,3-trifluoro-2-methylpropyl) nicotinamide,
6-{5-[(cyclopropylamino)carbonyl]-3-fluoro-2-methylphenyl}-N-(1-ethyl-1-methylpropyl) nicotinamide,
6-{5-[(cyclopropylamino)carbonyl]-3-fluoro-2-methylphenyl}-N-ethyl nicotinamide,
N-cyclopropyl-3-fluoro-4-methyl-5-{5-[(4-methylpiperidin-1-yl)carbonyl]pyridine-2-yl) benzamide
N-cyclopropyl-3-{5-[(2-ethylpiperidin-1-yl)carbonyl]pyridine-2-yl}-5-fluoro-4-methyl benzamide,
N-cyclopropyl-3-{5-[(2-ethyl-2-methylpiperidin-1-yl)carbonyl]pyridine-2-yl}-5-fluoro-4-methyl benzamide,
N-cyclopropyl-3-fluoro-4-methyl-5-{5-[(2-propylpiperidin-1-yl)carbonyl]pyridine-2-yl}benzamide,
N-cyclopropyl-3-{5-[(2,4-dimethylpiperidin-1-yl)carbonyl]pyridine-2-yl}-5-fluoro-4-methyl benzamide,
N-cyclopropyl-3-{5-[(2,3-dimethylpiperidin-1-yl)carbonyl]pyridine-2-yl}-5-fluoro-4-methyl benzamide,
N-cyclopropyl-3-fluoro-4-methyl-5-{5-[(2,2,3-trimethylpyrrolidine-1-yl)carbonyl]pyridine-2-yl}benzamide,
N-cyclopropyl-3-{5-[(3-ethylpiperidin-1-yl)carbonyl]pyridine-2-yl}-5-fluoro-4-methyl benzamide,
N-cyclopropyl-3-fluoro-4-methyl-5-{5-[(2-methylpiperidin-1-yl)carbonyl]pyridine-2-yl}benzamide,
N-cyclopropyl-3-{5-[(3,3-dimethylpiperidin-1-yl)carbonyl]pyridine-2-yl}-5-fluoro-4-methyl benzamide,
N-cyclopropyl-3-fluoro-4-methyl-5-{5-[(3-methylpiperidin-1-yl)carbonyl]pyridine-2-yl}benzamide.

Preferably, $R^{a-f}$ is independently selected from the group consisting of H, F, hydroxyl, amino, methyl and methoxyl.

More preferably, $R^{a-f}$ is independently selected from the group consisting of H, amino, F and methyl.

Preferably, Q is selected from the group consisting of:

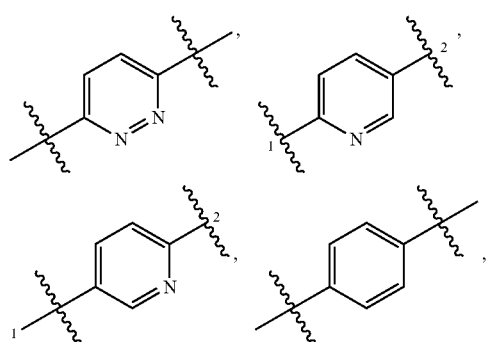

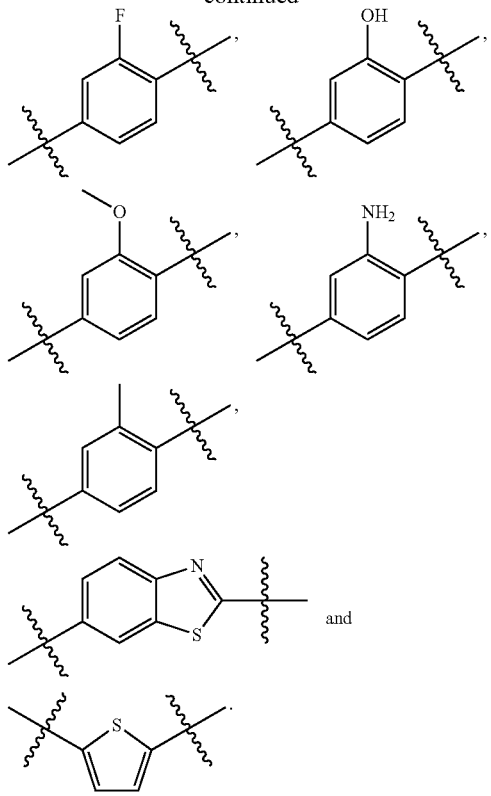

More preferably, Q is selected from the group consisting of:

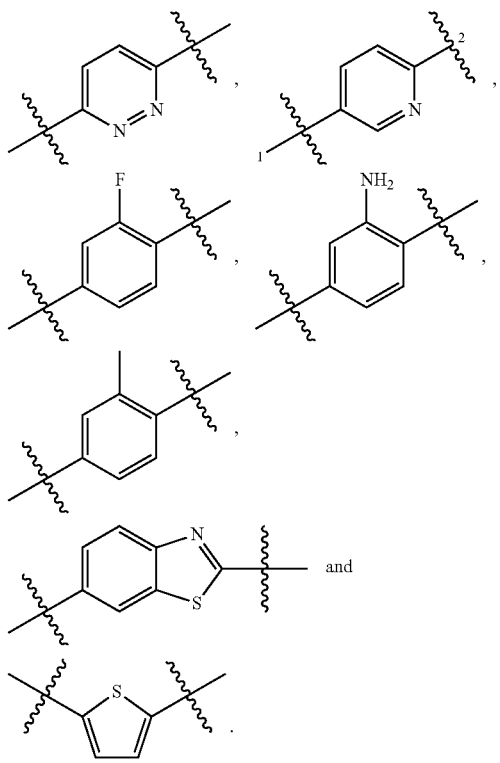

Further preferably, Q is selected from the group consisting of:

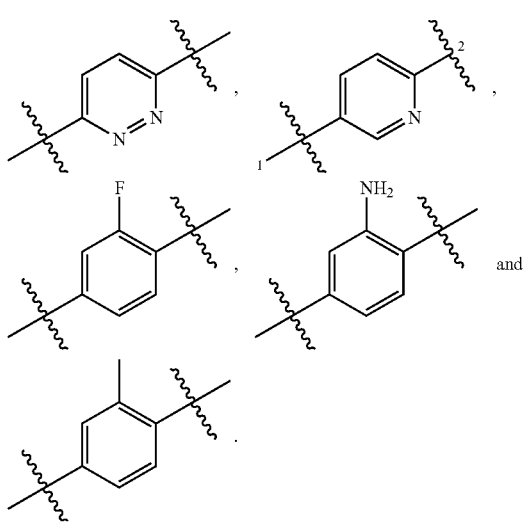

Further preferably, Q is selected from:

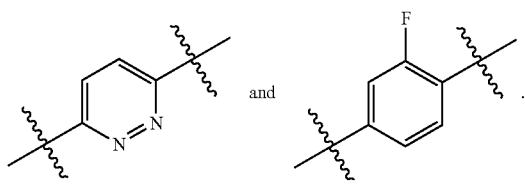 [SMILES: *c1ccc(*)nn1 ; *c1ccc(*)c(F)c1]

Preferably, R₁ is:

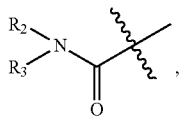

R$_2$ and R$_3$ are independently selected from the group consisting of H, C$_{1-6}$alkyl, (CH$_2$)$_{0-3}$-3~7-membered (such as (CH$_2$)$_{0-3}$-5~7-membered)cycloalkyl and heterocycloalkyl containing 1 or 2 heteroatoms, and the R$_2$ and R$_3$ are not hydrogen at the same time; wherein the C$_{1-6}$alkyl may be substituted by one or more substituents selected from the group consisting of halogen, hydroxyl, amino, cyano, C$_{1-6}$alkoxy, (C$_{0-6}$ alkyl) (C$_{0-6}$ alkyl) amino, (C$_{0-6}$ alkyl) thio, (C$_{1-6}$ alkyl)carbonyl and (C$_{1-6}$ alkyl) sulfonyl; the 3~7-membered (such as 5~7-membered)cycloalkyl or heterocycloalkyl is substituted by one R′″, wherein the R′″ is selected from the group consisting of hydrogen, C$_{1-6}$alkyl, hydroxyl, halogen and amino, the heteroatom of the heterocycloalkyl is selected from O, N, and S; or R$_2$ and R$_3$, together with the atoms attached thereto, form a 5, 6 or 7-membered ring, wherein,
the 5-, 6- or 7-membered ring is substituted by one R″, wherein the R″ is selected from hydrogen, C$_{1-6}$alkyl, hydroxyl, halogen and amino;
the 5, 6 or 7-membered ring, in addition to the N atom attaching to R$_2$ and R$_3$, further contain 0, 1 or 2 heteroatoms selected from O, N, and S.

More preferably, R₁ is:

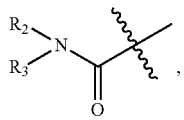

R$_2$ and R$_3$ are independently selected from the group consisting of H, C$_{1-6}$alkyl, (CH$_2$)$_{0-3}$-3~7-membered (such as (CH$_2$)$_{0-3}$-5~7-membered)cycloalkyl, and R$_2$ and R$_3$ are not hydrogen at the same time; wherein the C$_{1-6}$alkyl may be optionally substituted by one or more substituents selected from the group consisting of halogen, hydroxyl, amino, cyano, C$_{1-6}$alkoxy, (C$_{0-6}$ alkyl) (C$_{0-6}$ alkyl) amino, (C$_{0-6}$ alkyl) thio, (C$_{1-6}$ alkyl)carbonyl and (C$_{1-6}$ alkyl) sulfonyl; the 3~7-membered (such as 5~7-membered) cycloalkyl is substituted by one R′″, wherein the R′″ is selected from the group consisting of hydrogen, C$_{1-6}$alkyl, hydroxyl, halogen and amino; or R$_2$ and R$_3$, together with the atoms attached thereto, form a 5, 6 or 7-membered ring,
wherein,
the 5-, 6- or 7-membered ring is substituted by one R″, wherein the R″ is selected from hydrogen, C$_{1-6}$alkyl, hydroxyl, halogen and amino.

Further preferably, R₁ is:

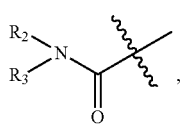

One of R$_2$ and R$_3$ is H, the other is selected from the group consisting of C$_{1-6}$alkyl, (CH$_2$)$_{0-3}$-3~7-membered (such as (CH$_2$)$_{0-3}$-5~7-membered)cycloalkyl; wherein the C$_{1-6}$alkyl may be optionally substituted by one or more substituents selected from the group consisting of halogen, hydroxyl, amino, cyano, C$_{1-6}$alkoxy, (C$_{0-6}$ alkyl) (C$_{0-6}$ alkyl) amino, (C$_{0-6}$ alkyl) thio, (C$_{1-6}$ alkyl)carbonyl and (C$_{1-6}$ alkyl) sulfonyl; the 3~7-membered (such as 5~7-membered) cycloalkyl is substituted by one R′″, wherein the R′″ is selected from hydrogen, C$_{1-6}$alkyl, hydroxyl, halogen and amino.

Preferably, R₁ is selected from:

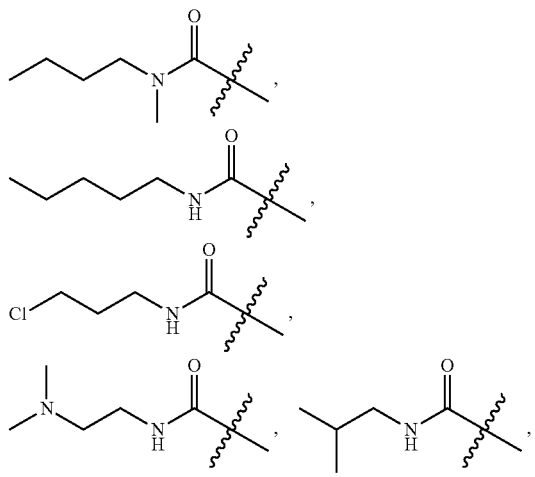

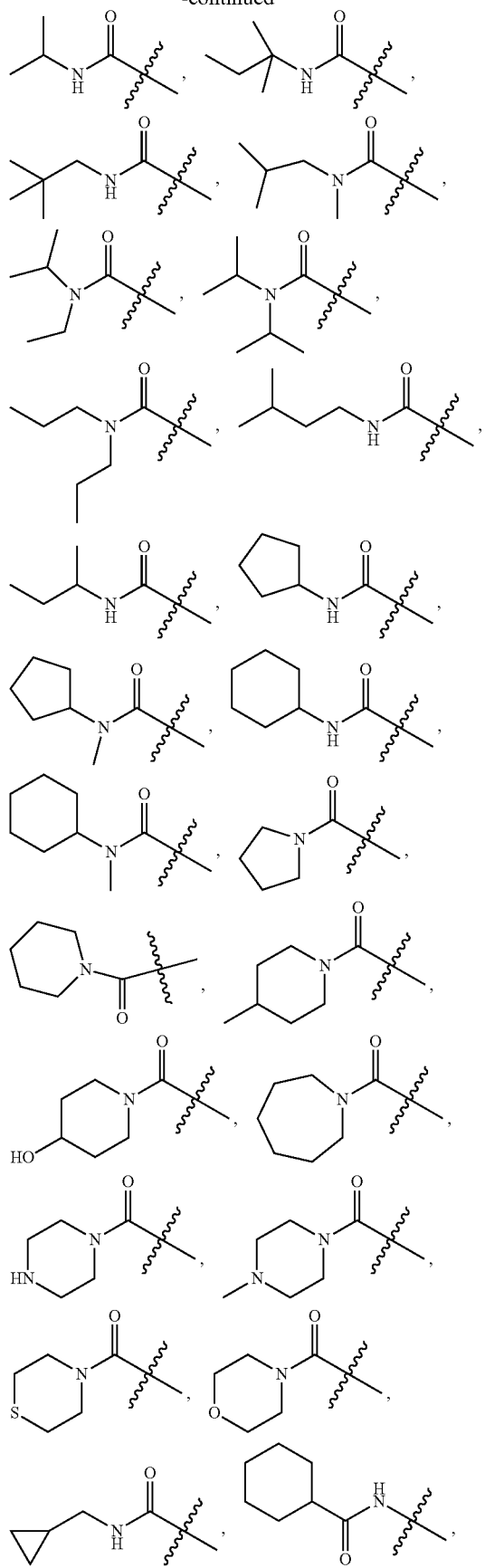
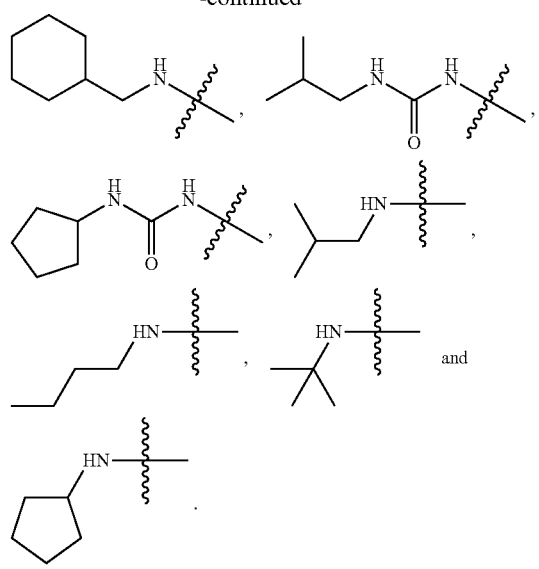
More preferably, $R_1$ is selected from:
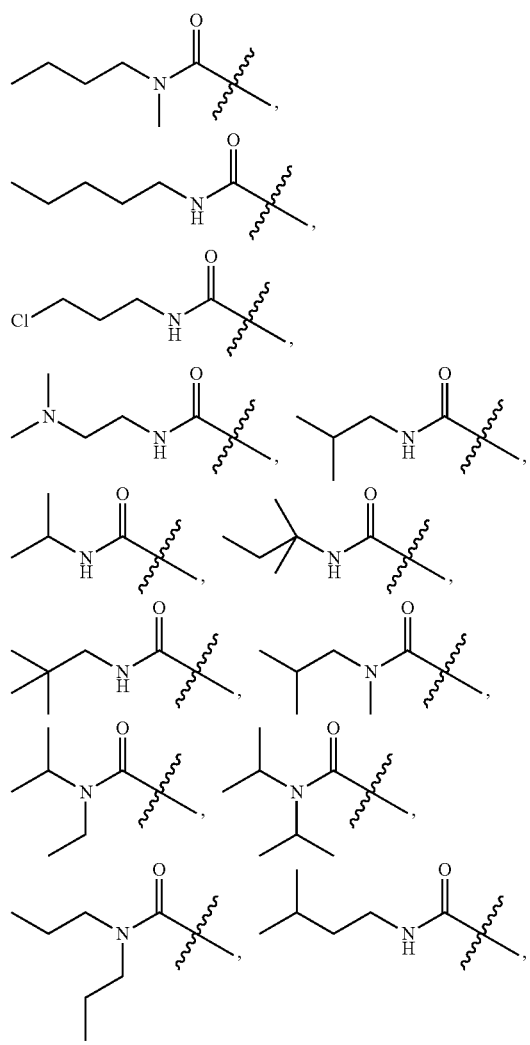

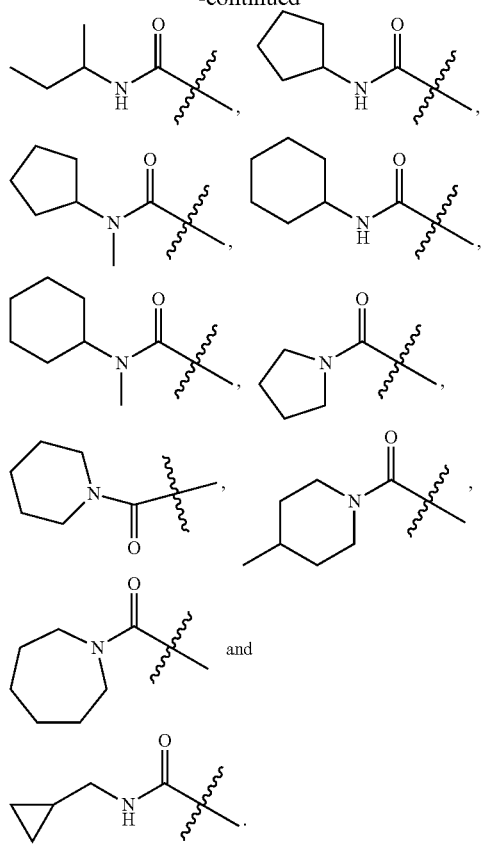
Preferably, Z is selected from:
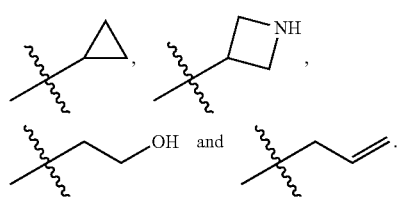
More preferably, Z is selected from:
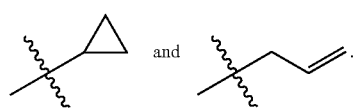
Most preferably, Z is:
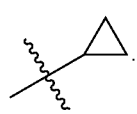
Preferably, the present invention provides a compound or a tautomer, an optical isomer, and a pharmaceutically acceptable salt thereof, selected from:
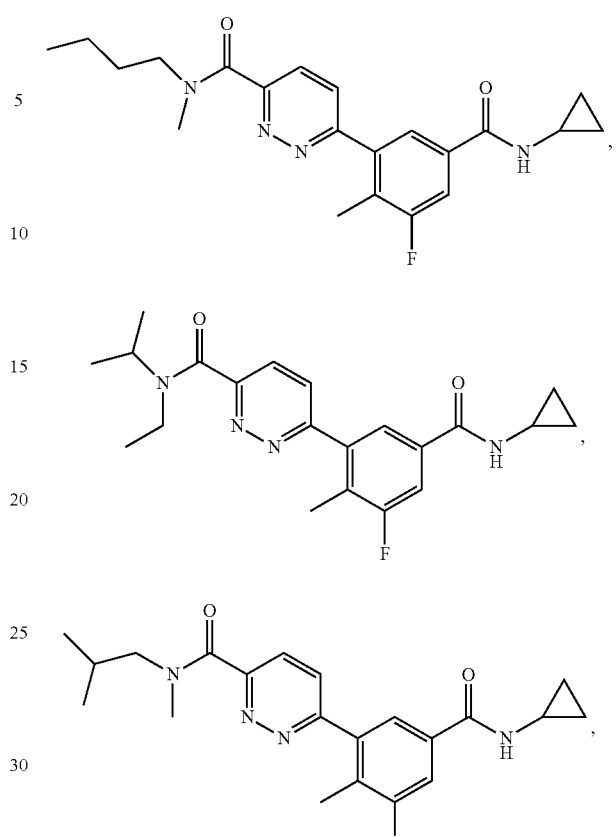
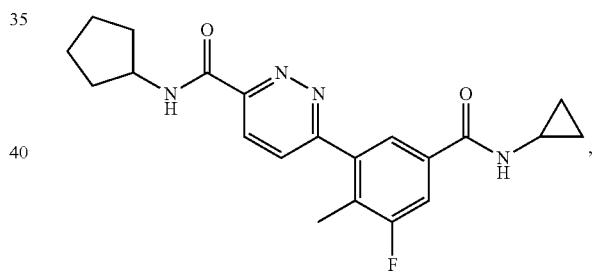
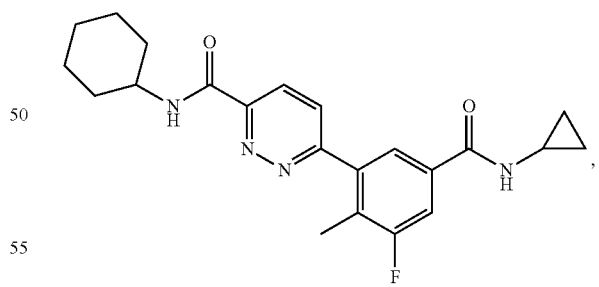
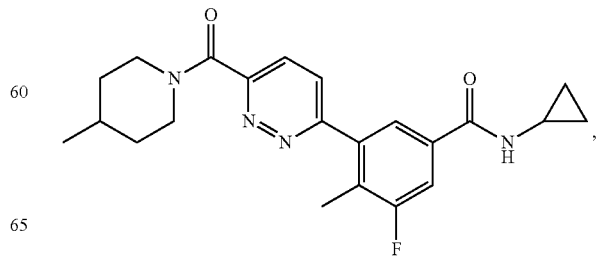

-continued
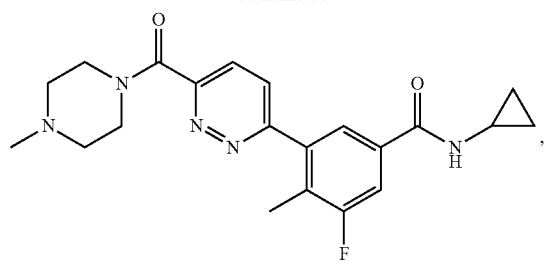
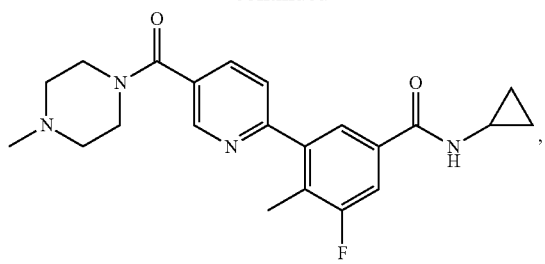
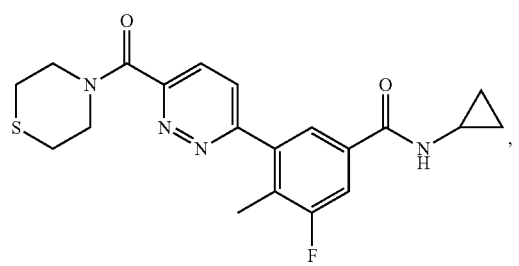
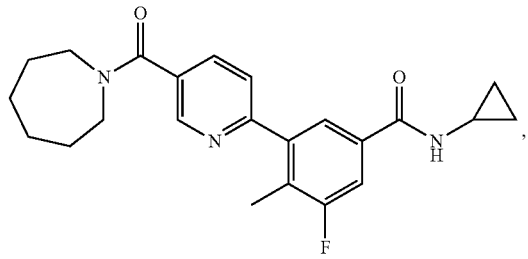
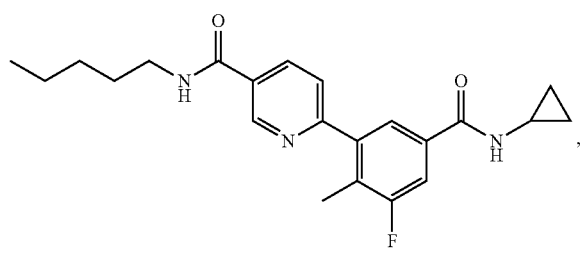
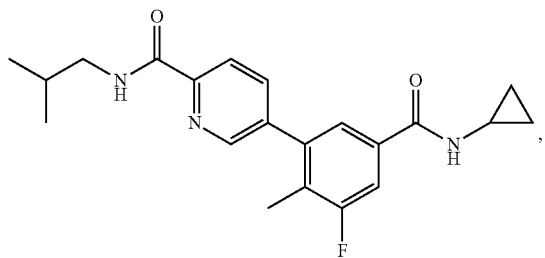
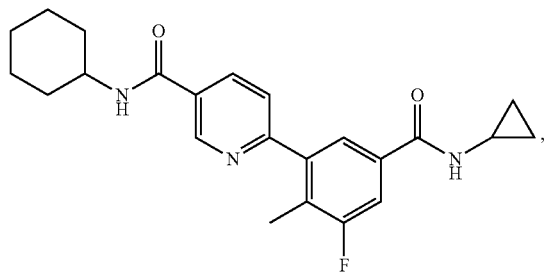
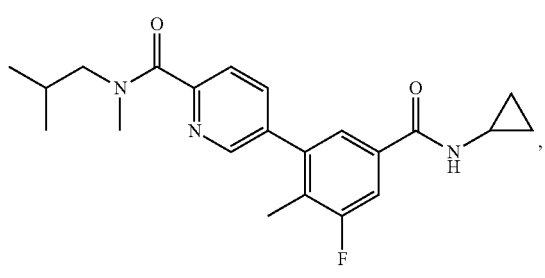
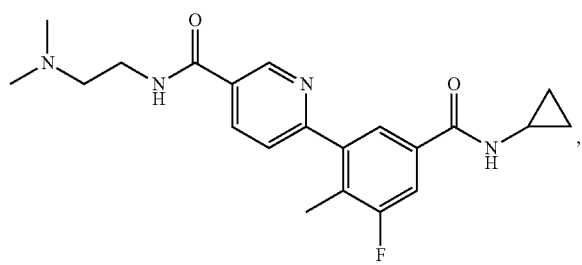
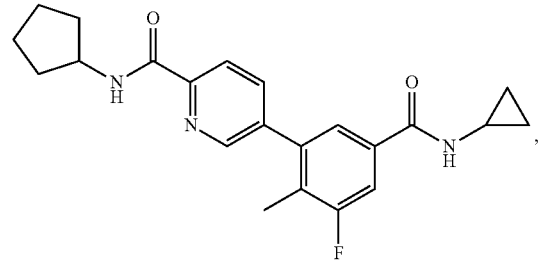
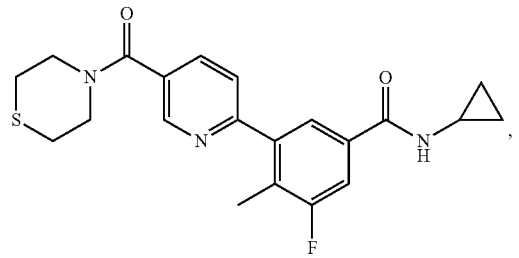
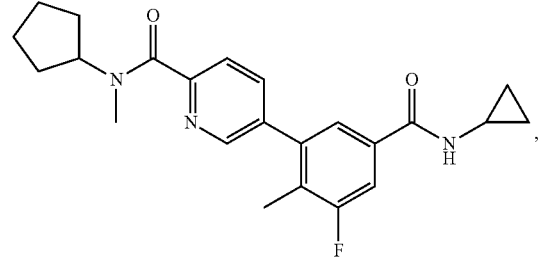

23
-continued
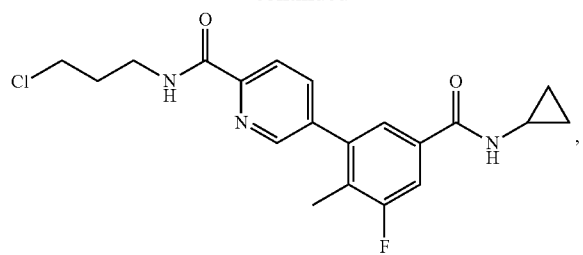
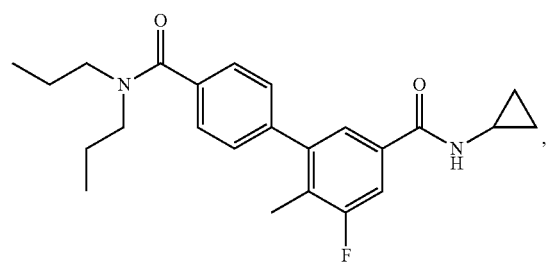
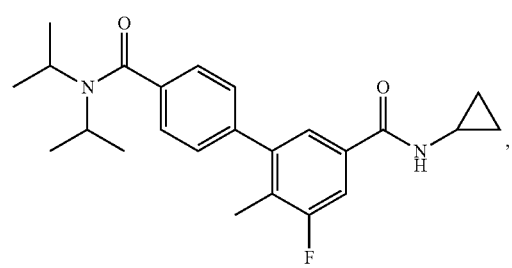
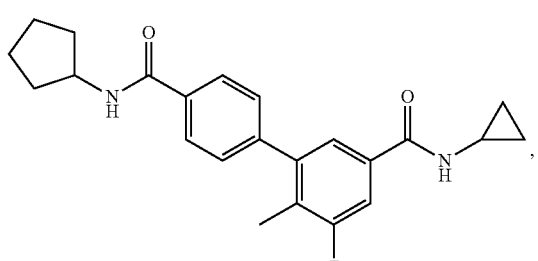
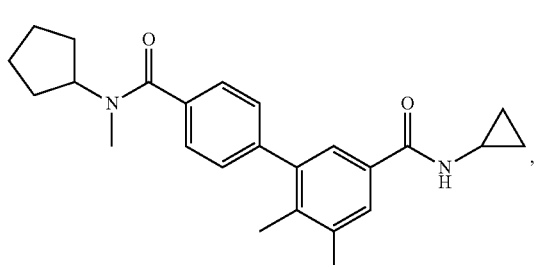
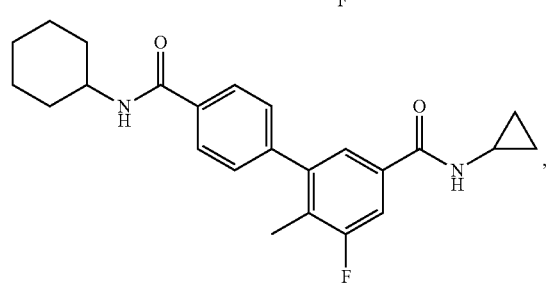
24
-continued
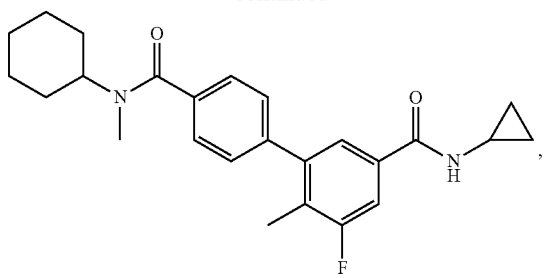
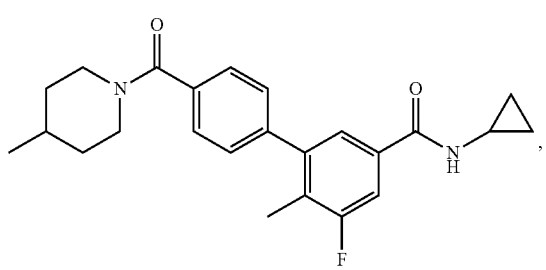
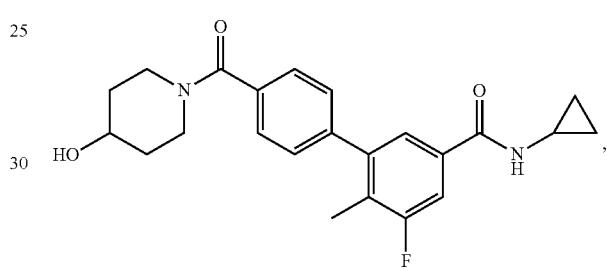
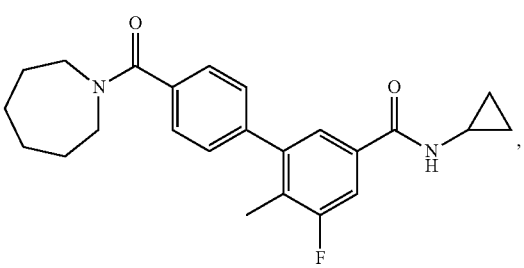
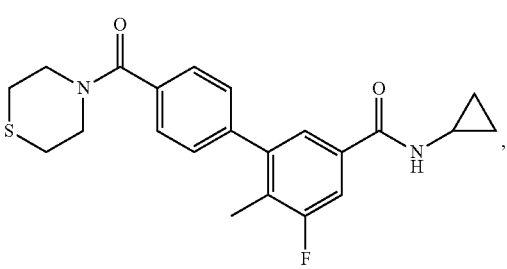
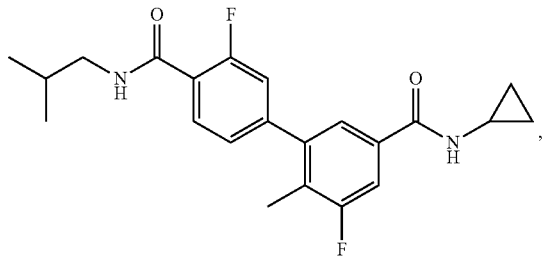

-continued
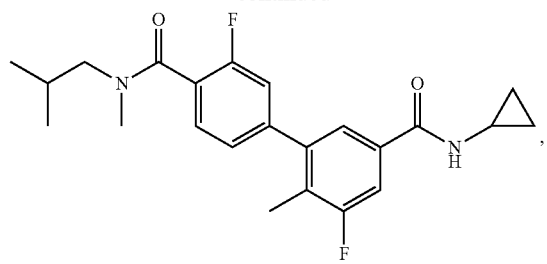
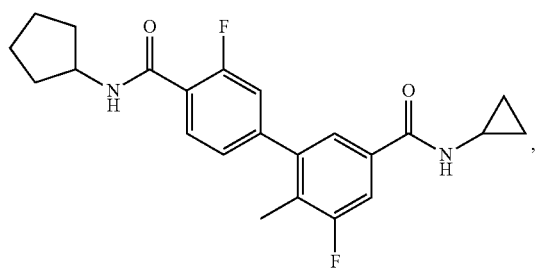
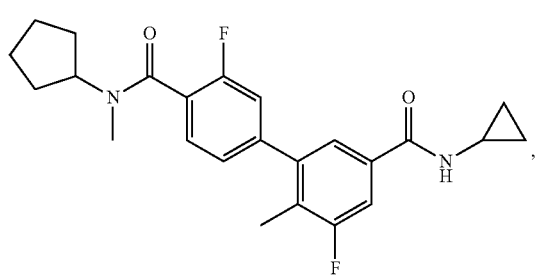
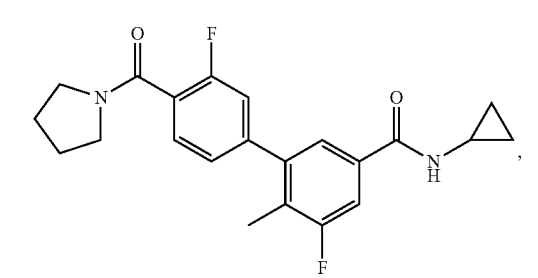
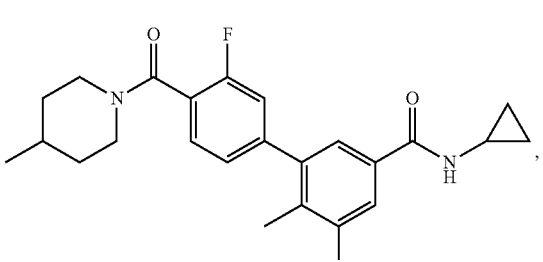
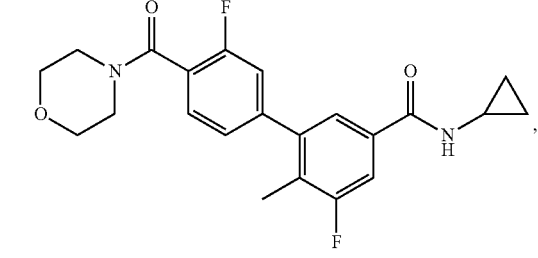
-continued
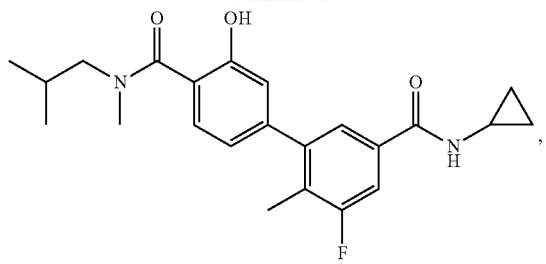
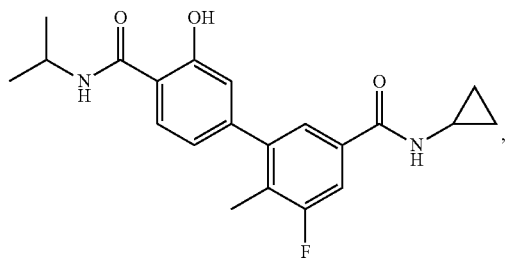
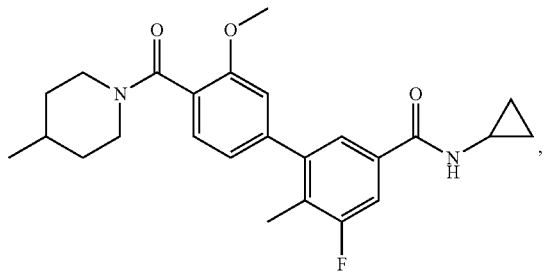
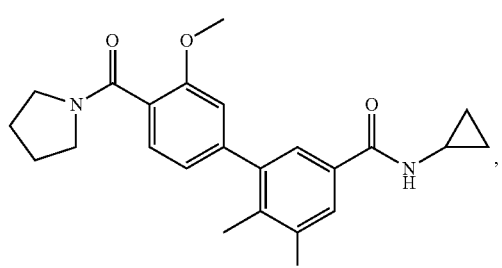
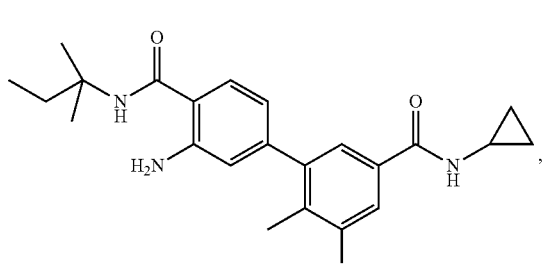
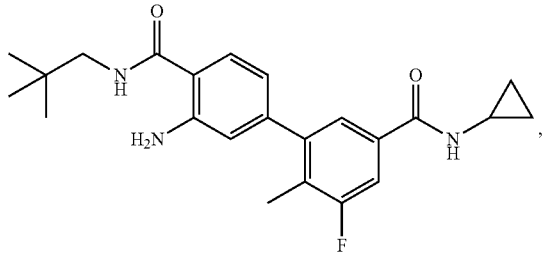

27
-continued
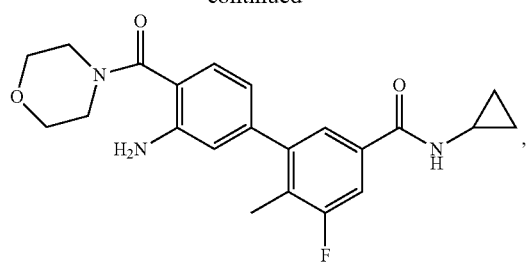
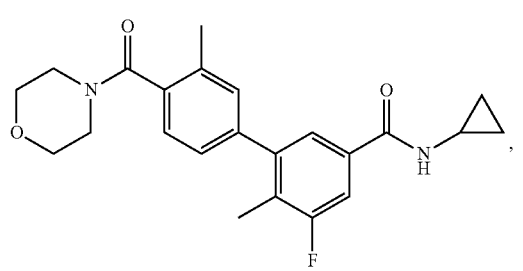
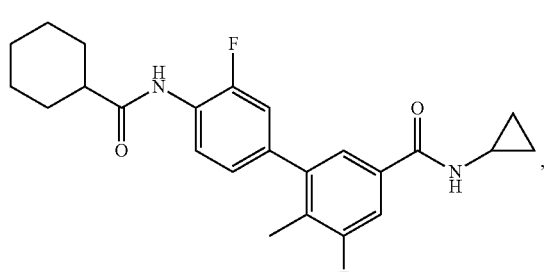
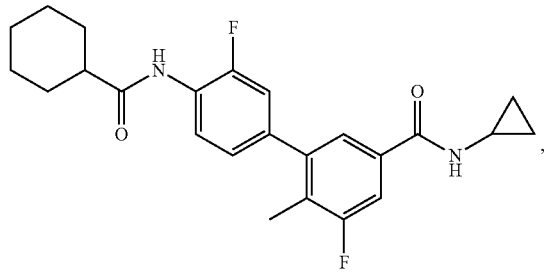
28
-continued
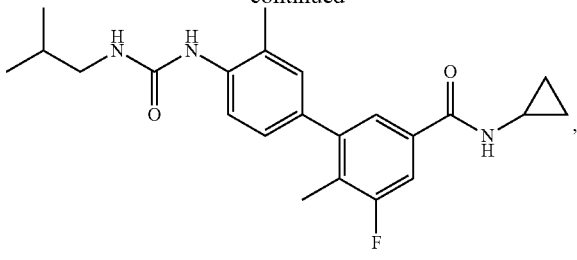
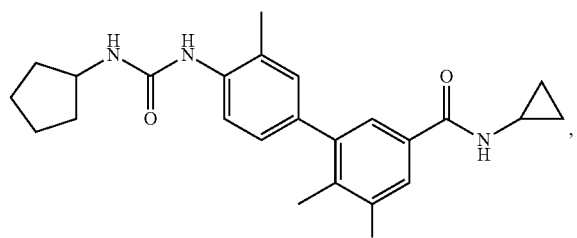
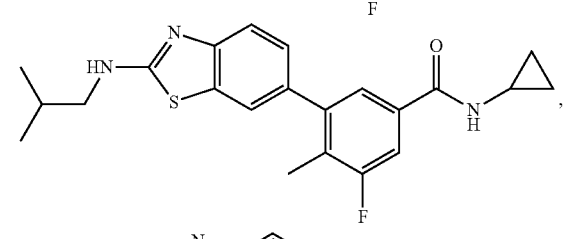
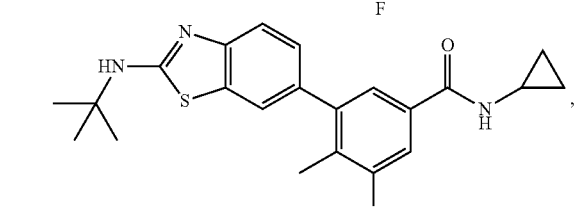
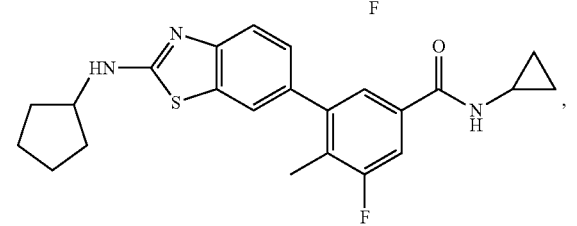

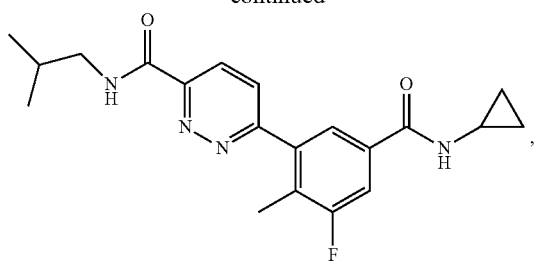
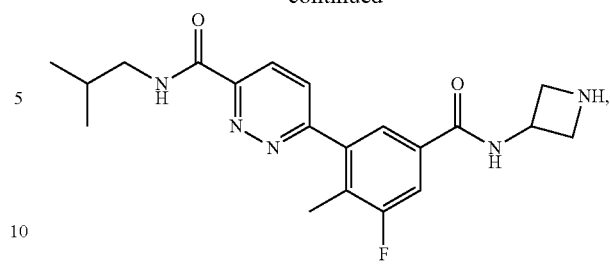
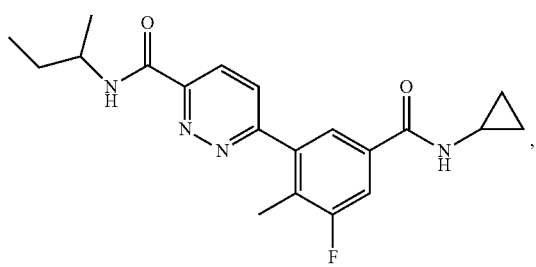
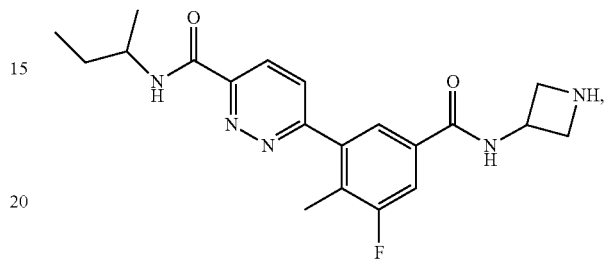
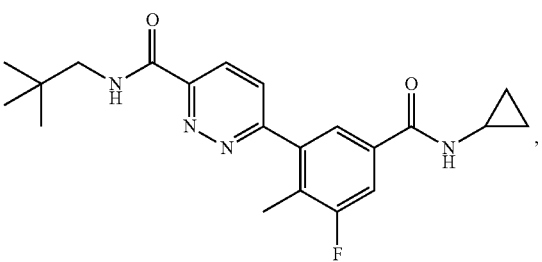
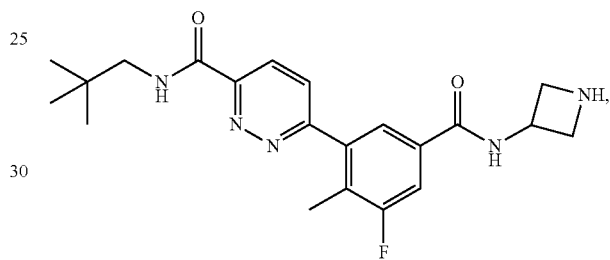
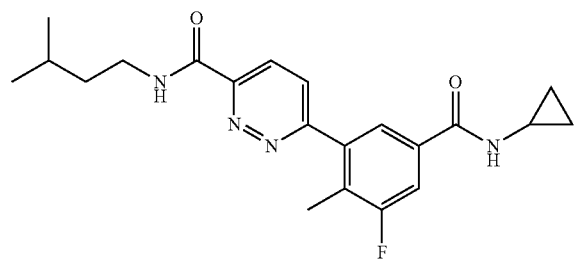
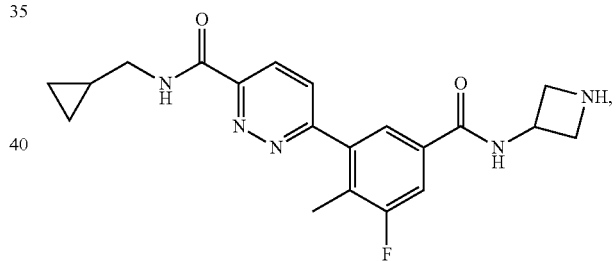
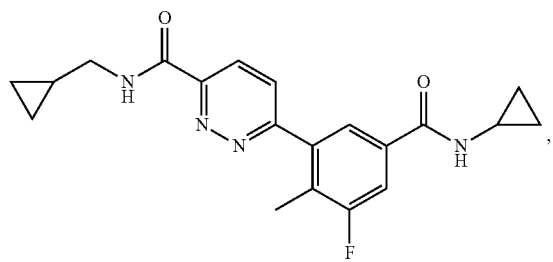
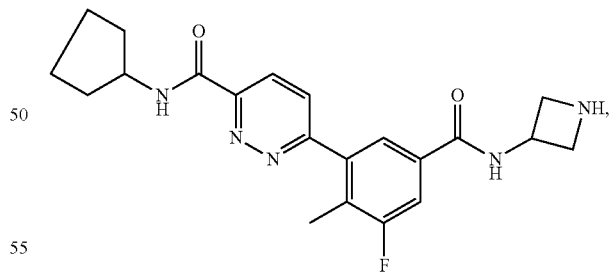
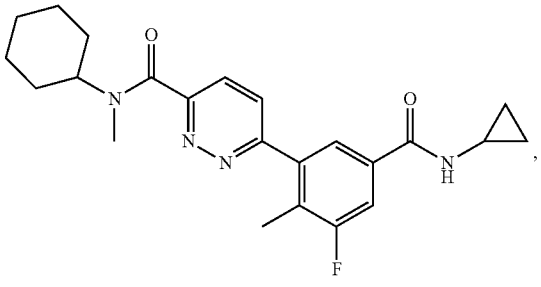
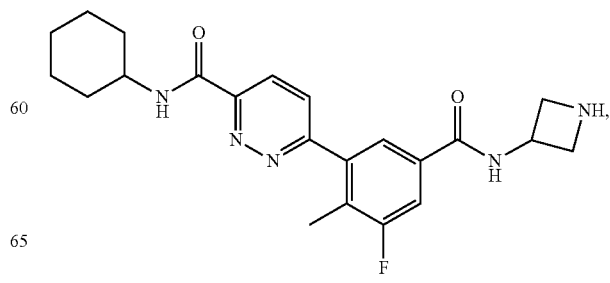

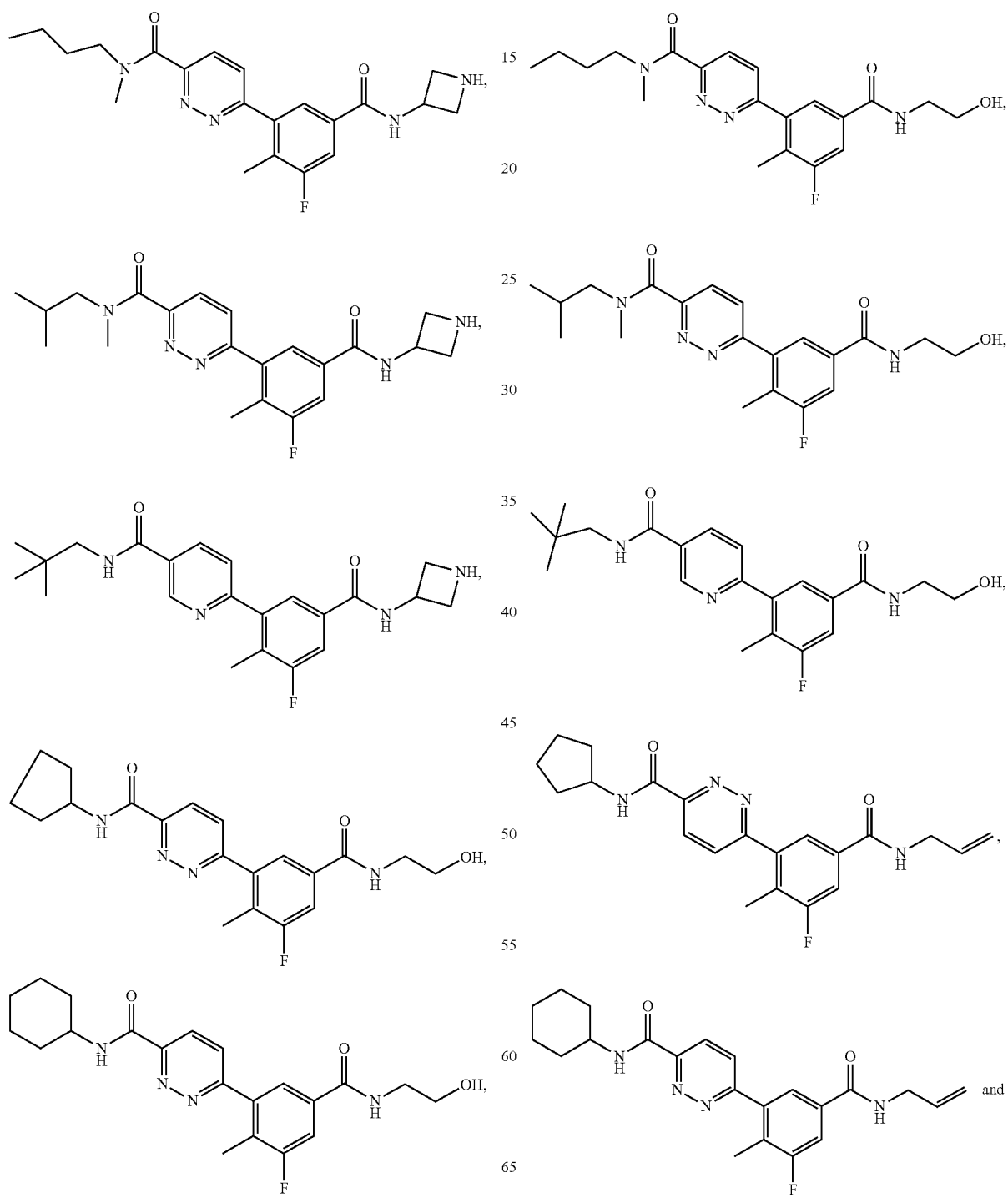

-continued

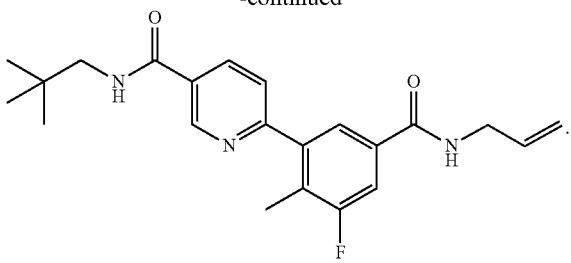

In another aspect, the present invention also provides a pharmaceutical composition, comprising the compound of formula I, or a tautomer, an optical isomer and a pharmaceutically acceptable salt thereof as described above.

In a further aspect, the present invention also provides a use of the compound of formula I, or a tautomer, an optical isomer and a pharmaceutically acceptable salt thereof as described above, or the pharmaceutical composition as described above in the manufacture of a medicament for the prevention and/or the treatment of symptoms or diseases mediated by p38 kinase activity or mediated by the cytokines produced by p38 kinase activity, wherein the diseases are for example selected from inflammatory disease, such as rheumatoid arthritis, chronic lung obstruction, cardiovascular disease, gout, psoriasis, asthma, tumor, diabetes mellitus arteriosclerosis, Crohn's disease and so on.

In still a further aspect, the present invention also provides a method for preparing the compound of formula I, or a tautomer, an optical isomer and a pharmaceutically acceptable salt thereof, as described above, comprising condensing a compound of formula II and a compound of formula III to form the compound of formula I:

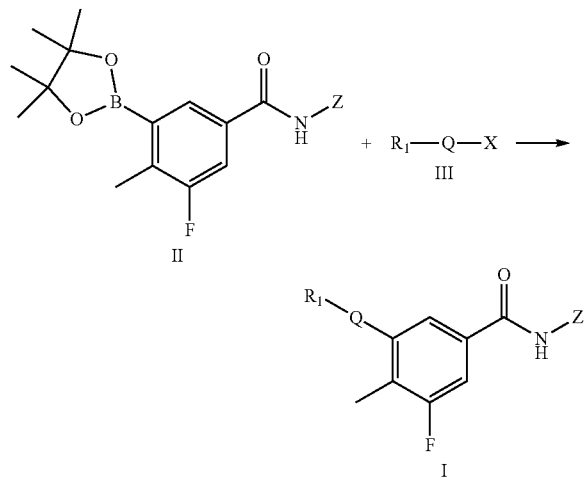

Q, Z and $R_1$ were defined as above, X is halogen, preferably, F, Cl, Br or I.

DESCRIPTION OF THE EMBODIMENTS

Geometric isomers may exist in the compounds of the present invention. Compounds of this invention may contain carbon-carbon double bonds or carbon-nitrogen double bonds in the E or Z configuration, in which the term "E" represents the higher ranked substituents on opposite sides of a carbon-carbon or carbon-nitrogen double bond and the term "Z" represents the higher order substituents (determined by the Cahn-Ingold Prelog priority rules) on the same side of a carbon-carbon or carbon-nitrogen double bond. The compounds of this invention may also exist as a mixture of "E" and "Z" isomers. The substituents around a cycloalkyl or a heterocycloalkyl are designated as cis- or trans-configuration.

Compounds of this invention may contain asymmetrically substituted carbon atoms in the R or S configuration, wherein the terms "R" and "S" are as defined in IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms having excess of one configuration over the other are assigned the configuration in excess, preferably an excess of about 85%-90%, more preferably an excess of about 95%-99%, and still more preferably an excess greater than about 99%. Accordingly this invention is meant to embrace racemic mixtures, relative and absolute stereoisomers and the mixtures of relative and absolute stereoisomers.

Compounds of this invention containing NH, C(O)OH, OH or SH moieties may have attached thereto prodrug-forming moieties. The prodrug-forming moieties are removed through metabolic processes and the compounds having the freed hydroxyl, amino or carboxylic acid will be released in vivo. Prodrugs are useful for adjusting pharmacokinetic properties of the compounds, such as solubility and/or hydrophobicity, absorption in the gastrointestinal tract, bioavailability, tissue penetration, and rate of clearance.

Prodrugs are derivatives of an active drug, designed to ameliorate some identified, undesirable physical or biological properties. The physical properties are usually related solubility (too much or not enough lipid or aqueous solubility) or stability, while problematic biological properties include too rapid metabolism or poor bioavailability which may be related to a physicochemical property.

Prodrugs are usually prepared by: a) formation of esters, hemi esters, carbonate esters, nitrate esters, amides, hydroxamic acids, carbamates, imines, Mannich bases, phosphate salts, phosphate esters, and enamines of the active drug, b) functionalizing the drug with azo, glycoside, peptide, and ether functional groups, c) use of aldehydeamines, hemi-aldehydeamines, polymers, salts, complexes, phosphoramides, acetals, hemiacetals, and ketal forms of the drugs. For example, see AndrejusKorolkovas's, "Essentials of Medicinal Chemistry", John Wiley-Interscience Publications, John Wiley and Sons, New York (1988), pp. 97-118, which is incorporated in its entirety by reference herein. Esters can be prepared from substrates containing either a hydroxyl group or a carboxy group by general methods known to persons skilled in the art. The typical reactions of these compounds are substitutions replacing one of the heteroatoms by another atom. Amides can be prepared from substrates containing an amino group or a carboxy group in similar fashion. Esters can also react with amines or ammonia to form amides. Another way for preparing amides is to heat carboxylic acid and amine together.

Compounds of this invention can exist in isotope-labeled or isotope-enriched form, the compounds have one or more atoms, the atomic mass or mass number of these atoms are different from the atomic mass or mass number of the numerous atoms usually found in nature. Isotopes can be radioactive or non-radioactive isotopes. Isotopes of atoms such as hydrogen, carbon, phosphorous, sulfur, fluorine, chlorine and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl and $^{125}$I. Compounds that contain other isotopes of these and/or other atoms are within the scope of this invention.

As used herein, the term "tautomer" represents functional group isomers caused from the rapid migration of one atom between two positions, they may be interconverted to each other, usually achieve an equilibrium state at one status, one of which is the main status, such as the tautomers of enol and ketone.

As used herein, the term "optical isomer" denotes the substances having identical molecular structure, similar physical and chemical properties, but different optical activity.

As used herein, the term "salt" is selected from hydrochloride, hydrobromide, sulfate, sulfite, phosphate, mesylate, tosilate, maleate, tartrate, malate, fumarate, citrate, etc.

As used herein, the term "$C_{1-6}$ alkyl" denotes a straight or branched saturated hydrocarbon radical having from 1 to 6 carbon atoms, such as methyl, ethyl, n-propyl, isopropyl, n-butyl, isobutyl, sec-butyl, tert-butyl, etc.

As used herein, the term "halogen" denotes fluorine, chlorine, bromine or iodine.

As used herein, the term "$C_{1-6}$alkoxy" denotes "$C_{1-6}$ alkyl-O—", wherein $C_{1-6}$ alkyl is defined as above.

As used herein, the term "$(C_{0-6}$ alkyl$)(C_{0-6}$ alkyl) amino" denotes amino substituted by two independently $C_{0-6}$ alkyl, substituted by $C_0$alkyl denotes no substitution.

As used herein, the term "$(C_{0-6}$ alkyl) thio" denotes thio substituted by $C_{0-6}$ alkyl, substituted by $C_0$alkyl denotes no substitution.

As used herein, the term "$(C_{1-6}$ alkyl)carbonyl" denotes carbonyl substituted by $C_{1-6}$ alkyl, wherein $C_{1-6}$ alkyl is defined as above.

As used herein, the term "$(C_{1-6}$ alkyl) sulfonyl" denotes sulfonyl substituted by $C_{1-6}$ alkyl, wherein $C_{1-6}$ alkyl is defined as above.

As used herein, the term "3~7-membered cycloalkyl" denotes cyclopropyl, cyclobutyl, cyclopentyl, cyclohexyl or cycloheptyl.

As used herein, the term "5~7-membered cycloalkyl" denotes cyclopentyl, cyclohexyl or cycloheptyl.

As used herein, the term "3~7-membered (such as 5~7-membered)heterocycloalkyl containing 1 or 2 heteroatoms" denotes 1 or 2 C atoms in cyclopropyl, cyclobutyl, cyclopentyl, cyclohexyl or cycloheptyl substituted by O, N or S, such as oxacyclopropyl, azacyclopropyl, oxacyclobutyl, azacyclobutyl, pyrrolidine, tetrahydrofuryl, tetrahydropyranyl, piperidyl, piperazinyl, morpholinyl, thiomorpholinyl, dioxanyl, epoxyhexyl, azacycloheptyl, tetrahydrothiophen or sulfurized cyclopentyl.

As used herein, the term "—$(CH_2)_{0-1}$—" denotes methylene or a bond, that is, "—$(CH_2)_1$—" denotes methylene, "—$(CH_2)_0$—" denotes a bond.

As used herein, the term "—$(CH_2)_{0-3}$—" denotes a bond, methylene or 2 to 3 successive methylene. As used herein, the term "—$(CH_2)_{0-1}$-5~7-membered cycloalkyl" denotes 5~7-membered cycloalkyl attached with methylene or a bond, the 5~7-membered cycloalkyl is defined as above.

As used herein, the term "5~7-membered ring" denotes a ring containing 5, 6 or 7 ring atoms, the ring contain at least one N as ring atom, in addition to N, the 5, 6 or 7-membered ring may contain 0, 1 or 2 heteroatoms selected from O, N and S. The 5-, 6- or 7-membered ring includes but not limited to pyrrolidine, piperidine, piperazine, morpholine, thiomorpholine, azacycloheptane etc.

As used herein, the meanings of the connecting bond of the term "Q" are as follows: bond 1 connects with a benzene ring, bond 2 connects with $R_1$.

In another aspect, the present invention provides a pharmaceutical composition, comprising a compound of the present invention, or a tautomer, an optical isomer and a pharmaceutically acceptable salt thereof.

The pharmaceutical composition of the present invention can be administered orally, for example in the form of granules, tablets or capsules; parenterally (including intravenous injection, subcutaneous injection, intramuscular injection, intrathecal injection or infusion), for example in the form of sterile solutions suspensions or emulsion; topically, for example in the form of ointment or cream; rectally, for example in the form of suppositories; or pulmonarily, for example in the form of inhalant. The above mentioned composition scan generally be prepared by conventional procedures using conventional pharmaceutical excipients.

In a further aspect, the present invention provides a use of the compounds of the present invention, or a tautomer, an optical isomer and a pharmaceutically acceptable salt, or the pharmaceutical composition thereof in the manufacture of a medicament for the prevention and/or the treatment of symptoms or diseases mediated by p38 kinase activity or mediated by the cytokines produced by p38 kinase activity, wherein the diseases are selected from for example inflammatory disease, such as rheumatoid arthritis, chronic lung obstruction, cardiovascular disease and gout, psoriasis, asthma, tumor, diabetes mellitus, arteriosclerosis, Crohn's disease and so on.

In still a further aspect, the present invention also provides a method for preparing the compound of formula I, or a tautomer, an optical isomer and a pharmaceutically acceptable salt thereof, comprising condensing a compound of formula II and a compound of formula III to form the compound of formula I:

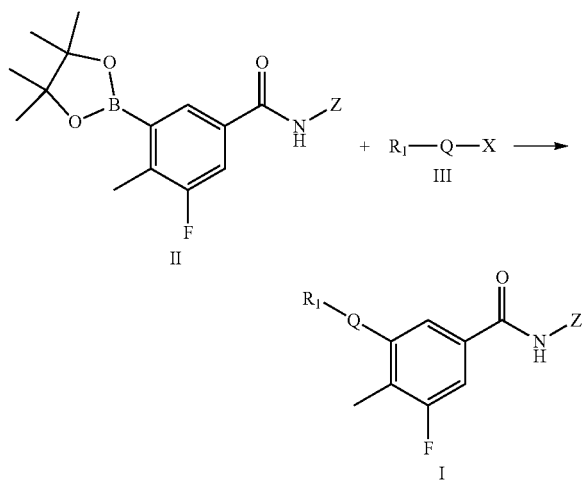

Q, Z and R were defined as claim 1, X is halogen, preferably, F, Cl, Br or I.

Preferably, the solvent of the condensation reaction is isopropyl alcohol.

Preferably, in the condensation reaction, the molar ratio of the compound of formula II to the compound of formula III is 0.8~1.2:1, preferably 1:1.

Preferably, the condensation reaction is carried out under basic condition, and the base is preferably sodium bicarbonate.

Preferably, the condensation reaction is carried out under catalytic condition, and the catalyst is preferably tetrakis(triphenylphosphine) palladium.

Preferably, the temperature of the condensation reaction is 80-100° C.

The compounds of the present invention have good biological activity, high bioavailability and good safety.

These effects may be confirmed by the following experiment.

I. In Vitro Cell Experiment

Experimental Materials:

Cells: human monocytic leukemia THP-1 cells (obtained from the Shanghai Cell Bank of Chinese Academy of Sciences).

Lipopolysaccharides: from *Escherichia coli* O55: B5, L2880 (Sigma).

Kit: Human TNF-α Elisa MAX Deluxe Set, 430206 (Biolegend)

Experimental Method:

Human monocytic leukemia THP-1 cells were inoculated into a 96-well plate at a density of $5*10^5$/well and adherent cultured overnight, different concentration of compounds diluted with culture medium were added and incubated for 2 h, and then LPS (10 µg/ml) were added to stimulate for 2 h, after centrifugation, the supernatant was taken out, and the TNF-α concentration was tested by using Human TNF-α Elisa MAX Deluxe Set to obtain the IC50 values of the compounds.

The activity of the compounds of the present invention were tested, the results indicated that the compounds of the present invention had strong inhibitory effects on TNF-α, the $IC_{50}$ values were less than 0.5 µM, preferably less than 0.1 µM, more preferably less than 20 nM, still more preferably less than 10 nM, most preferably less than 5 nM.

| Example No. | IC$_{50}$(nM) |
|---|---|
| 3 | B |
| 4 | A |
| 5 | A |
| 9 | B |
| 10 | A |
| 14 | B |
| 15 | A |
| 16 | A |
| 17 | A |
| 20 | B |
| 22 | A |
| 23 | B |
| 24 | B |
| 25 | A |
| 26 | B |
| Comparative example | C |
| 28 | B |
| 30 | A |
| 31 | A |
| 32 | A |
| 33 | A |
| 41 | A |
| 42 | B |
| 44 | A |
| 47 | B |
| 50 | A |
| 51 | A |
| 52 | B |
| 54 | B |
| 55 | B |
| 56 | B |
| 57 | A |
| 58 | A |
| 59 | A |
| 60 | B |
| 61 | A |
| 62 | B |
| 79 | B |
| 80 | B |
| 81 | B |
| Comparative example | C |

A: Less than 5 nM;
B: Less than 10 nM and greater than or equal to 5 nM;
C: Less than 20 nM and greater than or equal to 10 nM;
D: Less than 0.1 µM and greater than or equal to 20 nM;
E: Less than 0.5 µM and greater than or equal to 0.1 µM.

II. Assay of p38 Kinase Activity

Experimental Method: 40 nM p38a was added into a reaction buffer, which include 20 mM HEPES (4-hydroxyethylpiperazine ethanesulfonic acid), 5 mM MgCl$_2$ and 1 mM DTT (dithiothreitol) at pH 7.4. 40 µM phosphorylated peptide substrate was added, followed by different concentrations of drugs and 100 µM ATP (adenosine triphosphate), and reacted for 90 minutes in dark. The fluorescence values were determined at excitation and emission wavelengths of 544 nM and 590 nM respectively. The IC$_{50}$ values of the compounds were obtained according to the fluorescence values.

The activity of the compounds of the present invention were tested, the results indicated that the compounds of the present invention had strong inhibitory effects on p38 kinase, the IC$_{50}$ values were less than 0.5 µM, preferably less than 0.1 µM, more preferably less than 20 nM, still more preferably less than 10 nM, most preferably less than 5 nM.

| Example No. | IC$_{50}$(nM) |
|---|---|
| 3 | A |
| 4 | A |
| 5 | A |
| 9 | B |
| 15 | A |
| 16 | A |
| 25 | B |
| 30 | A |
| 31 | A |
| 32 | A |
| 44 | B |
| 51 | B |
| 52 | B |
| 55 | B |
| 56 | B |
| 57 | A |
| 58 | A |
| 59 | A |
| 60 | A |
| 61 | A |
| 62 | A |
| 79 | A |
| 80 | A |
| Comparative example | C |

A: Less than 5 nM;
B: Less than 10 nM and greater than or equal to 5 nM;
C: Less than 20 nM and greater than or equal to 10 nM:
D: Less than 0.1 µM and greater than or equal to 20 nM;
E: Less than 0.5 µM and greater than or equal to 0.1 µM.

III. CYP450 Enzyme Inhibition Test

Experimental Method: 4-hydroxydiclofenac (the substrate for CYP450 and 2C9 enzymes) and different doses of compounds were added into human liver microsome (Xenotech, LLC), then NADPH (Reduce dcoenzyme II, Chemimpex international, Inc.) was added, mixed, and then incubated in 37° C. water bath, at the terminal time, the stop solution (200 ng/mL tolbutamide and 200 ng/mL labetalol dissolved in acetonitrile) was added to stop the reaction, methanol or ethanol was used to precipitate proteins, the concentration of the metabolites of substrates was determined by using LC-MS/MS to obtain the $IC_{50}$ values of compounds on CYP450 and 2C9 enzyme.

The inhibition effects of the compounds of the present invention on CYP450 enzyme were tested, the results indicated that the compounds of the present invention had low inhibitory effects on CYP450, 2C9 enzymes, therefore, the compounds of the present invention have higher safety.

| Example No. | $IC_{50}(\mu M)$ |
|---|---|
| 3 | >50 |
| 4 | >50 |
| 5 | >50 |
| 16 | >50 |
| 42 | >50 |
| Comparative example | <20 |
| 44 | >50 |
| 57 | >50 |
| 58 | >50 |
| 59 | >50 |
| 61 | >50 |

IV. Pharmacokinetics Experiment

Experimental Method: SD rats were orally administrated the compounds and the blood samples were taken from the eye orbit of the rat sat different time intervals after administration (0.25, 0.5, 1, 2, 4, 6, 8, 24, 48 h). The collected whole blood was anticoagulant by EDTA (Ethylene Diamine Tetraacetic Acid Sodium) and 3000 g of samples were centrifugated to obtain the rats' plasma samples, methanol or ethanol was used to precipitate proteins, the drug concentration of the rats' plasma samples was determined, the drug concentration-time curve was plotted to calculate the pharmacokinetic parameters. The pharmacokinetic behavior in rats after administration was described by non-compartmental models statistical moment parameter.

The pharmacokinetic experiments were carried out for the compounds. The experimental results showed that the compounds had high bioavailability.

| Example No. | $AUC_{0-t}$(ng·h/mL) |
|---|---|
| 57 | 22097 |
| 59 | 11319 |
| 61 | 12190 |
| Comparative example | 9633 |

EXAMPLES

The illustrative preparation methods of the compounds of the invention are in the following examples. The raw materials are prepared according to the literature procedures or commercially available, purchased from J&K Chemical Ltd., Inno ChemLLC., Aladdin Regent Company, Alfa Aesar and Accela ChemBio (Shang Hai) Co. Ltd.

The following abbreviations are used throughout the experiments and have the following meaning:
DMF N,N-dimethyl formamide
Pd(dppf)Cl$_2$ 1,1'-Bis(diphenylphosphino)ferrocene palladium dichloride
Pd(PPh$_3$)$_4$ Tetrakis(triphenylphosphine)palladium Preparation Examples (1) Compound II was prepared according to the following schemes:

Scheme 1:

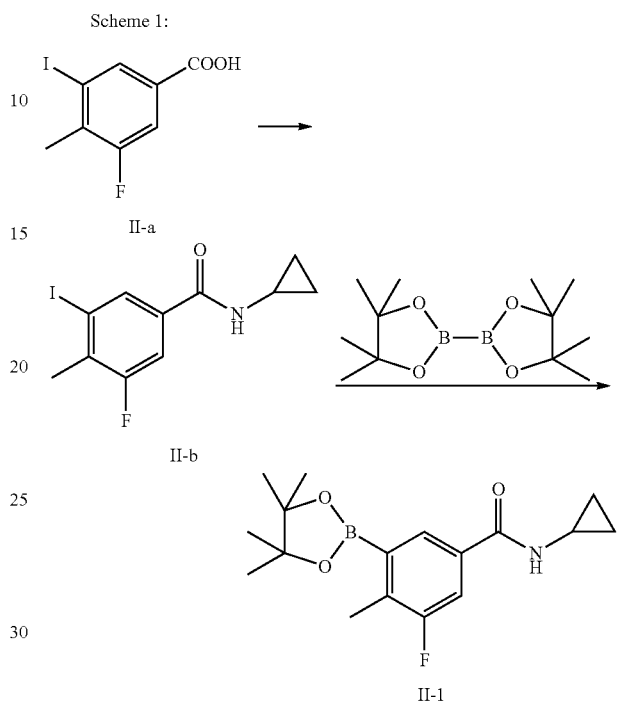

Step (1)

Preparation of N-cyclopropyl-3-fluoro-5-iodo-4-methylbenzamide (Compound II-b)

3-fluoro-5-iodo-4-methylbenzoic acid (compound II-a, 36 mmol) and thionyl chloride (50 mL) were added into a reaction flask and heated to reflux for 6 hours at 80° C. The excess of thionyl chloride was evaporated under reduced pressure to obtain a pale yellow oil, dichloromethane (30 mL) was added thereinto and the resulting product was used for the subsequent reaction.

Cyclopropanamine (38.6 mmol) was dissolved in dichloromethane (50 mL) in a reaction flask and sodium carbonate (71.7 mmol) was added, the above acyl chloride in dichloromethane was added dropwise at 0-5° C. After completion of dropping, the reaction was carried out at room temperature for 1 hour. After completion of the reaction, water (50 mL) was added and stirred for phase separation. The organic phase was washed with 5% hydrochloric acid (50 mL) and saturated sodium carbonate solution (50 mL), dried over anhydrous sodium sulfate, and then filtered and concentrated to give a white solid (11.25 g, yield: 98.0%), which is compound II-b.

Step (2): Preparation of N-cyclopropyl-5-fluoro-4-methyl-3-(4,4,5,5-tetramethyl-[1,3,2]-dioxaborolan-2-yl)benzamide (Compound II-1)

Compound II-b (35.1 mmol), bis(pinacolato)diboron (52.9 mmol), potassium acetate (176.4 mmol) and Pd(dppf)

Cl$_2$ (0.36 mmol) were added into anhydrous DMF (10 ml) in a reaction flask and reacted at 80° C. under stirring for 12 hours. After completion of the reaction, filtration was carried out, water (100 mL) was added into the filtrate, and then ethyl acetate (50 mL) was added to extract three times. The organic phase was combined, dried and concentrated under reduced pressure to dryness. The residue was recrystallized with cyclohexane to give a white solid (6.2 g, yield: 55.4%), which is compound II-1.

Scheme 2:

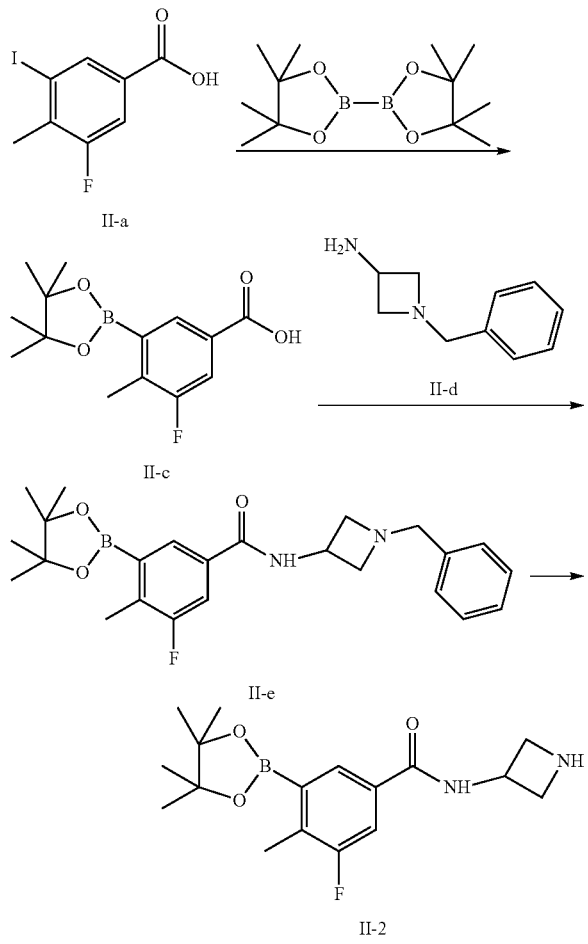

Step 1

Preparation of 3-fluoro-4-methyl-5-(4,4,5,5-tetramethyl-1,3,2-dioxaborolan-2-yl)benzoic acid (Compound II-c)

Compound II-a (14.0 g, 50.0 mmol) and bis(pinacolato)diboron (19.0 g, 75.0 mmol) were suspended in 300 mL DMF, potassium acetate (14.7 g, 150 mmol) and Pd(dppf)Cl$_2$ (3.65 g, 5.0 mmol) were added respectively and reacted at 100° C. for 18 hours. After completion of the reaction, the resulting substance was cooled to room temperature and filtered, 500 mL water was added thereinto, ethyl acetate (300 mL×3) was added to extract. The organic phase was combined, washed with 1N diluted hydrochloric acid (200 mL×2) and concentrated under reduced pressure to dryness. The residue was recrystallized with 100 mL isopropyl ether to give a white solid (9.87 g, yield: 70.5%), which is compound II-c.

Step 2

Preparation of N-(1-benzylazetidin-3-yl)-3-fluoro-4-methyl-5-(4,4,5,5-tetramethyl-1,3,2-dioxaborolan-2-yl)benzamide (Compound II-e)

Compound II-c (2.80 g, 10.0 mmol), 1-3(dimethylaminopropyl)-3-ethylcarbodiimide hydrochloride (2.11 g, 11.0 mmol) and 1-hydroxybenzotriazole (1.49 g, 11.0 mmol) were suspended in 100 mL dichloromethane and stirred at room temperature for 30 min. Compound II-d (1.78 g, 11.0 mmol) was added thereinto and the reaction was continued at room temperature for 8 hours. After completion of the reaction, 100 mL 1N diluted hydrochloric acid was added for phase separation. The organic phase was concentrated under reduced pressure. The residue was purified by column chromatography (petroleum ether/ethyl acetate=5:1 to 1:1) to give a white solid (4.02 g, yield: 94.8%), which is compound II e.

Step 3

Preparation of N-(azetidin-3-yl)-3-fluoro-4-methyl-5-(4,4,5,5-tetramethyl-1,3,2-dioxaborolan-2-yl)benzamide (Compound II-2)

Compound II-e (3.99 g, 9.4 mmol) and 10% Pd/C (0.40 g) were suspended in 100 mL methanol, hydrogenated at room temperature under normal pressure for 5 hours and filtered. The organic phase was concentrated under reduced pressure. The residue was purified by column chromatography (petroleum ether/ethyl acetate=5:1 to 1:1) to give a white solid (2.30 g, yield: 73.2%), which is compound II-2.

Scheme 3:

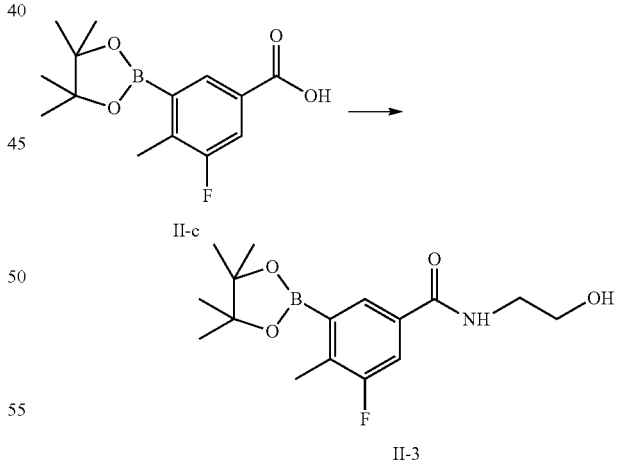

Step 1

Preparation of 3-fluoro-N-(2-hydroxyethyl)-4-methyl-5-(4,4,5,5-tetramethyl-1,3,2-dioxaborolan-2-yl) benzamide (Compound II-3)

Compound II-c (2.80 g, 10.0 mmol), 1-(3-dimethylaminopropyl)-3-ethylcarbodiimide hydrochloride (2.11 g, 11.0 mmol) and 1-hydroxybenzotriazole (1.49 g, 11.0 mmol) were suspended in 100 mL dichloromethane and stirred at room temperature for 30 min. Ethanolamine (0.67 g, 11.0 mmol) was added and the reaction was continued at room temperature for 8 hours. After completion of the reaction, 100 mL 1N diluted hydrochloric acid was added for phase separation. The organic phase was concentrated under reduced pressure. The residue was purified by column chromatography (petroleum ether/ethyl acetate=5:1 to 1:1) to give a white solid (2.89 g, yield: 89.5%), which is compound II-3.

Scheme 4:

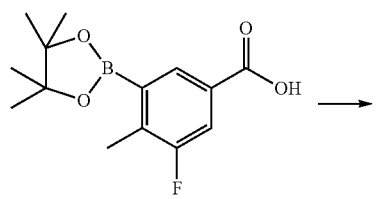

II-c

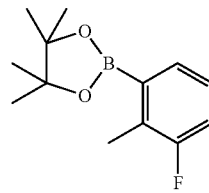

II-4

Step 1

Preparation of N-allyl-3-fluoro-4-methyl-5-(4,4,5,5-tetramethyl-1,3,2-dioxaborolan-2-yl)benzamide (Compound II-4)

Compound II-c (2.80 g, 10.0 mmol), 1-3(dimethylaminopropyl)-3-ethylcarbodiimide hydrochloride (2.11 g, 11.0 mmol) and 1-hydroxybenzotriazole (1.49 g, 1.0 mmol) were suspended in 100 mL dichloromethane and stirred at room temperature for 30 min. Allylamine (0.63 g, 11.0 mmol) was added and the reaction was continued at room temperature for 8 hours. After completion of the reaction, 100 mL 1N diluted hydrochloric acid was added for phase separation. The organic phase was concentrated under reduced pressure. The residue was purified by column chromatography (petroleum ether/ethyl acetate=5:1 to 1:1) to give a white solid (2.17 g, yield: 67.9%), which is compound II-4.

(2) Preparation of compound III: Compound III (i.e., Compound III-1~III-81) was prepared according to the following Method 1 to Method 6.

$$R_1\text{-}Q\text{-}X \qquad III$$

Method 1:

$R_1$ is

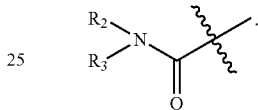

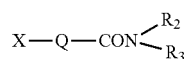

III-a

Compound III and compound III-a represent the same compound; the definition of $R_1$, Q and X and the used raw materials A and G were shown in the table below.

| Compound No. | Structure | X | $R_1$ | Q | A | G |
|---|---|---|---|---|---|---|
| III-1 | ![pyridazine with N-butyl-N-methyl carboxamide, Cl] | Cl | ![N-butyl-N-methyl amide] | ![chloropyridazine linker] | ![6-chloropyridazine-3-COOH] | ![HN-methyl-butyl] |
| III-2 | ![pyridazine with N-isopropyl-N-ethyl carboxamide, Cl] | Cl | ![N-isopropyl-N-ethyl amide] | | | ![HN-isopropyl-ethyl] |
| III-3 | ![pyridazine with N-isobutyl-N-methyl carboxamide, Cl] | Cl | ![N-isobutyl-N-methyl amide] | | | ![HN-isobutyl-methyl] |
| III-4 | ![pyridazine with N-cyclopentyl carboxamide, Cl] | Cl | ![N-cyclopentyl amide] | | | ![H2N-cyclopentyl] |

-continued
| Compound No. | Structure | X | R₁ | Q | A | G |
|---|---|---|---|---|---|---|
| III-5 | 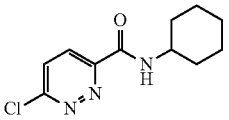 [SMILES: O=C(NC1CCCCC1)c1ccc(Cl)nn1] | Cl | 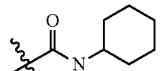 | | | 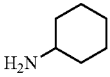 |
| III-6 | 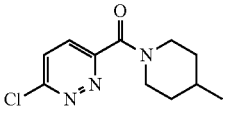 [SMILES: CC1CCN(C(=O)c2ccc(Cl)nn2)CC1] | Cl | 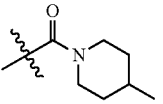 [SMILES: *C(=O)N1CCC(C)CC1] | | | 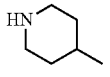 |
| III-7 | 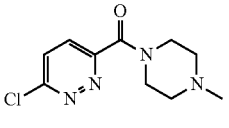 [SMILES: CN1CCN(C(=O)c2ccc(Cl)nn2)CC1] | Cl | 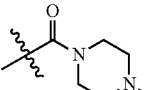 | | | 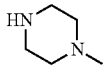 |
| III-8 | 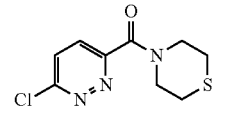 [SMILES: O=C(c1ccc(Cl)nn1)N1CCSCC1] | Cl | 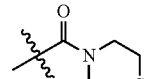 | | | 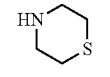 |
| III-9 | 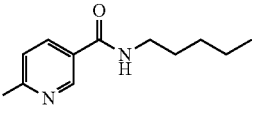 | Cl | 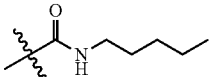 [SMILES: *C(=O)NCCCCC] | 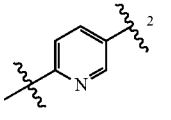 [SMILES: *c1ccc(*)nc1] | 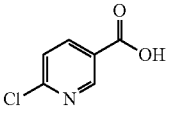 | 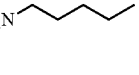 |
| III-10 | 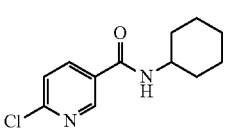 [SMILES: O=C(NC1CCCCC1)c1ccc(Cl)nc1] | Cl | 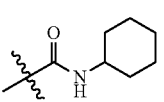 | | | 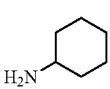 |
| III-11 | 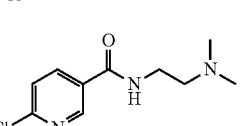 | Cl |  | | | 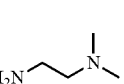 |
| III-12 | 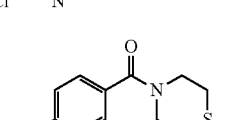 | Cl | 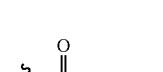 | | | 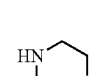 |
| III-13 | 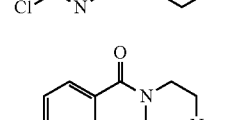 | Cl | 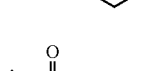 | | | 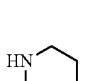 |
| III-14 | 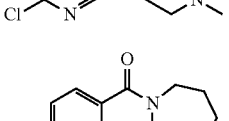 | Cl | 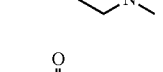 | | | 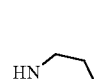 |
| III-15 | 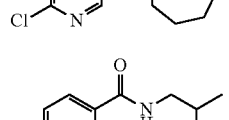 | Cl | 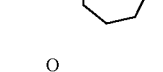 | 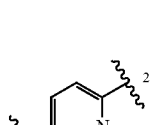 | 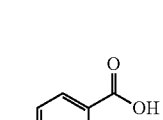 | 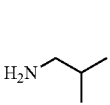 |
| III-16 | 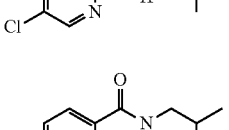 | Cl |  | | |  |

-continued

| Compound No. | Structure | X | R₁ | Q | A | G |
|---|---|---|---|---|---|---|
| III-17 | (5-bromopyridin-2-yl)-C(O)NH-cyclopentyl | Br | -C(O)NH-cyclopentyl | | 5-bromopyridine-2-carboxylic acid | H₂N-cyclopentyl |
| III-18 | (5-bromopyridin-2-yl)-C(O)N(CH₃)-cyclopentyl | Br | -C(O)N(CH₃)-cyclopentyl | | | HN(CH₃)-cyclopentyl |
| III-19 | (5-bromopyridin-2-yl)-C(O)NH-CH₂CH₂CH₂-Cl | Br | -C(O)NH-CH₂CH₂CH₂-Cl | | | H₂N-CH₂CH₂CH₂-Cl |
| III-20 | (4-iodophenyl)-C(O)N(propyl)₂ | I | -C(O)N(propyl)₂ | | | HN(propyl)₂ |
| III-21 | (4-iodophenyl)-C(O)N(iPr)₂ | I | -C(O)N(iPr)₂ | | | HN(iPr)₂ |
| III-22 | (4-iodophenyl)-C(O)NH-cyclopentyl | I | -C(O)NH-cyclopentyl | 1,4-phenylene | 4-iodobenzoic acid | H₂N-cyclopentyl |
| III-23 | (4-iodophenyl)-C(O)N(CH₃)-cyclopentyl | I | -C(O)N(CH₃)-cyclopentyl | | | HN(CH₃)-cyclopentyl |
| III-24 | (4-iodophenyl)-C(O)NH-cyclohexyl | I | -C(O)NH-cyclohexyl | | | H₂N-cyclohexyl |
| III-25 | (4-iodophenyl)-C(O)N(CH₃)-cyclohexyl | I | -C(O)N(CH₃)-cyclohexyl | | | HN(CH₃)-cyclohexyl |
| III-26 | (4-iodophenyl)-C(O)-(4-methylpiperidin-1-yl) | I | -C(O)-(4-methylpiperidin-1-yl) | | | 4-methylpiperidine |
| III-27 | (4-iodophenyl)-C(O)-(4-hydroxypiperidin-1-yl) | I | -C(O)-(4-hydroxypiperidin-1-yl) | | | 4-hydroxypiperidine |
| III-28 | (4-iodophenyl)-C(O)-(azepan-1-yl) | I | -C(O)-(azepan-1-yl) | | | azepane |

| Compound No. | Structure | X | R₁ | Q | A | G |
|---|---|---|---|---|---|---|
| III-29 | 4-iodobenzoyl thiomorpholine | I | C(=O)-thiomorpholine | | | thiomorpholine (HN-S) |
| III-30 | 2-F-4-I-benzamide N-isobutyl | I | C(=O)NH-isobutyl | | | H₂N-isobutyl |
| III-31 | 2-F-4-I-benzamide N-methyl-N-isobutyl | I | C(=O)N(Me)-isobutyl | | | HN(Me)-isobutyl |
| III-32 | 2-F-4-I-benzamide N-cyclopentyl | I | C(=O)NH-cyclopentyl | 2-F-phenyl | 2-F-4-I-benzoic acid | H₂N-cyclopentyl |
| III-33 | 2-F-4-I-benzamide N-methyl-N-cyclopentyl | I | C(=O)N(Me)-cyclopentyl | | | HN(Me)-cyclopentyl |
| III-34 | 2-F-4-I-benzoyl pyrrolidine | I | C(=O)-pyrrolidine | | | pyrrolidine |
| III-35 | 2-F-4-I-benzoyl 4-methylpiperidine | I | C(=O)-4-methylpiperidine | | | 4-methylpiperidine |
| III-36 | 2-F-4-I-benzoyl morpholine | I | C(=O)-morpholine | | | morpholine |
| III-37 | 2-OH-4-Br-benzamide N-methyl-N-isobutyl | Br | C(=O)N(Me)-isobutyl | 2-OH-phenyl | 2-OH-4-Br-benzoic acid | HN(Me)-isobutyl |
| III-38 | 2-OH-4-Br-benzamide N-isopropyl | Br | C(=O)NH-isopropyl | | | H₂N-isopropyl |
| III-39 | 2-OMe-4-Br-benzoyl 4-methylpiperidine | Br | C(=O)-4-methylpiperidine | 2-OMe-phenyl | 2-OMe-4-Br-benzoic acid | 4-methylpiperidine |

-continued

| Compound No. | Structure | X | R₁ | Q | A | G |
|---|---|---|---|---|---|---|
| III-40 | (2-methoxy-4-bromophenyl)(pyrrolidin-1-yl)methanone | Br | pyrrolidin-1-yl carbonyl | | | pyrrolidine (HN) |
| III-44 | N-isobutyl-4-iodo-2-methylbenzamide | I | N-isobutyl carbamoyl | 2-methyl-1,4-phenylene | 4-iodo-2-methylbenzoic acid | isobutylamine (H₂N) |
| III-45 | (4-iodo-2-methylphenyl)(piperazin-1-yl)methanone | I | piperazin-1-yl carbonyl | | | piperazine (HN-NH) |
| III-46 | (4-iodo-2-methylphenyl)(morpholin-4-yl)methanone | I | morpholin-4-yl carbonyl | | | morpholine (HN-O) |
| III-55 | (5-chlorothiophen-2-yl)(piperidin-1-yl)methanone | Cl | piperidin-1-yl carbonyl | 2,5-thienylene | 5-chlorothiophene-2-carboxylic acid | piperidine (HN) |
| III-56 | (5-chlorothiophen-2-yl)(4-methylpiperidin-1-yl)methanone | Cl | 4-methylpiperidin-1-yl carbonyl | | | 4-methylpiperidine (HN) |
| III-57 | N-isobutyl-6-chloropyridazine-3-carboxamide | Cl | N-isobutyl carbamoyl | 3,6-pyridazinylene | 6-chloropyridazine-3-carboxylic acid | isobutylamine (H₂N) |
| III-58 | N-sec-butyl-6-chloropyridazine-3-carboxamide | Cl | N-sec-butyl carbamoyl | | | sec-butylamine (H₂N) |
| III-59 | N-neopentyl-6-chloropyridazine-3-carboxamide | Cl | N-neopentyl carbamoyl | | | neopentylamine (H₂N) |
| III-60 | N-isoamyl-6-chloropyridazine-3-carboxamide | Cl | N-isoamyl carbamoyl | | | isoamylamine (H₂N) |
| III-61 | N-(cyclopropylmethyl)-6-chloropyridazine-3-carboxamide | Cl | N-(cyclopropylmethyl) carbamoyl | | | cyclopropylmethylamine (H₂N) |

-continued

| Compound No. | Structure | X | R₁ | Q | A | G |
|---|---|---|---|---|---|---|
| III-62 | 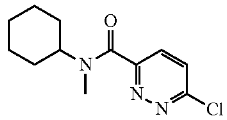 | Cl | | | | |
| III-63 | 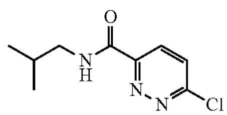 | Cl | | | | |
| III-64 | 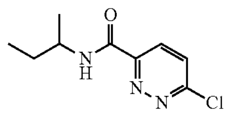 | Cl | | | | |
| III-65 | 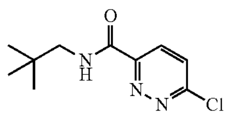 | Cl | | | | |
| III-66 | 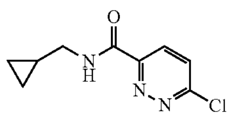 [SMILES: O=C(NCC1CC1)c1ccc(Cl)nn1] | Cl | | | | |
| III-67 | 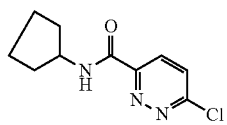 [SMILES: O=C(NC1CCCC1)c1ccc(Cl)nn1] | Cl | | | | |
| III-68 | 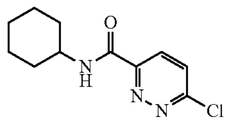 [SMILES: O=C(NC1CCCCC1)c1ccc(Cl)nn1] | Cl | | | | |
| III-69 | 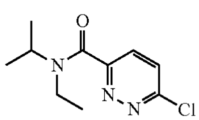 | Cl | | | | |
| III-70 | 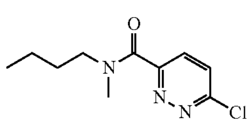 | Cl | | | | |
| III-71 | 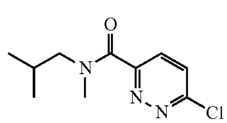 | Cl | | | | |
| III-73 | 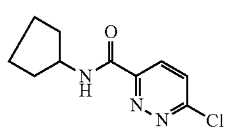 [SMILES: O=C(NC1CCCC1)c1ccc(Cl)nn1] | Cl | | | | |
| III-74 | 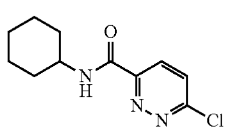 [SMILES: O=C(NC1CCCCC1)c1ccc(Cl)nn1] | Cl | | | | |

-continued

| Compound No. | Structure | X | R₁ | Q | A | G |
|---|---|---|---|---|---|---|
| III-75 | (pyridazine-C(O)N(iPr)(Et), Cl) | Cl | N(iPr)(Et)C(O)- | | | HN(iPr)(Et) |
| III-76 | (pyridazine-C(O)N(Bu)(Me), Cl) | Cl | N(Bu)(Me)C(O)- | | | HN(Bu)(Me) |
| III-77 | (pyridazine-C(O)N(iBu)(Me), Cl) | Cl | N(iBu)(Me)C(O)- | | | HN(iBu)(Me) |
| III-79 | (pyridazine-C(O)NH-cyclopentyl, Cl) | Cl | cyclopentyl-NHC(O)- | | | H₂N-cyclopentyl |
| III-80 | (pyridazine-C(O)NH-cyclohexyl, Cl) | Cl | cyclohexyl-NHC(O)- | | | H₂N-cyclohexyl |
| III-72 | (pyridine-C(O)NH-tBuCH₂, Cl) | Cl | tBuCH₂-NHC(O)- | 2,5-pyridyl | 6-chloronicotinic acid | H₂N-CH₂-tBu |
| III-78 | (pyridine-C(O)NH-neopentyl, Cl) | Cl | neopentyl-NHC(O)- | | | H₂N-CH₂-tBu |
| III-81 | (pyridine-C(O)NH-neopentyl, Cl) | Cl | neopentyl-NHC(O)- | | | H₂N-CH₂-tBu |

Preparation Method:

Compound A (e.g., 6.3 mmol) was added into thionyl chloride (e.g., 5 mL) and refluxed for 6 hours. The excess of thionyl chloride was evaporated under reduced pressure to obtain compound B, thionyl chloride (e.g., 30 mL) was added thereinto and the resulting product was used for the subsequent reaction.

Compound G (e.g., 6.8 mmol) was dissolved in dichloromethane (e.g., 30 mL), the above compound B in dichloromethane was added dropwise at 0-5° C. After completion of dropping, the reaction was carried out at room temperature for 1 hour. After completion of the reaction, the organic phase was washed with 5% hydrochloric acid (e.g., 50 mL) and 5% sodium hydroxide solution (e.g., 50 mL), dried and then concentrated to obtain compound III, the yield was >90%.

Method 2:

$R_1$ is

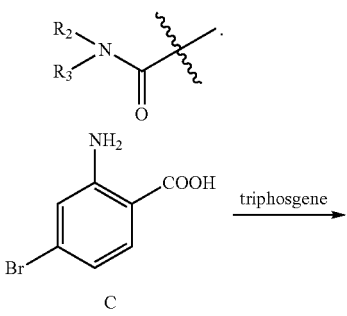

-continued

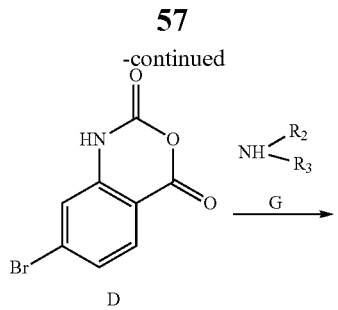

D

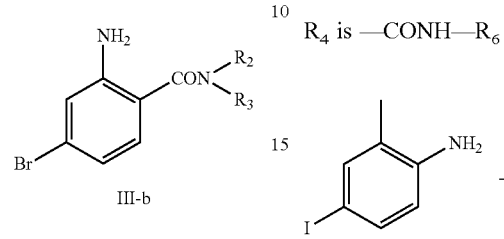

III-b

The definition of $R_1$, Q and X and the used raw material G were shown in the table below.

Method 3:

$R_1$ is

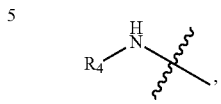

$R_4$ is —CONH—$R_6$

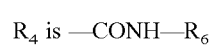

E

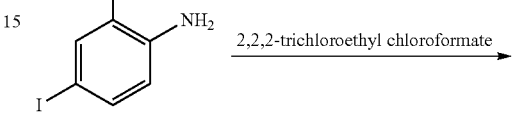

| Compound No. | Structure | X | $R_1$ | Q | G |
|---|---|---|---|---|---|
| III-41 | 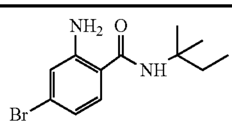 | Br | | | |
| III-42 | 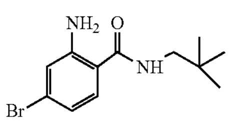 [SMILES: CC(C)(C)CNC(=O)c1ccc(Br)cc1N] | Br | |  | |
| III-43 | 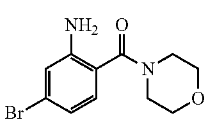 [SMILES: Nc1cc(Br)ccc1C(=O)N1CCOCC1] | Br | |  | |

Preparation Method:

Compound C (e.g., 4.6 mmol) and triphosgene (e.g., 4.6 mmol) were added in tetrahydrofuran (e.g., 30 mL), heated to reflux for 4 hours and cooled to the room temperature. 5% sodium hydroxide solution (e.g., 50 mL) and ethyl acetate (e.g., 30 mL) were added for phase separation. The organic phase was dried and concentrated under reduced pressure to obtain compound D.

Compound D (e.g., 4.1 mmol), 4-dimethylaminopyridine (e.g., 0.41 mmol) and compound G (e.g., 6.2 mmol) were dissolved in DMF (e.g., 30 mL) and reacted at room temperature for 6 hours. Water (e.g., 50 mL) and ethyl acetate (e.g., 30 mL) were added for phase separation. The organic phase was dried and concentrated to obtain compound III (the yield was about 80%).

-continued

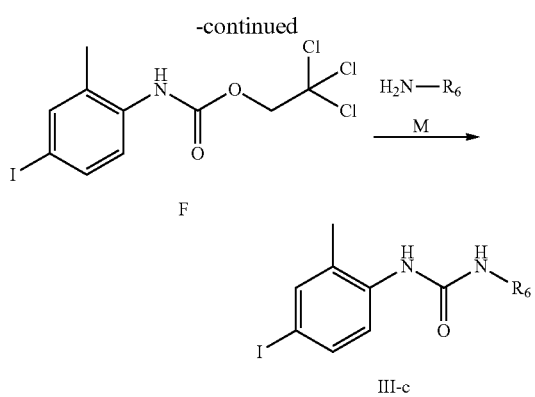

F

III-c

The definition of $R_1$, Q and X and the used raw material G were shown in the table below.

| Compound No | Structure | X | R1 | Q | M |
|---|---|---|---|---|---|
| III-49 | ![structure] | I | ![R1] | ![Q] | H₂N-iBu |
| III-50 | ![structure] | I | ![R1] | ![Q] | H₂N-cyclopentyl |

Preparation Method:

Compound E (e.g., 4.3 mmol) was added in ethyl acetate (e.g., 30 mL), water (e.g., 30 mL) and sodium hydroxide (e.g., 4.8 mmol) were added and the resulting product was used for the subsequent reaction.

2,2,2-trichloroethyl chloroformate (e.g., 4.7 mmol) was added dropwise to the above solution at 0-5° C. After completion of dropping, the reaction was carried out at room temperature for 1 hour. The organic phase was separated, dried and concentrated under reduced pressure to obtain compound F, the yield was >95%.

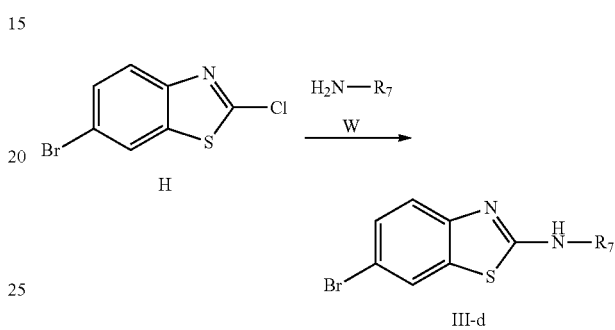

The definition of $R_1$, X and Q and the used raw material W were shown in the table below.

| Compound No. | Structure | X | $R_1$ | Q | W |
|---|---|---|---|---|---|
| III-51 | ![structure] | Br | ![R1] | ![Q] | H₂N-iBu |
| III-52 | ![structure] | Br | ![R1] | | H₂N-nBu |
| III-53 | ![structure] | Br | ![R1] | | H₂N-tBu |
| III-54 | ![structure] | Br | ![R1] | | H₂N-cyclopentyl |

Compound F (e.g., 3.0 mmol), compound M (e.g., 6.0 mmol) and N,N-diisopropylethylamine (e.g., 6.0 mmol) were dissolved in dimethyl sulfoxide (e.g., 30 mL) and reacted at 80° C. for 10 hours. Water (e.g., 50 mL) and ethyl acetate (e.g., 50 mL) were added for phase separation, the organic phase was dried and concentrated under reduced pressure to obtain compound III.

Method 4:

$R_1$ is $H_2N-R_7$, $R_7$ is $C_{1-6}$ alkyl or 5-7 membered cycloalkyl.

Preparation Method:

Compound H (e.g., 3.0 mmol), compound W (e.g., 6.0 mmol) and N,N-diisopropylethylamine (e.g., 6.0 mmol) were added in dimethyl sulfoxide (e.g., 30 mL) and reacted at 80° C. for 10 hours. Water (e.g., 50 mL) and ethyl acetate (e.g., 50 ml) were added for phase separation, the organic phase was dried and concentrated under reduced pressure to obtain compound II.

Method 5: Preparation of Compound III-47

| Compound No. | Structure | X | R₁ | Q |
|---|---|---|---|---|
| III-47 | ![structure] | I | ![structure] | ![structure] |

Preparation Method:

Cyclohexanecarboxylic acid (9.3 mmol) was suspended in thionyl chloride (5 mL) and refluxed at 80° C. for 6 hours. The excess of thionyl chloride was evaporated under reduced pressure to obtain a pale yellow solid, dichloromethane (30 mL) was added thereinto and the resulting product was used for the subsequent reaction.

2-fluoro-4-iodoaniline (8.4 mmol) was dissolved in dichloromethane (30 mL), the above acyl chloride in dichloromethane was added dropwise at 0-5° C. After completion of dropping, the reaction was carried out at room temperature for 1 hour. After completion of the reaction, the organic phase was washed with 5% hydrochloric acid (50 mL) and 5% sodium hydroxide solution (50 mL), dried and then concentrated to give a pale yellow solid (2.9 g, yield: 99.5%), which is compound III-47.

Method 6: Preparation of Compound III-48

| Compound No. | structure | X | R₁ | Q |
|---|---|---|---|---|
| III-47 | ![structure] | I | ![structure] | ![structure] |

Preparation Method:

N-(2-fluoro-4-iodophenyl)cyclohexylformamide (5.0 mmol) and sodium borohydride (15.0 mmol) were suspended in tetrahydrofuran (30 mL), boron trifluoride diethyl etherate solution (20.0 mmol) was added dropwise at 0-5° C. After completion of dropping, the reaction was carried out at room temperature for 1 hour, and then the temperature was went up to 40~50° C. and reacted at this temperature for 2~3 hours. Water and hydrochloric acid were slowly added, the pH was adjusted to 2~3, and stirred for 30 minutes. Ethyl acetate (50 mL) was added for phase separation. The organic phase was dried and concentrated under reduced pressure to obtain a pale yellow solid (1.3 g, the yield was 78.0%), which is compound III-48.

Examples 1-56: Preparation of Compounds
I-1~I-56

Synthetic Route:

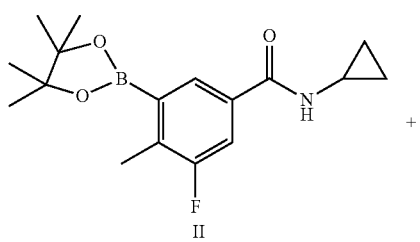

-continued

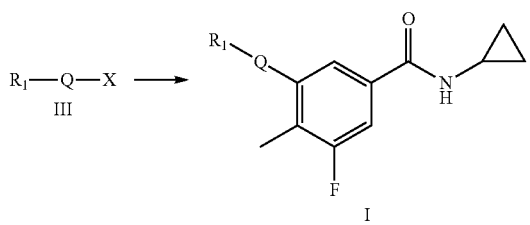

Wherein, the definitions of R₁, Q and X were shown in the table below.

Preparation Method:

Compound III (e.g., 1.5 mmol) and compound II (e.g., 1.5 mmol) were added in isopropyl alcohol (e.g., 30 mL), 1M aqueous sodium bicarbonate (e.g., 1.9 mL) and Pd(PPh₃)₄ (e.g., 0.016 mmol) were added and refluxed at 90° C. for 10 hours. After completion of the reaction, the reaction solution was concentrated under reduced pressure. The residue was purified by column chromatography (petroleum ether:ethyl acetate=5:1~1:1) to give the target compound.

| Example | Compound | Chemical Name | Structure | X | R₁ | Q |
|---|---|---|---|---|---|---|
| 1 | I-1 | 6-(5-(cyclopropylcarbamoyl)-3-fluoro-2-methylphenyl)-N-butyl-N-methylpyridazin-3-carboxamide | 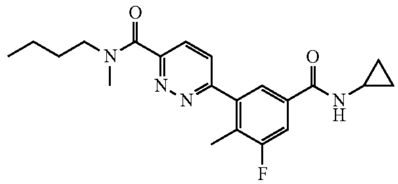 [SMILES: CCCCN(C)C(=O)c1ccc(-c2cc(C(=O)NC3CC3)cc(F)c2C)nn1] | Cl | | |
| 2 | I-2 | 6-(5-(cyclopropylcarbamoyl)-3-fluoro-2-methylphenyl)-N-ethyl-N-isopropylpyridazin-3-carboxamide | 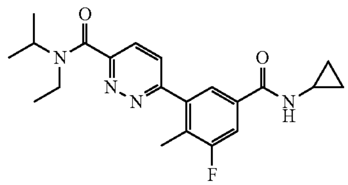 [SMILES: CCN(C(=O)c1ccc(-c2cc(C(=O)NC3CC3)cc(F)c2C)nn1)C(C)C] | Cl | | |
| 3 | I-3 | 6-(5-cyclopropylcarbamoyl)-3-fluoro-2-methylphenyl)-N-isobutyl-N-methylpyridazin-3-carboxamide | 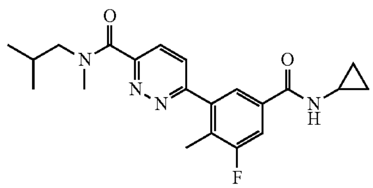 [SMILES: Cc1c(F)cc(C(=O)NC2CC2)cc1-c1ccc(C(=O)N(C)CC(C)C)nn1] | Cl | | |
| 4 | I-4 | N-cyclopentyl-6-(5-(cyclopropylcarbamoyl)-3-fluoro-2-ethylphenyl)pyridazin-3-carboxamide | 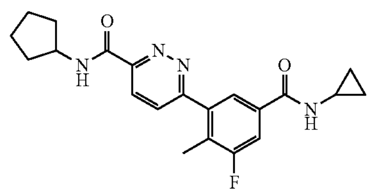 [SMILES: Cc1c(F)cc(C(=O)NC2CC2)cc1-c1ccc(C(=O)NC2CCCC2)nn1] | Cl | | |
| 5 | I-5 | N-cyclohexyl-6-(5-(cyclopropylcarbamoyl)-3-fluoro-2-methylphenyl)pyridazin-3-carboxamide | 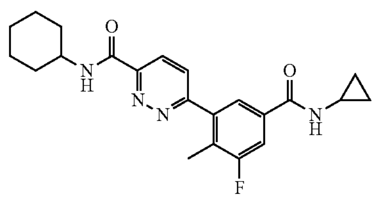 [SMILES: Cc1c(F)cc(C(=O)NC2CC2)cc1-c1ccc(C(=O)NC2CCCCC2)nn1] | Cl | | |
| 6 | I-6 | N-cyclopropyl-3-fluoro-4-methyl-5-(6-(4-methylpiperidin-1-carbonyl)pyridazin-3-yl)benzamide | 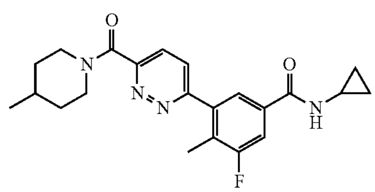 | Cl | | |
| 7 | I-7 | N-cyclopropyl-3-fluoro-4-methyl-5-(6-(4-methylpiperazin-1-carbonyl)pyridazin-3-yl)benzamide | 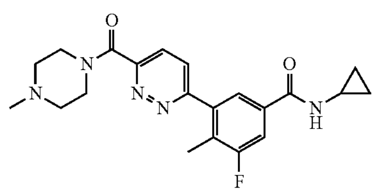 [SMILES: Cc1c(F)cc(C(=O)NC2CC2)cc1-c1ccc(C(=O)N2CCN(C)CC2)nn1] | Cl | | |
| 8 | I-8 | N-cyclopropyl-3-fluoro-4-methyl-5-(6-(thiomorpholin-4-carbonyl)pyridazin-3-yl)benzamide | 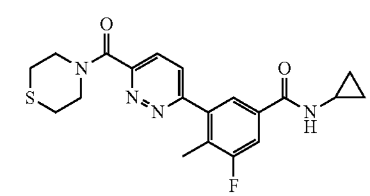 [SMILES: Cc1c(F)cc(C(=O)NC2CC2)cc1-c1ccc(C(=O)N2CCSCC2)nn1] | Cl | | |

-continued

| Example | Compound | Chemical Name | Structure | X | R₁ | Q |
|---|---|---|---|---|---|---|
| 9 | I-9 | 6-(5-(cyclopropylcarbamoyl)-3-fluoro-2-methylphenyl)-N-pentylnicotinamide | 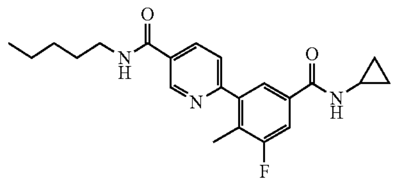 [SMILES: CCCCCNC(=O)c1ccc(-c2cc(C(=O)NC3CC3)cc(F)c2C)nc1] | Cl | pentylamide | pyridine (1,2) |
| 10 | I-10 | N-cyclohexyl-6-(5-(cyclopropylcarbamoyl)-3-fluoro-2-methylphenyl)nicotinamide | 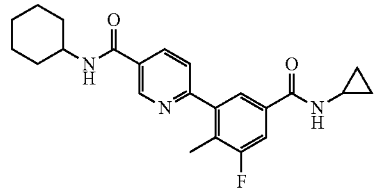 [SMILES: Cc1c(F)cc(C(=O)NC2CC2)cc1-c1ccc(C(=O)NC2CCCCC2)cn1] | Cl | cyclohexylamide | pyridine (1,2) |
| 11 | I-11 | 6-(5-(cyclopropylcarbamoyl)-3-fluoro-2-methylphenyl)-N-(2-(dimethylamino)ethyl)nicotinamide | 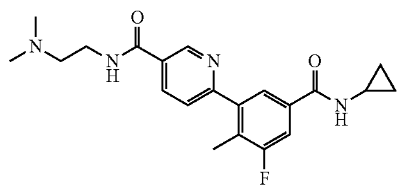 [SMILES: Cc1c(F)cc(C(=O)NC2CC2)cc1-c1ccc(C(=O)NCCN(C)C)cn1] | Cl | N-(2-dimethylaminoethyl)amide | pyridine (1,2) |
| 12 | I-12 | N-cyclopropyl-3-fluoro-4-methyl-5-(5-(thiomorpholin-4-carbonyl)pyridin-2-yl)benzamide | 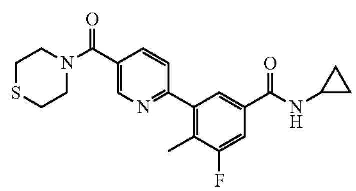 [SMILES: Cc1c(F)cc(C(=O)NC2CC2)cc1-c1ccc(C(=O)N2CCSCC2)cn1] | Cl | thiomorpholinyl carbonyl | pyridine (1,2) |
| 13 | I-13 | N-cyclopropyl-3-fluoro-4-methyl-5-(5-(4-methylpiperazin-1-carbonyl)pyridin-2-yl)benzamide | 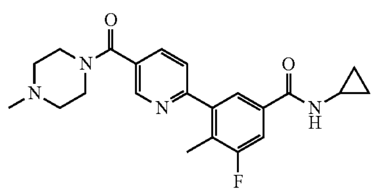 [SMILES: Cc1c(F)cc(C(=O)NC2CC2)cc1-c1ccc(C(=O)N2CCN(C)CC2)cn1] | Cl | 4-methylpiperazinyl carbonyl | pyridine (1,2) |
| 14 | I-14 | 3-(5-azepane-1-carbonyl)pyridin-2-yl)-N-cyclopropyl-5-fluoro-4-methylbenzamide | 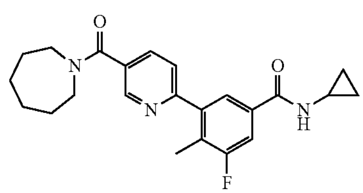 [SMILES: Cc1c(F)cc(C(=O)NC2CC2)cc1-c1ccc(C(=O)N2CCCCCC2)cn1] | Cl | azepanyl carbonyl | pyridine (1,2) |
| 15 | I-15 | 5-(5-(cyclopropylcarbamoyl)-3-fluoro-2-methylphenyl)-N-isobutylpyridin-2-formamide | 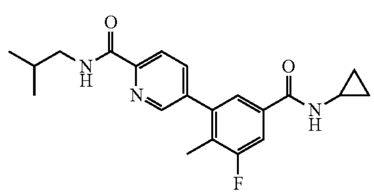 [SMILES: Cc1c(F)cc(C(=O)NC2CC2)cc1-c1ccc(C(=O)NCC(C)C)nc1] | Cl | N-isobutyl amide | pyridine (2,1) |
| 16 | I-16 | 5-(5-(cyclopropylcarbamoyl)-3-fluoro-2-methylphenyl)-N-isobutyl-N-methylpyridin-2-formamide | 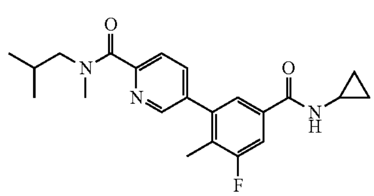 [SMILES: Cc1c(F)cc(C(=O)NC2CC2)cc1-c1ccc(C(=O)N(C)CC(C)C)nc1] | Cl | N-isobutyl-N-methyl amide | pyridine (2,1) |

| Example | Compound | Chemical Name | Structure | X | $R_1$ | Q |
|---|---|---|---|---|---|---|
| 17 | I-17 | N-cyclopentyl-5-(5-(cyclopropylcarbamoyl)-3-fluoro-2-methylphenyl)pyridin-2-foramamide | 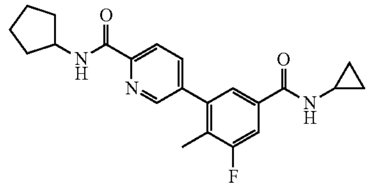 | Br | | |
| 18 | I-18 | N-cyclopentyl-5-(5-(cyclopropylcarbamoyl)-3-fluoro-2-methylphenyl)-N-methylpyridin-2-formamide | 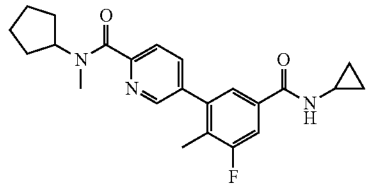 | Br | | |
| 19 | I-19 | N-(3-chloropropyl)-5-(5-(cyclopropylcarbamoyl)-3-fluoro-2-methylphenyl)pyridin-2-formamide | 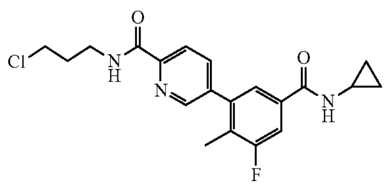 [SMILES: Cc1c(F)cc(C(=O)NC2CC2)cc1-c1ccc(C(=O)NCCCCl)nc1] | Br | | |
| 20 | I-20 | $N^3$-cyclopropyl-5-fluoro-6-methyl-$N^{4'},N^{4'}$-dipropyl-[1,1'-biphenyl]-3,4'-dicarboxamide | 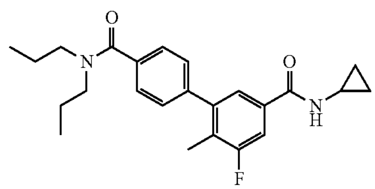 [SMILES: CCCN(CCC)C(=O)c1ccc(-c2cc(C(=O)NC3CC3)cc(F)c2C)cc1] | I | | |
| 21 | I-21 | $N^3$-cyclopropyl-5-fluoro-$N^{4'},N^{4'}$-diisopropyl-6-methyl-[1,1'-biphenyl]-3,4'-dicarboxamide | 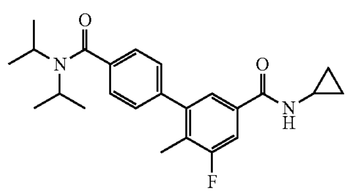 [SMILES: Cc1c(F)cc(C(=O)NC2CC2)cc1-c1ccc(C(=O)N(C(C)C)C(C)C)cc1] | I | | |
| 22 | I-22 | $N^{4'}$-cyclopentyl-$N^3$-cyclopropyl-5-fluoro-6-methyl-[1,1']-biphenyl]-3,4'-dicarboxamide | 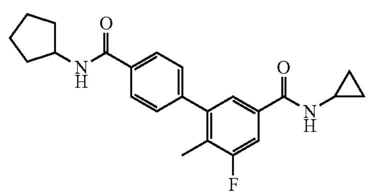 | I | | |
| 23 | I-23 | $N^{4'}$-cyclopentyl-$N^3$-cyclopropyl-5-fluoro-$N^{4'}$,6-dimethyl-[1,1'-biphenyl]-3,4'-dicarboxamide | 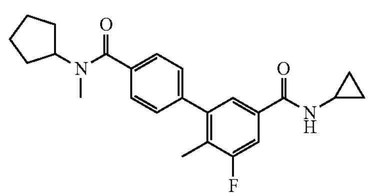 [SMILES: Cc1c(F)cc(C(=O)NC2CC2)cc1-c1ccc(C(=O)N(C)C2CCCC2)cc1] | I | | |
| 24 | I-24 | $N^{4'}$-cyclohexyl-$N^3$-cyclopropyl-5-fluoro-6-methyl-[1,1'-biphenyl]-3,4'-dicarboxamide | 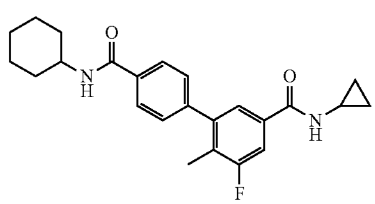 [SMILES: Cc1c(F)cc(C(=O)NC2CC2)cc1-c1ccc(C(=O)NC2CCCCC2)cc1] | I | | |

-continued

| Example | Compound | Chemical Name | Structure | X | R₁ | Q |
|---|---|---|---|---|---|---|
| 25 | I-25 | N⁴'-cyclohexyl-N³-cyclopropyl-5-fluoro-N⁴',6-dimethyl-[1,1'-biphenyl]-3,4'-dicarboxamide | 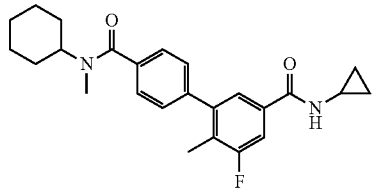 [SMILES: Cc1c(F)cc(C(=O)NC2CC2)cc1-c1ccc(C(=O)N(C)C2CCCCC2)cc1] | I | | |
| 26 | I-26 | N-cyclopropyl-5-fluoro-6-methyl-4'-(4-methylpiperidin-1-carbonyl)-[1,1'-biphenyl]-3-carboxamide | 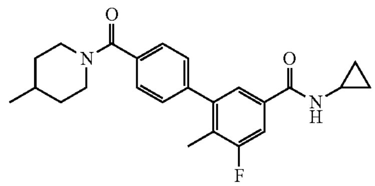 [SMILES: Cc1c(F)cc(C(=O)NC2CC2)cc1-c1ccc(C(=O)N2CCC(C)CC2)cc1] | I | | |
| 27 | I-27 | N-cyclopropyl-5-fluoro-4'-(4-hydroxypiperidin-1-carbonyl)-6-methyl-[1,1'-biphenyl]-3-carboxamide | 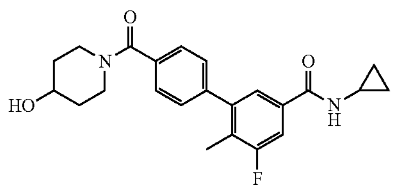 [SMILES: Cc1c(F)cc(C(=O)NC2CC2)cc1-c1ccc(C(=O)N2CCC(O)CC2)cc1] | I | | |
| 28 | I-28 | 4'-(azepane-1-carbonyl)-N-cyclopropyl-5-fluoro-6-methyl-[1,1'-biphenyl]-3-carboxamide | 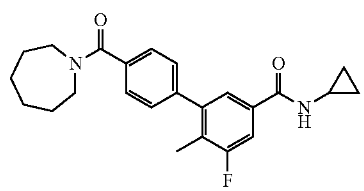 [SMILES: Cc1c(F)cc(C(=O)NC2CC2)cc1-c1ccc(C(=O)N2CCCCCC2)cc1] | I | | |
| 29 | I-29 | N-cyclopropyl-5-fluoro-6-methyl-4'-(thiomorpholin-4-carbonyl)-[1,1'-biphenyl]-3-carboxamide | 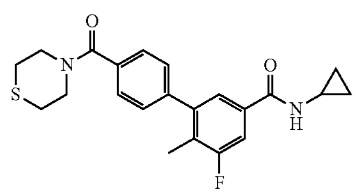 [SMILES: Cc1c(F)cc(C(=O)NC2CC2)cc1-c1ccc(C(=O)N2CCSCC2)cc1] | I | | |
| 30 | I-30 | N³-cyclopropyl-3',5-difluoro-N⁴'-isobutyl-6-methyl-[1,1'-biphenyl]-3,4'-dicarboxamide | 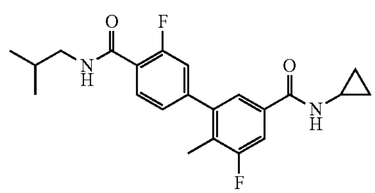 [SMILES: Cc1c(F)cc(C(=O)NC2CC2)cc1-c1ccc(C(=O)NCC(C)C)c(F)c1] | I | | |
| 31 | I-31 | N³-cyclopropyl-3',5-difluoro-N⁴'-isobutyl-N⁴',6-dimethyl-[1,1'-biphenyl]-3,4'-dicarboxamide | 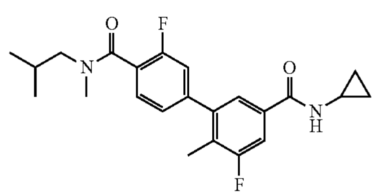 | I | | |
| 32 | I-32 | N⁴'-cyclopentyl-N³-cyclopropyl-3',5-difluoro-6-methyl-[1,1'-biphenyl]-3,4'-dicarboxamide | 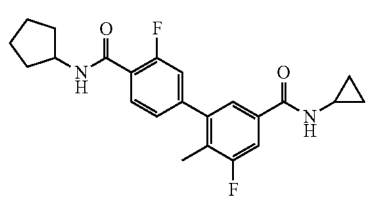 | I | | |

-continued

| Example | Compound | Chemical Name | Structure | X | R₁ | Q |
|---|---|---|---|---|---|---|
| 33 | I-33 | N⁴'-cyclopentyl-N³-cyclopropyl-3',5-difluoro-N⁴',6-dimethyl-[1,1'-biphenyl]-3,4'-dicarboxamide | 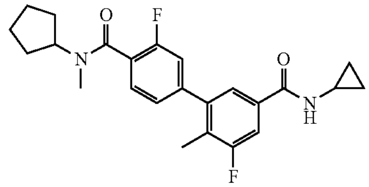 [SMILES: Cc1c(F)cc(C(=O)NC2CC2)cc1-c1ccc(C(=O)N(C)C2CCCC2)c(F)c1] | I | | |
| 34 | I-34 | N-cyclopropyl-3',5-difluoro-6-methyl-4'-(pyrrolidin-1-carbonyl)-[1,1'-biphenyl]-3-carboxamide | 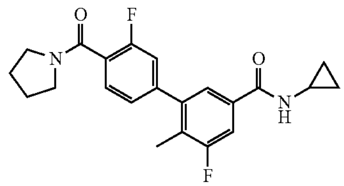 [SMILES: Cc1c(F)cc(C(=O)NC2CC2)cc1-c1ccc(C(=O)N2CCCC2)c(F)c1] | I | | |
| 35 | I-35 | N-cyclopropyl-3',5-difluoro-6-methyl-4'-(4-methylpiperidin-1-carbonyl)-[1,1'-biphenyl]-3-carboxamide | 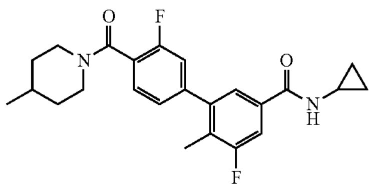 [SMILES: Cc1c(F)cc(C(=O)NC2CC2)cc1-c1ccc(C(=O)N2CCC(C)CC2)c(F)c1] | I | | |
| 36 | I-36 | N-cyclopropyl-3',5-difluoro-6-methyl-4'-(morpholin-4-carbonyl)-[1,1'-biphenyl]-3-carboxamide | 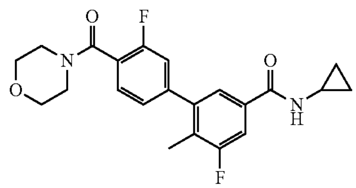 [SMILES: Cc1c(F)cc(C(=O)NC2CC2)cc1-c1ccc(C(=O)N2CCOCC2)c(F)c1] | I | | |
| 37 | I-37 | N³-cyclopropyl-5-fluoro-3'-hydroxy-N⁴'-isobutyl-N⁴',6-dimethyl-[1,1'-biphenyl]-3,4'-dicarboxamide | 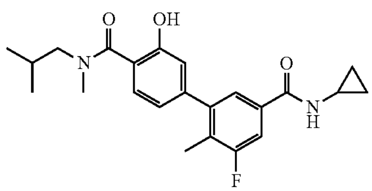 [SMILES: Cc1c(F)cc(C(=O)NC2CC2)cc1-c1ccc(C(=O)N(C)CC(C)C)c(O)c1] | Br | | |
| 38 | I-38 | N³-cyclopropyl-5-fluoro-3'-hydroxy-N⁴'-isopropyl-6-methyl-[1,1'-biphenyl]-3,4'-dicarboxamide | 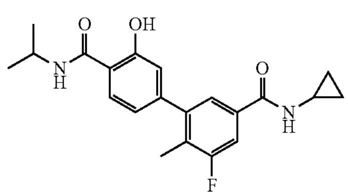 [SMILES: Cc1c(F)cc(C(=O)NC2CC2)cc1-c1ccc(C(=O)NC(C)C)c(O)c1] | Br | | |
| 39 | I-39 | N-cyclopropyl-5-fluoro-3'-methoxy-6-methyl-4'-(4-methylpiperidin-1-carbonyl)-[1,1'-biphenyl]-3-carboxamide | 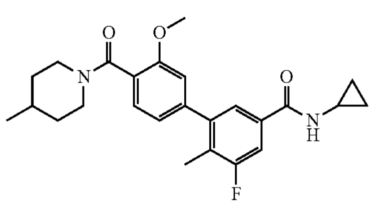 [SMILES: COc1cc(-c2cc(C(=O)NC3CC3)cc(F)c2C)ccc1C(=O)N1CCC(C)CC1] | Br | | |
| 40 | I-40 | N-cyclopropyl-5-fluoro-3'-methoxy-6-methyl-4'-(pyrrolidin-1-carbonyl)-[1,1'-biphenyl]-3-carboxamide | 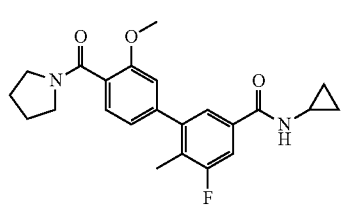 [SMILES: COc1cc(-c2cc(C(=O)NC3CC3)cc(F)c2C)ccc1C(=O)N1CCCC1] | Br | | |

-continued

| Example | Compound | Chemical Name | Structure | X | R₁ | Q |
|---|---|---|---|---|---|---|
| 41 | I-41 | 3'-amino-N³-cyclopropyl-5-fluoro-6-methyl-N⁴'-(tertpentyl)-[1,1'-biphenyl]-3,4'-dicarboxamide | 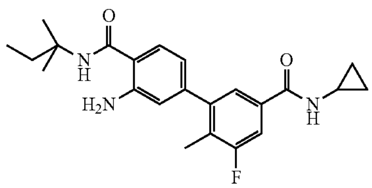 [SMILES: CCC(C)(C)NC(=O)c1ccc(-c2cc(C(=O)NC3CC3)cc(F)c2C)cc1N] | Br | | |
| 42 | I-42 | 3'-amino-N³-cyclopropyl-5-fluoro-6-methyl-N⁴'-neopentyl-[1,1'-biphenyl]-3,4'-dicarboxamide | 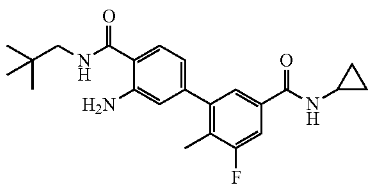 [SMILES: Cc1c(F)cc(C(=O)NC2CC2)cc1-c1ccc(C(=O)NCC(C)(C)C)c(N)c1] | Br | | |
| 43 | I-43 | 3'-amino-N-cyclopropyl-5-fluoro-6-methyl-4'-(morpholin-4-carbonyl)-[1,1'-biphenyl]-3-carboxamide | 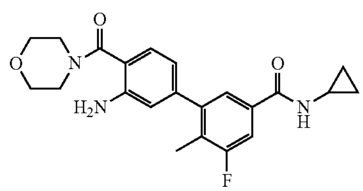 [SMILES: Cc1c(F)cc(C(=O)NC2CC2)cc1-c1ccc(C(=O)N2CCOCC2)c(N)c1] | Br | | |
| 44 | I-44 | N³-cyclopropyl-5-fluoro-N⁴'-isobutyl-3',6-dimethyl-[1,1'-biphenyl]-3,4'-dicarboxamide | 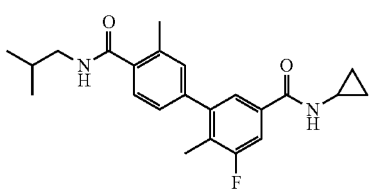 [SMILES: Cc1cc(-c2cc(C(=O)NC3CC3)cc(F)c2C)ccc1C(=O)NCC(C)C] | I | | |
| 45 | I-45 | N-cyclopropyl-5-fluoro-3,6-dimethyl-4'-(piperazin-1-carbon)-[1,1'-biphenyl]-3-carboxamide | 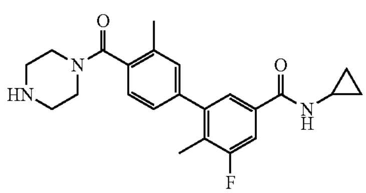 [SMILES: Cc1cc(-c2cc(C(=O)NC3CC3)cc(F)c2C)ccc1C(=O)N1CCNCC1] | I | | |
| 46 | I-46 | N-cyclopropyl-5-fluoro-3',6-dimethyl-4'-(morpholin-4-carbonyl)-[1,1'-biphenyl]-3-carboxamide | 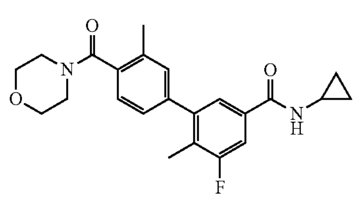 [SMILES: Cc1cc(-c2cc(C(=O)NC3CC3)cc(F)c2C)ccc1C(=O)N1CCOCC1] | I | | |
| 47 | I-47 | 4'-(cyclohexanecarboxamido)-N-cyclopropyl-3',5-difluoro-6-methyl-[1,1'-biphenyl]-3-carboxamide | 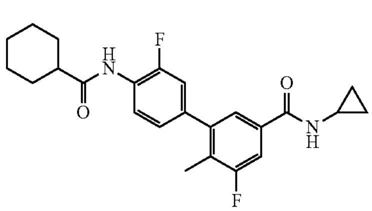 [SMILES: Cc1c(F)cc(C(=O)NC2CC2)cc1-c1ccc(NC(=O)C2CCCCC2)c(F)c1] | I | | |

-continued

| Example | Compound | Chemical Name | Structure | X | R₁ | Q |
|---|---|---|---|---|---|---|
| 48 | I-48 | 4'-((cyclohexylmethyl)amino)-N-cyclopropyl-3',5-difluoro-6-methyl-[1,1'-biphenyl]-3-carboxamide | 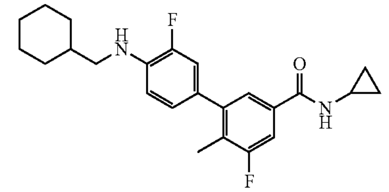 [SMILES: Cc1c(F)cc(C(=O)NC2CC2)cc1-c1ccc(NCC2CCCCC2)c(F)c1] | I | | |
| 49 | I-49 | N-cyclopropyl-5-fluoro-4'-(3-isobutylureido)-3',6-dimethyl-[1,1'-biphenyl]-3-carboxamide | 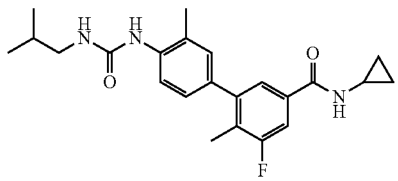 [SMILES: Cc1cc(-c2cc(C(=O)NC3CC3)cc(F)c2C)ccc1NC(=O)NCC(C)C] | I | | |
| 50 | I-50 | 4'-(3-cyclopentylureido)-N-cyclopropyl-5-fluoro-3',6-dimethyl-[1,1'-biphenyl]-3-carboxamide | 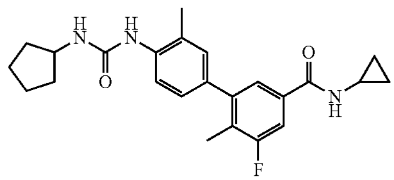 [SMILES: Cc1cc(-c2cc(C(=O)NC3CC3)cc(F)c2C)ccc1NC(=O)NC1CCCC1] | I | | |
| 51 | I-51 | N-cyclopropyl-3-fluoro-5-(2-(isobutylamino)benzo[d]thiazol-6-yl)-4-methylbenzamide | 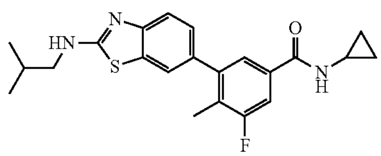 [SMILES: Cc1c(F)cc(C(=O)NC2CC2)cc1-c1ccc2nc(NCC(C)C)sc2c1] | Br | | |
| 52 | I-52 | 3-(2-(butylamino)benzo[d]thiazol-6-yl)-N-cyclopropyl-5-fluoro-4-methylbenzamide | 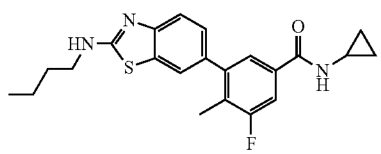 [SMILES: CCCCNc1nc2ccc(-c3cc(C(=O)NC4CC4)cc(F)c3C)cc2s1] | Br | | |
| 53 | I-53 | 3-(2-(tert-butylamino)benzo[d]thiazol-6-yl)-N-cyclopropyl-5-fluoro-4-methylbenzamide | 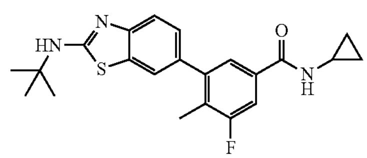 [SMILES: Cc1c(F)cc(C(=O)NC2CC2)cc1-c1ccc2nc(NC(C)(C)C)sc2c1] | Br | | |
| 54 | I-54 | 3-(2-(cyclopentylamino)benzo[d]thiazol-6-yl)-N-cyclopropyl-5-fluoro-4-methylbenzamide | 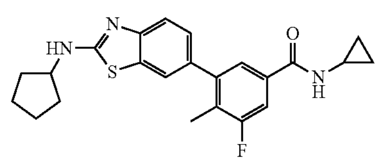 [SMILES: Cc1c(F)cc(C(=O)NC2CC2)cc1-c1ccc2nc(NC3CCCC3)sc2c1] | Br | | |
| 55 | I-55 | N-cyclopropyl-3-fluoro-4-methyl-5-(5-(piperidin-1-carbonyl)thiophen-2-yl)benzamide | 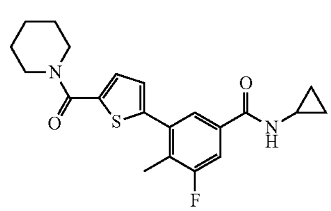 [SMILES: Cc1c(F)cc(C(=O)NC2CC2)cc1-c1ccc(C(=O)N2CCCCC2)s1] | Cl | | |

-continued

| Example | Compound | Chemical Name | Structure | X | R₁ | Q |
|---|---|---|---|---|---|---|
| 56 | I-56 | N-cyclopropyl-3-fluoro-4-methyl-5-(5-(4-methylpiperidin-1-carbonyl)thiophen-2-yl)benzamide | 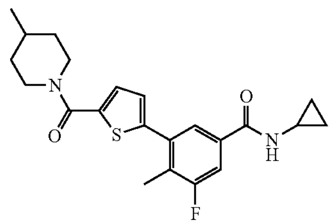 [SMILES: Cc1c(F)cc(C(=O)NC2CC2)cc1-c1ccc(C(=O)N2CCC(C)CC2)s1] | Cl | (4-methylpiperidin-1-yl)carbonyl | 2,5-thienyl |

The results of the physical characterization of the above compounds according to the present invention are shown in the table below.

| Example | Compound | Result | ¹H NMR(600 MHz, DMSO-d₆) | MS [M + H]⁺ |
|---|---|---|---|---|
| 1 | I-1 | Light yellow solid, with a yield of 19.1% | 0.573-0.590(m, 2H), 0.693-0.716(m, 2H), 0.741-0.976(m, 3H), 1.125-1.404(m, 2H), 1.565-1.645(m, 2H), 2.261-2.277(d, 3H), 2.857-2.876(m, 1H), 2.999-3.077(d, 3H), 3.318-3.345(m, 1H), 3.537-3.561(m, 1H), 7.755-7.773(d, 1H), 7.832(s, 1H), 7.983-8.004(m, 1H), 8.065-8.080(m, 1H), 8.583(s, 1H). | 385.2 |
| 2 | I-2 | Light yellow solid, with a yield of 17.3% | 0.572-0.583(m, 2H), 0.693-0.716(m, 2H), 1.183-1.136 (m, 9H), 2.267-2.283(m, 3H), 2.865-2.872(m, 1H), 3.449-3.460(m, 2H), 3.868-3.887(m, 1H), 7.749-7.769(m, 1H), 7.832-7.841 (m, 1H), 7.973-7.996(m, 1H), 8.055-8.072(m, 1H), 8.573(s, 1H). | 385.2 |
| 3 | I-3 | Light yellow solid, with a yield of 19.1% | 0.565-0.590(m, 2H), 0.694-0.750(m, 5H), 0.960-0.971(d, 3H), 1.914-2.132(m, 1H), 2.265-2.281(m, 3H), 2.846-2.882(m, 1H), 2.998-3.083(d, 3H), 3.227-3.391(m, 2H), 7.756-7.774(d, 1H), 7.834-7.847(m, 1H), 7.976-7.997(dd, 1H), 8.061-8.080(dd, 1H) 8.573(s, 1H). | 385.1 |
| 4 | I-4 | White solid, with a yield of 40.1% | 0.564-0.589(m, 2H), 0.698-0.729(m, 2H), 1.563-1.595(m, 2H), 1.649-1.751(m, 4H), 1.901-1.933(m, 2H), 2.275-2.278(d, 3H), 2.851-2.893(m, 1H), 4.317-4.379(m, 1H), 7.770-7.832(m, 2H), 8.127-8.142(d, 1H), 8.306-8.320(d, 1H), 8.580-8.587(d, 1H), 9.149-9.162(d, 1H). | 383.1 |
| 5 | I-5 | While solid, with a yield of 42.5% | 0.562-0.588(m, 2H), 0.697-0.729(m, 2H), 1.141-1.176(m, 1H), 1.307-1.371(m, 2H), 1.464-1.529(m, 2H), 1.611-1.632(m, 1H), 1.741-1.763(m, 2H), 1.828-1.845(m, 2H), 2.274-2.277(d, 3H), 2.849-2.880(m, 1H), 3.870-3.894(m, 1H), 7.769-7.787(d, 1H), 7.830(s, 1H), 8.126-8.140(d, 1H), 8.310-8.325(d, 1H), 8.579-8.586(d, 1H), 9.058-9.072(d, 1H). | 397.3 |
| 6 | I-6 | White solid, with a yield of 55.8% | 0.567-0.593(m, 2H), 0.694-0.726(m, 2H), 0.945-0.956(d, 3H), 1.161-1.181(m, 2H), 1.603-1.785(m, 3H), 2.280-2.283(d, 3H), 2.859-2.902(m, 2H), 3.078-3.146(m, 1H), 3.655-3.677(d, 1H), 4.524-4.545(d, 1H), 7.756-7.773(d, 1H), 7.841(s, 1H), 7.988-8.003(d, 1H), 8.065-8.079(d, 1H), 8.574(s, 1H). | 397.3 |
| 7 | I-7 | Gray solid, with a yield of 18.5% | 0.565-0.587(m, 2H), 0.699-0.723(m, 2H), 2.228(s, 3H), 2.277-2.280(d, 3H), 2.339-2.354(m, 2H), 2.434-2.450(m, 2H), 2.851-2.882(m, 1H), 3.459-3.475(m, 2H), 3.731(m, 2H), 7.753-7.772(dd, 1H), 7.833-7.835(d, 1H), 8.006-8.021(d, 1H), 8.073-8.087(d, 1H), 8.568-8.575(d, 1H). | 398.2 |
| 8 | I-8 | White solid, with a yield of 47.6% | 0.575-0.587(m, 2H), 0.690-0.721(m, 2H), 2.277(s, 3H), 2.684-2.700(m, 2H), 2.755-2.771(m, 2H), 2.850-2.881(m, 1H), 3.683-3.699(m, 2H), 3.976-3.992(m, 2H), 7.752-7.769(d, 1H), 7.835(s, 1H), 8.028-8.042(d, 1H), 8.084-8.098(d, 1H), 8.573-8.579(d, 1H). | 401.1 |
| 9 | I-9 | White-like solid, with a yield of 40.7% | 0.584(m, 2H), 0.682-0.713(m, 2H), 0.877-0.900(t, 3H), 1.320-1.325(m, 4H), 1.545-1.568(m, 2H), 2.258(s, 3H), 2.843-2.872(m, 1H), 3.281-3.303(t, 2H), 7.677-7.721(m, 2H), 7.762(s, 1H), 8.300-8.316(dd, 1H), 8.545-8.552(d, 1H), 8.704-8.722(m, 1H), 9.099-9.102(d, 1H). | 384.2 |
| 10 | I-10 | White solid, with a yield of 26.6% | 0.556-0.580(m, 2H), 0.692-0.716(m, 2H), 1.135-1.186(m, 1H), 1.331-1.349(m, 4H), 1.611-1.632(m, 1H), 1.752-1.760(m, 2H), 1.858-1.871(m, 2H), 2.253-2.256(d, 3H), 2.842-2.873(m, 1H), 3.799-3.811(m, 1H), 7.680-7.757(m, 3H), 8.303-8.321(dd, 1H), 8.472-8.485(d, 1H), 8.546-8.552(d, 1H), 9.097-9.099(d, 1H). | 396.4 |

-continued

| Example | Compound | Result | ¹H NMR(600 MHz, DMSO-d₆) | MS [M + H]⁺ |
|---|---|---|---|---|
| 11 | I-11 | Brown solid, with a yield of 27.4% | 0.589-0.615(m, 2H), 0.683-0.714(m, 2H), 2.267-2.270(d, 3H), 2.815-2.876(m, 7H), 3.285-3.342(m, 2H), 3.699-3.728(m, 2H), 7.729-7.821(m, 3H), 8.525-8.539(d, 1H), 8.658-8.665(d, 1H), 9.251-9.255(d, 1H), 9.355(s, 1H). | 385.2 |
| 12 | I-12 | White solid, with a yield of 79.1% | 0.573-0.585(m, 2H), 0.680-0.712(m, 2H), 2.274-2.277(d, 3H), 2.678-2.716(m, 4H), 2.844-2.874(m, 1H), 3.619(m, 2H), 3.912(m, 2H), 7.672-7.696(m, 2H), 7.773(s, 1H), 7.977-7.994(dd, 1H), 8.537-8.543(d, 1H), 8.731(s, 1H). | 400.2 |
| 13 | I-13 | Gray solid, with a yield of 31.9% | 0.558-0.583(m, 2H), 0.681-0.712(m, 2H), 2.212(s, 3H), 2.273-2.390(m, 7H), 2.842-2.873(m, 1H), 3.394(m, 2H), 3.662(m, 2H), 7.674-7.690(m, 2H), 7.769(s, 1H), 7.957-7.973(dd, 1H), 8.535-8.542(d, 1H), 8.714-8.716(d, 1H). | 397.3 |
| 14 | I-14 | White solid, with a yield of 53.3% | 0.570-0.588(m, 2H), 0.683-0.706(m, 2H), 1.544-1.610(m, 6H), 1.742-1.761(m, 2H), 2.274-2.277(d, 3H), 2.852-2.865(m, 1H), 3.378-3.398(t, 2H), 3.597-3.616(t, 2H), 7.668-7.690(m, 2H), 7.774-7.776(d, 1H), 7.950-7.967(dd, 1H), 8.543-8.550(d, 1H), 8.704-8.707(m, 1H). | 396.5 |
| 15 | I-15 | White solid, with a yield of 17.1% | 0.552-0.578(m, 2H), 0.688-0.720(m, 2H), 0.891-0.902(d, 6H), 1.884-1.929(m, 1H), 2.192-2.195(d, 3H), 2.840-2.865(m, 1H), 3.157-3.179(t, 2H), 7.662-7.697(m, 2H), 8.053-8.070(dd, 1H), 8.132-8.145(d, 1H), 8.526-8.532(d, 1H), 8.686-8.688(d, 1H), 8.828-8.848(t, 1H). | 370.1 |
| 16 | I-16 | Light yellow solid, with a yield of 24.3% | 0.565-0.580(m, 2H), 0.687-0.735(m, 5H), 0.934-0.945(d, 3H), 1.882-2.091(m, 1H), 2.187-2.203(m, 3H), 2.837-2.871(m, 1H), 2.959-3.017(d, 3H), 3.229-3.242(d, 1H), 3.334-3.347(d, 1H), 7.627-7.681(m, 3H), 7.969-7.992(m, 1H), 8.518-8.529(m, 1H), 8.618-8.637(m, 1H). | 384.2 |
| 17 | I-17 | While solid, with a yield of 20.7% | 0.559-0.570(m, 2H), 0.694-0.718(m, 2H), 1.558-1.6220(m, 4H), 1.705-1.7270(m, 2H), 1.896-1.924(m, 2H), 2.182-2.185(d, 3H), 2.837-2.868(m, 1H), 4.262-4.299(m, 1H), 7.647(s, 1H), 7.678-7.696(d, 1H), 8.045-8.062(dd, 1H), 8.121-8.134(d, 1H), 8.522-8.529(d, 1H), 8.591-8.605(d, 1H), 8.668-8.671(d, 1H). | 382.2 |
| 18 | I-18 | Light yellow solid, with a yield of 27.3% | 0.555-0.581(m, 2H), 0.688-0.719(m, 2H), 1.401(m, 2H), 1.632-1.734(m, 6H), 2.204(s, 3H), 2.830-2.908(m, 4H), 4.083-4.113(m, 1H), 7.606-7.679(m, 3H), 7.969-7.986(m, 1H), 8.524-8.530(d, 1H), 8.624(s, 1H). | 396.4 |
| 19 | I-19 | White solid, with a yield of 35.2% | 0.560-0.578(m, 2H), 0.695-0.710(m, 2H), 2.020-2.043(m, 2H), 2.186-2.190(d, 3H), 2.850-2.857(m, 1H), 3.444-3.477(m, 2H), 3.676-3.698(t, 2H), 7.652-7.698(m, 2H), 8.051-8.068(dd, 1H), 8.131-8.144(m, 1H), 8.521-8.528(d, 1H), 8.680-8.684(m, 1H), 8.995(m, 1H). | 390.2 |
| 20 | I-20 | White solid, with a yield of 34.5% | 0.574-0.581(m, 2H), 0.678-0.709(m, 5H), 0.925(m, 3H), 1.516-1.621(m, 4H), 2.171-2.175(d, 3H), 2.830-2.875(m, 1H), 3.176(m, 2H), 3.323-3.393(m, 2H), 7.421-7.459(m, 4H), 7.608-7.633(m, 2H), 8.515-8.521(d, 1H). | 397.4 |
| 21 | I-21 | White solid, with a yield of 71.7% | 0.579(m, 2H), 0.676-0.708(m, 2H), 1.164-1.427(m, 12H), 2.181-2.185(d, 3H), 2.839-2.870(m, 1H), 3.665-3.689(m, 2H), 7.380-7.394(m, 2H), 7.431-7.445(m, 2H), 7.610-7.626(m, 2H), 8.508-8.515(d, 1H). | 397.3 |
| 22 | I-22 | White solid, with a yield of 37.3% | 0.552-0.578(m, 2H), 0.696-0.708(m, 2H), 1.542-1.584(m, 4H), 1.698-1.712(m, 2H), 1.897-1.959(m, 2H), 2.163-2.166(d, 3H), 2.832-2.863(m, 1H), 4.235-4.287(m, 1H), 7.466-7.480(d, 2H), 7.590-7.636(m, 2H), 7.941-7.955(d, 2H), 8.351-8.363(d, 1H), 8.515-8.522(d, 1H). | 381.3 |
| 23 | I-23 | Light yellow solid, with a yield of 18.7% | 0.578(m, 2H), 0.677-0.709(m, 2H), 1.441(m, 2H), 1.668-1.736(m, 6H), 2.184-2.187(d, 3H), 2.845-2.868(m, 4H), 4.055(m, 1H), 7.460(m, 4H), 7.614-7.633(m. 2H), 8.515-8.522(d, 1H). | 395.4 |
| 24 | I-24 | Light yellow solid, with a yield of 42.6% | 0.562-0.575(m, 2H), 0.677-0.708(m, 2H), 1.130-1.150(m, 1H), 1.301-1.347(m, 4H), 1.609-1.630(m, 1H), 1.739-1.754(m, 2H), 1.834-1.847(m, 2H), 2.162-2.165(d, 3H), 2.832-2.862(m, 1H), 3.775-3.792(m, 1H), 7.465-7.478(d, 2H), 7.586-7.636(m, 2H), 7.940-7.954(d, 2H), 8.270-8.284(d, 1H), 8.514-8.521 (d, 1H). | 395.4 |
| 25 | I-25 | White solid, with a yield of 21.4% | 0.562-0.588(m, 2H), 0.689-0.709(m, 2H), 0.993(m, 2H), 1.358-1.800(m, 8H), 2.177-2.181 (d, 3H), 2.800-2.874(m, 4H), 4.300-4.315(m, 1H), 7.453(m, 4H), 7.615-7.633(m, 2H), 8.514-8.520(d, 1H). | 409.3 |
| 26 | I-26 | White solid, with a yield of 25.2% | 0.551-0.576(m, 2H), 0.675-0.707(m, 2H), 0.932-0.943(d, 3H), 1.097(m, 2H), 1.621-1.716(m, 3H), 2.180-2.183(d, 3H), 2.781-2.876(m, 2H), 3.082(m, 1H), 3.601(m, 1H), 4.485(m, 1H), 7.445-7.481(m, 4H), 7.607-7.630(m, 2H), 8.501(s, 1H). | 395.4 |
| 27 | I-27 | White solid, with a yield of 6.6% | 0.559-0.576(m, 2H), 0.683-0.698(m, 2H), 1.399(m, 2H), 1.736-1.809(m, 2H), 2.182-2.185(d, 3H), 2.837-2.867(m, | 397.3 |

| Example | Compound | Result | ¹H NMR(600 MHz, DMSO-d₆) | MS [M + H]⁺ |
|---|---|---|---|---|
| | | | 1H), 3.198(m, 2H), 3.515-3.544(m, 1H), 3.740-3.773(m, 1H), 4.024(m, 1H), 4.800-4.806(d, 1H), 7.449-7.488(m, 4H), 7.606-7.631(m, 2H), 8.505-8.512(d, 1H). | |
| 28 | I-28 | White solid, with a yield of 53.3% | 0.545-0.714(m, 4H), 1.566-1.735(m, 8H), 2.156-2.201(d, 3H), 2.831-2.868(m, 1H), 3.294-3.384(m, 2H), 3.568-3.604(m, 2H), 7.433-7.626(m, 6H), 8.495-8.539(d, 1H). | 395.4 |
| 29 | I-29 | White solid, with a yield of 33.0% | 0.563-0.566(m, 2H), 0.681-0.697(m, 2H), 2.179-2.182(d, 3H), 2.672(m, 4H), 2.834-2.865(m, 1H), 3.605(m, 2H), 3.889(m, 2H), 7.459-7.472(d, 2H), 7.499-7.512(d, 2H), 7.603-7.630(m, 2H), 8.505-8.512(d, 1H). | 399.1 |
| 30 | I-30 | White solid, with a yield of 40.9% | 0.560-0.577(m, 2H), 0.684-0.707(m, 2H), 0.912-0.923(d, 6H), 1.837-1.860(m, 1H), 2.185-2.188(d, 3H), 2.844-2.850(m, 1H), 3.094-3.115(m, 2H), 7.293-7.309(dd, 1H), 7.367-7.388(dd, 1H), 7.589-7.591(d, 1H), 7.635-7.684(m, 2H), 8.385(m, 1H), 8.517(s, 1H), | 387.3 |
| 31 | I-31 | Earthy yellow solid, with a yield of 21.7% | 0.569-0.572(m, 2H), 0.694-0.737(m, 5H), 0.925-0.936(d, 3H), 1.833-2.090(m, 1H), 2.188-2.197(m, 3H), 2.849-3.001(m, 5H), 3.321-3.347(m, 1H), 7.295-7.322(m, 1H), 7.373-7.403(m, 1H), 7.441-7.490(m, 1H), 7.618-7.651(m, 2H), 8.516-8.531(m, 1H). | 401.1 |
| 32 | I-32 | Light yellow solid, with a yield of 51.5% | 0.558-0.576(m, 2H), 0.684-0.707(m, 2H), 1.510-1.558(m, 4H), 1.678-1.691(m, 2H), 1.881-1.899(m, 2H), 2.180-2.184(d, 3H), 2.842-2.848(m, 1H), 4.214(m, 1H), 7.277-7.293(dd, 1H), 7.348-7.368(dd, 1H), 7.581(s, 1H), 7.621-7.650(m, 2H), 8.320-8.332(d, 1H), 8.518(s, 1H). | 399.1 |
| 33 | I-33 | White-like solid, with a yield of 12.9% | 0.561-0.579(m, 2H), 0.684-0.715(m, 2H), 1.419(m, 2H), 1.580-1.666(m, 6H), 2.198(s, 3H), 2.836-2.866(m, 1H), 2.906(s, 3H), 3.955(m, 1H), 7.296-7.311(m, 1H), 7.376-7.399(m, 1H), 7.434-7.484(m, 1H), 7.613-7.647(m, 2H), 8.537(s, 1H). | 413.3 |
| 34 | I-34 | White solid, with a yield of 52.0% | 0.562-0.572(m, 2H), 0.690-0.706(m, 2H), 1.839-1.914(m, 4H), 2.190-2.193(d, 3H), 2.849-2.855(m, 1H), 3.261-3.283(t, 2H), 3.487-3.510(t, 2H), 7.296-7.311(dd, 1H), 7.380-7.400(dd, 1H), 7.517-7.542(m, 1H), 7.609-7.648(m, 2H), 8.510(s, 1H). | 385.1 |
| 35 | I-35 | White solid, with a yield of 34.4% | 0.552-0.578(m, 2H), 0.682-0.713(m, 2H), 0.926-0.937(d, 3H), 1.056(m, 2H), 1.620(m, 2H), 1.719(m, 1H), 2.194-2.197(d, 3H), 2.796-2.860(m, 2H), 3.095(m, 1H), 3.418-3.439(d, 1H), 4.487-4.509(d, 1H), 7.297-7.312(dd, 1H), 7.375-7.394(dd, 1H), 7.478(m, 1H), 7.618-7.645(m, 2H), 8.502(s, 1H). | 413.3 |
| 36 | I-36 | White solid, with a yield of 23.3% | 0.569-0.576(m, 2H), 0.682-0.714(m, 2H), 2.195-2.198(d, 3H), 2.835-2.866(m, 1H), 3.289-3.311(m, 2H), 3.563-3.577(m, 2H), 3.676(m, 4H), 7.318-7.333(dd, 1H), 7.393-7.412(dd, 1H), 7.514-7.539(m, 1H), 7.612-7.650(m, 2H), 8.499(s, 1H). | 401.1 |
| 37 | I-37 | White solid, with a yield of 13.4% | 0.563-0.574(m, 2H), 0.676-0.719(m, 5H), 0.926(m, 3H), 1.959-1.961(m, 1H), 2.171(s, 3H), 2.850-3.015(m, 5H), 3.292-3.301(m, 1H), 6.822-6.848(m, 2H), 7.175(m, 1H), 7.585-7.683(m, 2H), 8.517(s, 1H), 10.024(s, 1H). | 399.1 |
| 38 | I-38 | White solid, with a yield of 38.4% | 0.569-0.576(m, 2H), 0.675-0.706(m, 2H), 1.205-1.216(d, 6H), 2.168-2.171(d, 3H), 2.829-2.859(m, 1H), 4.155-4.189(m, 1H), 6.895(s, 1H), 6.909-6.911(d, 1H), 7.580(s, 1H), 7.606-7.623(d, 1H), 7.983-7.996(d, 1H), 8.516-8.523(d, 1H), 8.626-8.639(d, 1H), 12.924(s, 1H). | 371.3 |
| 39 | I-39 | White solid, with a yield of 13.6% | 0.554-0.579(m, 2H), 0.677-0.700(m, 2H), 0.910-1.106(m, 5H), 1.526-1.719(m, 3H), 2.193-2.196(d, 3H), 2.728(t, 1H), 2.836-2.867(m, 1H), 2.905-3.018(m, 1H), 3.314-3.335(d, 1H), 3.812-3.827(d, 3H), 4.482-4.503(d, 1H), 6.972-6.994(m, 1H), 7.046(s, 1H), 7.210-7.275(m, 1H), 7.612-7.627(m, 2H), 8.496-8.502(d, 1H). | 425.3 |
| 40 | I-40 | Light yellow solid, with a yield of 66.4% | 0.571-0.579(m, 2H), 0.675-0.707(m, 2H), 1.785-1.848(m, 2H), 1.858-1.893(m, 2H), 2.187-2.190(d, 3H), 2.834-2.865(m, 1H), 3.155-3.176(t, 2H), 3.441-3.464(t, 2H), 3.831(s, 3H), 6.973-6.988(dd, 1H), 7.058-7.059(d, 1H), 7.273-7.286(d, 1H), 7.610-7.627(m, 2H), 8.504-8.510(d, 1H). | 397.3 |
| 41 | I-41 | Light yellow solid, with a yield of 19.9% | 0.550-0.576(m, 2H), 0.673-0.704(m, 2H), 0.819-0.843(t, 3H), 1.326(s, 6H), 1.773-1.810(q, 2H), 2.164-2.168(d, 3H), 2.830-2.891(m, 1H), 6.568-6.581(d, 1H), 6.712(s, 1H), 7.494(s, 1H), 7.532-7.545(d, 2H), 7.601-7.618(m, 1H), 8.511-8.517(d, 1H). | 398.3 |
| 42 | I-42 | Light yellow solid, with a yield of 39.7% | 0.565-0.577(m, 2H), 0.673-0.704(m, 2H), 0.915(s, 9H), 2.175-2.178(d, 3H), 2.834-2.865(m, 1H), 3.080-3.091(d, 2H), 6.414(s, 2H), 6.517-6.532(dd, 1H), 6.668-6.670(d, 1H), 7.565-7.610(m, 3H), 8.174-8.195(t, 1H), 8.493-8.500(d, 1H). | 398.2 |

| Example | Compound | Result | $^1$H NMR(600 MHz, DMSO-d$_6$) | MS [M + H]$^+$ |
|---|---|---|---|---|
| 43 | I-43 | White solid, with a yield of 26.5% | 0.550-0.580(m, 2H), 0.668-0.700(m, 2H), 2.172-2.176(d, 3H), 2.834-2.865(m, 1H), 3.487(m, 4H), 3.626(m, 4H), 5.352(s, 2H), 6.546-6.562(dd, 1H), 6.680-6.683(d, 1H), 7.088-7.101(d, 1H), 7.568-7.601(m, 2H), 8.485-8.492(d, 1H). | 398.2 |
| 44 | I-44 | White solid, with a yield of 13.8% | 0.550-0.576(m, 2H), 0.676-0.707(m, 2H), 0.916-0.927(d, 6H), 1.813-1.858(m, 1H), 2.172-2.175(d, 3H), 2.397(s, 3H), 2.828-2.858(m, 1H), 3.066-3.088(t, 2H), 7.239-7.259(m, 2H), 7.393-7.406(d, 1H), 7.556(s, 1H), 7.606-7.623(d, 1H), 8.328(t, 1H), 8.500-8.507(d, 1H). | 383.2 |
| 45 | I-45 | Gray solid, with a yield of 25.3% | 0.561-0.588(m, 2H), 0.677-0.708(m, 2H), 2.185-2.188(d, 3H), 2.296(s, 3H), 2.835-2.866(m, 1H), 3.063-3.077(m, 2H), 3.202(m, 2H), 3.431(m, 2H), 3.853-3.931(m, 2H), 7.271-7.321(m, 2H), 7.374-7.387(d, 1H), 7.585-7.643(m, 2H), 8.527-8.534(d, 1H). | 396.2 |
| 46 | I-46 | White solid, with a yield of 93.0% | 0.571-0.578(m, 2H), 0.675-0.707(m, 2H), 2.176-2.179(d, 3H), 2.292(s, 3H), 2.828-2.872(m, 1H), 3.194(m, 2H), 3.537(m, 2H), 3.678(m, 4H), 7.252-7.300(m, 3H), 7.586-7.623(m, 2H), 8.494-8.501(d, 1H). | 397.3 |
| 47 | I-47 | White solid, with a yield of 25.5% | 0.559-0.576(m, 2H), 0.678-0.709(m, 2H), 1.184-1.311 (m, 4H), 1.385-1.447(m, 2H), 1.748-1.833(m, 4H), 2.183-2.186(d, 3H), 2.505-2.543(m, 1H), 2.829-2.854(m, 1H), 7.167-7.181(m, 1H), 7.312-7.335(dd, 1H), 7.581-7.608(m, 2H), 7.958-7.986(t, 1H), 8.497-8.504(d, 1H), 9.678(s, 1H). | 413.3 |
| 48 | I-48 | White solid, with a yield of 25.5% | 0.567-0.585(m, 2H), 0.672-0.703(m, 2H), 0.912-0.972(m, 2H), 1.142-1.233(m, 3H), 1.619-1.704(m, 4H), 1.779-1.801(m, 2H), 2.192-2.196(d, 3H), 2.830-2.861(m, 1H), 2.980-2.992(d, 2H), 6.820(m, 1H), 7.011-7.028(dd, 1H), 7.112-7.137(dd, 1H), 7.530-7.551(m, 2H), 8.504-8.510(d, 1H). | 399.0 |
| 49 | I-49 | White solid, with a yield of 31.8% | 0.552-0.580(m, 2H), 0.679-0.700(m, 2H), 0.895-0.906(d, 6H), 1.686-1.731(m, 1H), 2.172-2.176(d, 3H), 2.247(s, 3H), 2.828-2.858(m, 1H), 2.940-2.961(m, 2H), 6.653-6.672(m, 1H), 7.098-7.144(m, 2H), 7.546-7.558(m, 2H), 7.707(s, 1H), 7.980-7.994(d, 1H), 8.470-8.476(d, 1H). | 398.2 |
| 50 | I-50 | White solid, with a yield of 12.9% | 0.551-0.576(m, 2H), 0.668-0.687(m, 2H), 1.369-1.400(m, 2H), 1.545-1.570(m, 2H), 1.647-1.671(m, 2H), 1.844-1.874(m, 2H), 2.171-2.234(m, 6H), 2.834-2.852)m, 1H), 3.953-3.964(m, 1H), 6.662-6.673(d, 1H), 7.097-7.139(m, 2H), 7.544-7.585(m, 3H), 8.013-8.027(d, 1H), 8.469(s, 1H). | 410.2 |
| 51 | I-51 | White solid, with a yield of 25.2% | 0.563-0.576(m, 2H), 0.671-0.702(m, 2H), 0.940-0.951(d, 6H), 1.911-1.956(m, 1H), 2.187-2.190(d, 3H), 2.838-2.857(m, 1H), 3.205-3.226(t, 2H), 7.204-7.221(dd, 1H), 7.427-7.441(d, 1H), 7.559-7.599(m, 2H), 7.691-7.694(d, 1H), 8.127-8.146(t, 1H), 8.481-8.488(d, 1H). | 398.1 |
| 52 | I-52 | While solid, with a yield of 13.2% | 0.568-0.579(m, 2H), 0.673-0.704(m, 2H), 0.913-0.938(t, 3H), 1.357-1.419(m, 2H), 1.565-1.614(m, 2H), 2.188-2.191(d, 3H), 2.835-2.865(m, 1H), 3.365-3.397(m, 2H), 7.209-7.225(dd, 1H), 7.435-7.449(d, 1H), 7.565-7.604(m, 2H), 7.695-7.698(d, 1H), 8.085-8.103(t, 1H), 8.490-8.496(d, 1H). | 398.1 |
| 53 | I-53 | White solid, with a yield of 11.9% | 0.551-0.577(m, 2H), 0.672-0.695(m, 2H), 0.962(s, 9H), 2.190-2.193(d, 3H), 2.839-2.851(m, 1H), 7.198-7.215(dd, 1H), 7.415-7.428(d, 1H), 7.559-7.601(m, 2H), 7.685-7.688(d, 1H), 8.041(m, 1H), 8.478(s, 1H). | 398.1 |
| 54 | I-54 | White solid, with a yield of 12.9% | 0.552-0.578(m, 2H), 0.679-0.703(m, 2H), 1.555-1.593(m, 4H), 1.691-1.705(m, 2H), 1.968-1.990(m, 2H), 2.186-2.189(d, 3H), 2.833-2.864(m, 1H), 4.165-4.186(m, 1H), 7.206-7.223(dd, 1H), 7.441-7.455(d, 1H), 7.56.3-7.600(m, 2H), 7.694-7.696(4, 1H), 8.119-8.130(d, 1H), 8.490-8.497(d, 1H). | 410.2 |
| 55 | I-55 | White solid, with a yield of 46.9% | 0.573-0.586(m, 2H), 0.682-0.713(m, 2H), 1.543-1.580(m, 4H), 1.631-1.658(m, 2H), 2.321-2.324(d, 3H), 2.829-2.873(m, 1H), 3.626(m, 4H), 7.242-7.249(d, 1H), 7.409-7.415(d, 1H), 7.635-7.652(d, 1H), 7.748(s, 1H), 8.561-8.568(d, 1H). | 387.2 |
| 56 | I-56 | Light yellow solid, with a yield of 22.3% | 0.581-0.588(m, 2H), 0.693-0.717(m, 2H), 0.938-0.948(d, 3H), 1.106-1.132(m, 2H), 1.689-1.710(m, 3H), 2.326-2.329(d, 3H), 2.837-2.868(m, 1H), 3.003(m, 2H), 4.271(m, 2H), 7.249-7.255(4, 1H), 7.417-7.424(d, 1H), 7.639-7.656(m, 1H), 7.750(s, 1H), 8.564-8.571(d, 1H). | 401.1 |

Examples 57~81: Preparation of Compounds I-57~I-81

Synthetic Route:

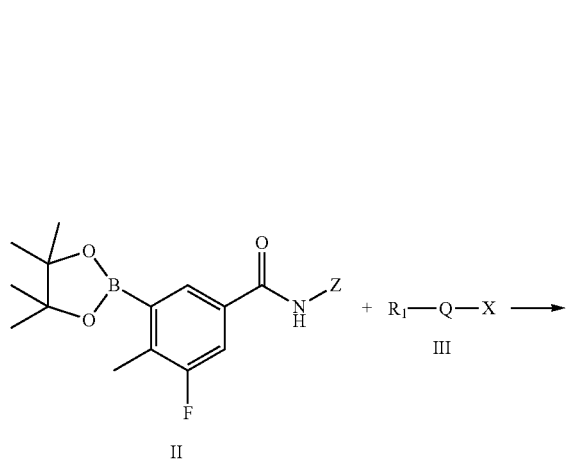

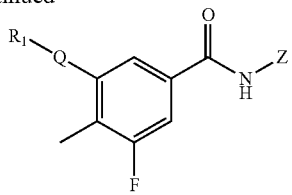

Wherein, the definitions of $R_1$, Z, Q and X were shown in the table below.

Preparation Method:

Compound III (e.g., 1.5 mmol) and compound II (e.g., 1.5 mmol) were added in isopropyl alcohol (e.g., 30 mL), 1M aqueous sodium bicarbonate (e.g., 1.9 mL) and $Pd(PPh_3)_4$ (e.g., 0.016 mmol) were added and refluxed at 90° C. for 10 hours. After completion of the reaction, the reaction solution was concentrated under reduced pressure. The residue was purified by column chromatography (petroleum ether:ethyl acetate=5:1~1:1) to give the target compound.

| Example | Compound | Chemical Name | Structure | X | $R_1$ | Q | Z |
|---|---|---|---|---|---|---|---|
| 57 | I-57 | 6-(5-(cyclopropylcarbamoyl)-3-fluoro-2-methylphenyl)-N-isobutylpyridazin-3-carboxamide | 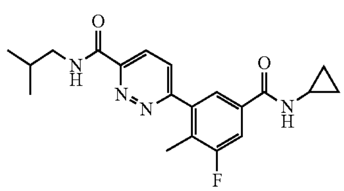 [SMILES: Cc1c(F)cc(C(=O)NC2CC2)cc1-c1ccc(C(=O)NCC(C)C)nn1] | Cl | | | |
| 58 | I-58 | 6-(5-(cyclopropylcarbamoyl)-3-fluoro-2-methylphenyl)-N-(sec-butyl)pyridazin-3-carboxamide | 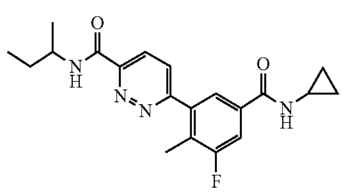 [SMILES: CCC(C)NC(=O)c1ccc(-c2cc(C(=O)NC3CC3)cc(F)c2C)nn1] | Cl | | | |
| 59 | I-59 | 6-(5-(cyclopropylcarbamoyl)-3-fluoro-2-methylphenyl)-N-neopentylpyridazin-3-carboxamide | 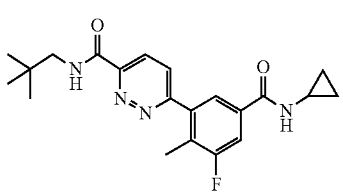 [SMILES: Cc1c(F)cc(C(=O)NC2CC2)cc1-c1ccc(C(=O)NCC(C)(C)C)nn1] | Cl | | | |
| 60 | I-60 | 6-(5-(cyclopropylcarbamoyl)-3-fluoro-2-methylphenyl)-N-isopentylpyridazin-3-carboxamide | 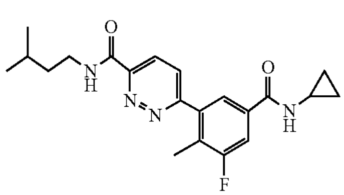 [SMILES: Cc1c(F)cc(C(=O)NC2CC2)cc1-c1ccc(C(=O)NCCC(C)C)nn1] | Cl | | | |

| Example | Compound | Chemical Name | Structure | X | R₁ | Q | Z |
|---|---|---|---|---|---|---|---|
| 61 | I-61 | 6-(5-(cyclopropylcarbamoyl)-3-fluoro-2-methylphenyl)-N-(cyclopropylmethyl)pyridazin-3-carboxamide | 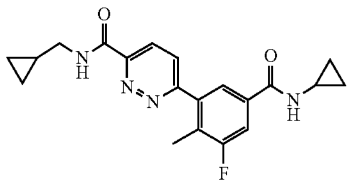 [SMILES: Cc1c(F)cc(C(=O)NC2CC2)cc1-c1ccc(C(=O)NCC2CC2)nn1] | Cl | cyclopropylmethyl-NHC(O)- | | |
| 62 | I-62 | 6-(5-(cyclopropylcarbamoyl)-3-fluoro-2-methylphenyl-N-cyclohexyl-N-methylpyridazin-3-carboxamide | 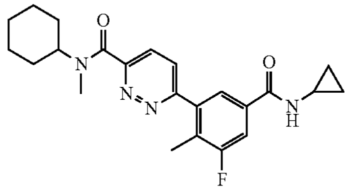 [SMILES: Cc1c(F)cc(C(=O)NC2CC2)cc1-c1ccc(C(=O)N(C)C2CCCCC2)nn1] | Cl | N-cyclohexyl-N-methylamide | | |
| 63 | I-63 | 6-(5-(azetidin-3-yl-carbamoyl)-3-fluoro-2-methylphenyl)-N-isobutylpyridazin-3-carboxamide | 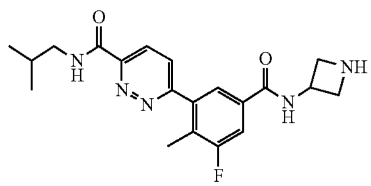 [SMILES: Cc1c(F)cc(C(=O)NC2CNC2)cc1-c1ccc(C(=O)NCC(C)C)nn1] | Cl | isobutyl-NHC(O)- | | azetidine |
| 64 | I-64 | 6-(5-(azetidin-3-yl-carbamoyl)-3-fluoro-2-methylphenyl)-N-(sec-butyl)pyridazin-3-carboxamide | 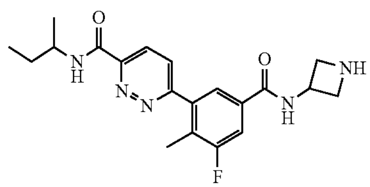 [SMILES: CCC(C)NC(=O)c1ccc(-c2cc(C(=O)NC3CNC3)cc(F)c2C)nn1] | Cl | sec-butyl-NHC(O)- | | |
| 65 | I-65 | 6-(5-(azetidin-3-yl-carbamoyl)-3-fluoro-2-methylphenyl)-N-neopentylpyridazin-3-carboxamide | 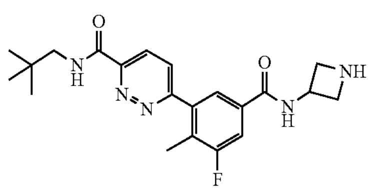 [SMILES: Cc1c(F)cc(C(=O)NC2CNC2)cc1-c1ccc(C(=O)NCC(C)(C)C)nn1] | Cl | neopentyl-NHC(O)- | | |
| 66 | I-66 | 6-(5-(azetidin-3-yl-carbamoyl)-3-fluoro-2-methylphenyl)-N-(cyclopropylmethyl)pyridazin-3-carboxamide | 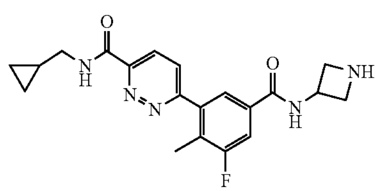 [SMILES: Cc1c(F)cc(C(=O)NC2CNC2)cc1-c1ccc(C(=O)NCC2CC2)nn1] | Cl | cyclopropylmethyl-NHC(O)- | | |
| 67 | I-67 | 6-(5-(azetidin-3-yl-carbamoyl)-3-fluoro-2-methylphenyl)-N-cyclopentylpyridazin-3-carboxamide | 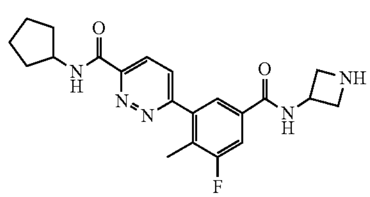 [SMILES: Cc1c(F)cc(C(=O)NC2CNC2)cc1-c1ccc(C(=O)NC2CCCC2)nn1] | Cl | cyclopentyl-NHC(O)- | | |
| 68 | I-68 | 6-(5-(azetidin-3-yl-carbamoyl)-3-fluoro-2-methylphenyl)-N-cyclohexylpyridazin-3-carboxamide | 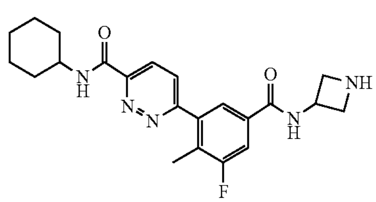 [SMILES: Cc1c(F)cc(C(=O)NC2CNC2)cc1-c1ccc(C(=O)NC2CCCCC2)nn1] | Cl | cyclohexyl-NHC(O)- | | |

| Example | Compound | Chemical Name | Structure | X | R₁ | Q | Z |
|---|---|---|---|---|---|---|---|
| 69 | I-69 | 6-(5-(azetidin-3-yl-carbamoyl)-3-fluoro-2-methylphenyl)-N-ethyl-N-isopropylpyridazin-3-carboxamide | 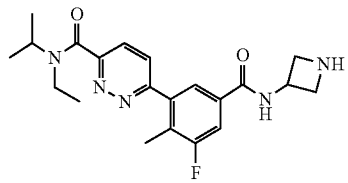 [SMILES: CCN(C(=O)c1ccc(-c2cc(C(=O)NC3CNC3)cc(F)c2C)nn1)C(C)C] | Cl | | | |
| 70 | I-70 | 6-(5-(azetidin-3-yl-carbamoyl)-3-fluoro-2-methylphenyl)-N-butyl-N-methylpyridazin-3-carboxamide | 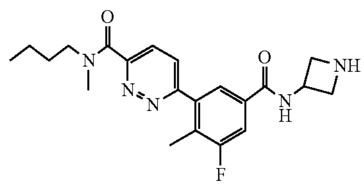 [SMILES: CCCCN(C)C(=O)c1ccc(-c2cc(C(=O)NC3CNC3)cc(F)c2C)nn1] | Cl | | | |
| 71 | I-71 | 6-(5-(azetidin-3-yl-carbamoyl)-3-fluoro-2-methylphenyl)-N-isobutyl-N-methylpyridazin-3-carboxamide | 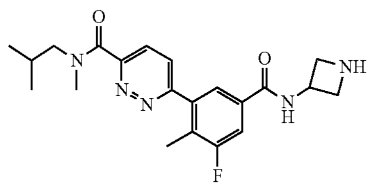 [SMILES: Cc1c(F)cc(C(=O)NC2CNC2)cc1-c1ccc(C(=O)N(C)CC(C)C)nn1] | Cl | | | |
| 72 | I-72 | 6-(5-(azetidin-3-yl-carbamoyl)-3-fluoro-2-methylphenyl)-N-neopentylnicotinamide | 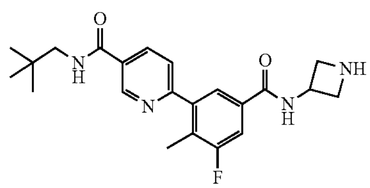 [SMILES: Cc1c(F)cc(C(=O)NC2CNC2)cc1-c1ccc(C(=O)NCC(C)(C)C)cn1] | Cl | | | |
| 73 | I-73 | N-cyclopentyl-6-(3-fluoro-5-((2-hydroxyethyl)carbamoyl)-2-methylphenyl)pyridazin-3-carboxamide | 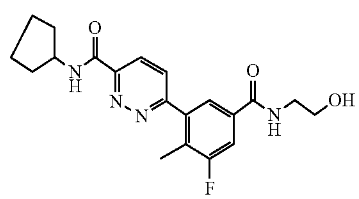 [SMILES: Cc1c(F)cc(C(=O)NCCO)cc1-c1ccc(C(=O)NC2CCCC2)nn1] | Cl | | | |
| 74 | I-74 | N-cyclohexyl-6-(3-fluoro-5-((2-hydroxyethyl)carbamoyl)-2-methylphenyl)pyridazin-3-carboxamide | 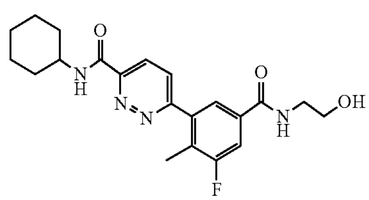 [SMILES: Cc1c(F)cc(C(=O)NCCO)cc1-c1ccc(C(=O)NC2CCCCC2)nn1] | Cl | | | |
| 75 | I-75 | N-ethyl-6-(3-fluoro-5-((2-hydroxyethyl)carbamoyl)-2-methylphenyl)-N-isopropylpyridazin-3-carboxamide | 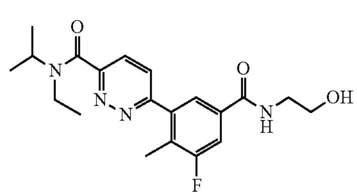 [SMILES: CCN(C(=O)c1ccc(-c2cc(C(=O)NCCO)cc(F)c2C)nn1)C(C)C] | Cl | | | |
| 76 | I-76 | N-butyl-6-(3-fluoro-5-((2-hydroxyethyl)carbamoyl)-2-methylphenyl)-N-methylpyridazin-3-carboxamide | 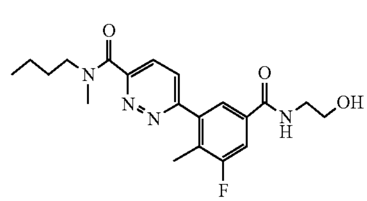 [SMILES: CCCCN(C)C(=O)c1ccc(-c2cc(C(=O)NCCO)cc(F)c2C)nn1] | Cl | | | |

-continued

| Example | Compound | Chemical Name | Structure | X | R₁ | Q | Z |
|---|---|---|---|---|---|---|---|
| 77 | I-77 | 6-(3-fluoro-5-((2-hydroxyethyl)carbamoyl)-2-methylphenyl)-N-isobutyl-N-methylpyridazin-3-carboxamide | 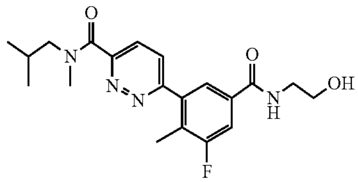 [SMILES: Cc1c(F)cc(C(=O)NCCO)cc1-c1ccc(C(=O)N(C)CC(C)C)nn1] | Cl | | | |
| 78 | I-78 | 6-(3-fluoro-5-((2-hydroxyethyl)carbamoyl)-2-methylphenyl)-N-neopentylnicotinamide | 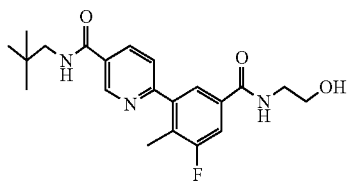 [SMILES: Cc1c(F)cc(C(=O)NCCO)cc1-c1ccc(C(=O)NCC(C)(C)C)cn1] | Cl | | | |
| 79 | I-79 | 6-(5-(allylcarbamoyl)-3-fluoro-2-methylphenyl)-N-cyclopentylpyridazin-3-carboxamide | 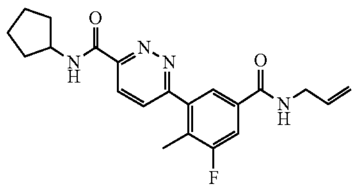 [SMILES: C=CCNC(=O)c1cc(F)c(C)c(-c2ccc(C(=O)NC3CCCC3)nn2)c1] | Cl | | | |
| 80 | I-80 | 6-(5-(allylcarbamoyl)-3-fluoro-2-methylphenyl)-N-cyclohexylpyridazin-3-carboxamide | 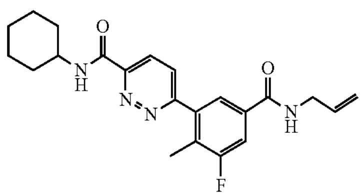 [SMILES: C=CCNC(=O)c1cc(F)c(C)c(-c2ccc(C(=O)NC3CCCCC3)nn2)c1] | Cl | | | |
| 81 | I-81 | 6-(5-(allylcarbamoyl)-3-fluoro-2-methylphenyl)-N-neopentylnicotinamide | 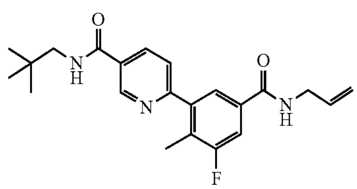 [SMILES: C=CCNC(=O)c1cc(F)c(C)c(-c2ccc(C(=O)NCC(C)(C)C)cn2)c1] | Cl | | | |

The results of the physical characterization of the above compounds according to the present invention are shown in the table below.

| Example | Compound | Structure | Result | ¹HNMR (600 MHz, DMSO-d₆) δ* | MS [M + H]⁺# |
|---|---|---|---|---|---|
| 57 | I-57 | 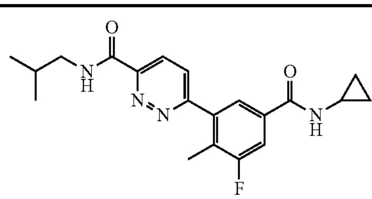 | White-like solid, with a yield of 63.9% | 0.582-0.588 (m, 2H), 0.723-0.735 (m, 2H), 0.923 (d, 6H), 1.927-1.997 (m, 2H), 2.287 (s, 3H), 2.857-2.887 (m, 1H), 3.215 (t, 2H), 7.787 (d, 1H), 7.851 (s, 1H), 8.150 (d, 1H), 8.331 (d, 1H), 8.600 (d, 1H), 9.374 (t, 1H). | 371.3 |
| 58 | I-58 | 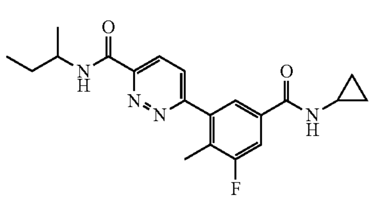 [SMILES: CCC(C)NC(=O)c1ccc(-c2cc(C(=O)NC3CC3)cc(F)c2C)nn1] | White solid, with a yield of 31.3% | CD₃OD: 0.625-0.652 (m, 2H), 0.803-0.824 (m, 2H), 0.999 (t, 3H), 1.309 (d, 3H), 1.656-1.717 (m, 2H), 2.309 (s, 3H), 2.848-2.871 (m, 1H), 4.112-4.146 (m, 1H), 7.703 (d, 1H), 7.782 (s, 1H), 8.054 (d, 1H), 8.382 (d, 1H), 8.853 (d, 1H). | 371.1 |

-continued

| Example | Compound | Structure | Result | ¹HNMR (600 MHz, DMSO-d$_6$) δ* | MS [M + H]⁺# |
|---|---|---|---|---|---|
| 59 | I-59 | 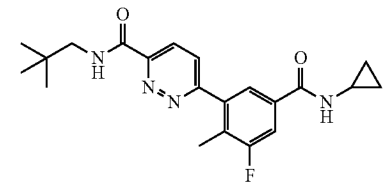 [SMILES: Cc1c(F)cc(C(=O)NC2CC2)cc1-c1ccc(C(=O)NCC(C)(C)C)nn1] | White solid, with a yield of 43.8% | 0.582-0.586 (m, 2H), 0.715-0.723 (m, 2H), 0.951 (s, 9H), 2.294 (s, 3H), 2.863-2.880 (m, 1H), 3.238 (d, 2H), 7.789 (d, 1H), 7.857 (s, 1H), 8.159 (d, 1H), 8.338 (d, 1H), 8.605 (d, 1H), 9.186 (m, 1H). | 383.1 [M − H]⁻ |
| 60 | I-60 | 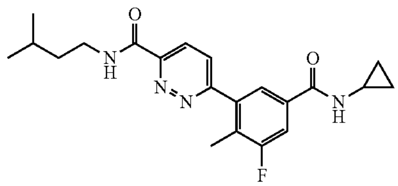 [SMILES: Cc1c(F)cc(C(=O)NC2CC2)cc1-c1ccc(C(=O)NCCC(C)C)nn1] | Light yellow solid, with a yield of 12.1% | 0.569-0.595 (m, 2H), 0.704-0.736 (m, 2H), 0.932 (m, 6H), 1.484-1.520 (m, 2H), 1.620-1.664 (m, 1H), 2.284 (d, 3H), 2.857-2.888 (m, 1H), 3.390-3.424 (m, 2H), 7.787 (d, 1H), 7.845 (s, 1H), 8.145 (d, 1H), 8.324 (d, 1H), 8.601 (d, 1H), 9.362 (m, 1H). | 384.7 |
| 61 | I-61 | 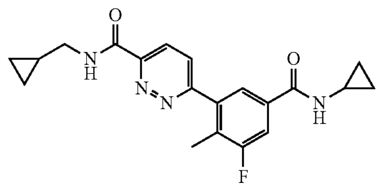 [SMILES: Cc1c(F)cc(C(=O)NC2CC2)cc1-c1ccc(C(=O)NCC2CC2)nn1] | White solid, With a yield of 46.3% | 0.283-0.307 (m, 2H), 0.434-0.463 (m, 2H), 0.570-0.588 (m, 2H), 0.695-0.718 (m, 10), 1.113-1.137 (m, 1H), 2.276 (s, 3H), 2.855-2.873 (m, 1H), 3.253 (m, 2H), 7.779 (d, 1H), 7.840 (s, 1H), 8.143 (d, 1H), 8.331 (d, 1H), 8.586 (d, 1H), 9.439 (m, 1H). | 369.0 |
| 62 | I-62 | 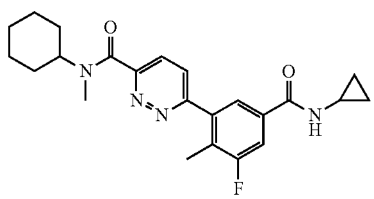 [SMILES: Cc1c(F)cc(C(=O)NC2CC2)cc1-c1ccc(C(=O)N(C)C2CCCCC2)nn1] | White solid, with a yield of 28.2% | 0.583-0.593 (m, 2H), 0.712-0.723 (m, 2H), 1.033-1.046 (m, 2H), 1.171-1.997 (m, 8H), 2.284 (s, 3H), 2.859-2.988 (m, 3H), 3.365-3.410 (m, 1H), 4.384-4.424 (m, 1H), 7.772 (d, 1H), 7.851 (d, 1H), 7.978-8.013 (m, 1H), 8.070-8.096 (m, 1H), 8.610-8.608 (m, 1H). | 410.8 |
| 63 | I-63 | 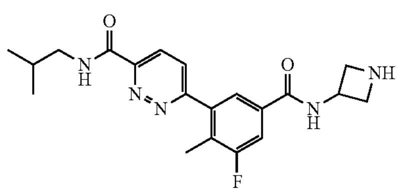 [SMILES: Cc1c(F)cc(C(=O)NC2CNC2)cc1-c1ccc(C(=O)NCC(C)C)nn1] | White-like solid, with a yield of 20.5% | CD$_3$OD: 1.039 (d, 6H), 2.050 (m, 1H), 2.356 (s, 3H), 3.371-3.382 (m, 2H), 4.339-4.409 (m, 4H), 4.881-4.899 (m, 1H), 7.805 (d, 1H), 7.896 (s, 1H), 8.094 (d, 1H), 8.425 (d, 1H), 9.244 (m, 1H). | 386.1 |
| 64 | I-64 | 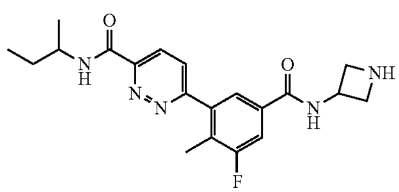 [SMILES: CCC(C)NC(=O)c1ccc(-c2cc(C(=O)NC3CNC3)cc(F)c2C)nn1] | White-like solid, with a yield of 16.4% | CD$_3$OD: 1.028 (t, 3H), 1.333 (m, 3H), 1.716 (m, 2H), 2.357 (s, 3H), 4.145-4.179 (m, 1H), 4.334-4.400 (m, 4H), 4.877 (m, 1H), 7.806 (d, 1H), 7.893 (s, 1H), 8.092 (d, 1H), 8.423 (d, 1H). | 386.0 |
| 65 | I-65 | 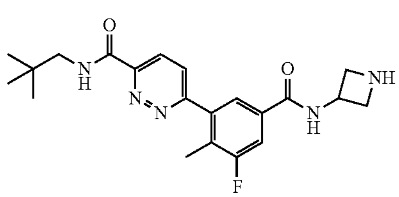 | White-like solid, with a yield of 15.8% | CD$_3$OD: 1.054 (t, 9H), 2.362 (d, 3H), 3.383 (d, 2H), 4.340-4.405 (m, 4H), 4.853 (m, 1H), 7.807 (d, 1H), 7.897 (s, 1H), 8.104 (d, 1H), 8.437 (d, 1H), 9.063 (m, 1H). | 400.2 |
| 66 | I-66 | 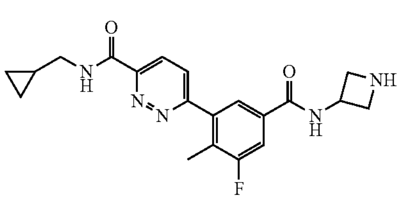 [SMILES: Cc1c(F)cc(C(=O)NC2CNC2)cc1-c1ccc(C(=O)NCC2CC2)nn1] | White-like solid, with a yield of 13.7% | CD$_3$OD: 0.373-0.381 (m, 2H), 0.583-0.596 (m, 2H), 1.157-1.227 (m, 1H), 2.353 (s, 3H), 3.401-3.412 (m, 2H), 4.338-4.412 (m, 4H), 4.889 (m, 1H), 7.808 (d, 1H), 7.901-7.912 (m, 1H), 8.097 (d, 1H), 8.429 (d, 1H), 9.275 (m, 1H). | 384.0 |

| Example | Compound | Structure | Result | ¹HNMR (600 MHz, DMSO-d₆) δ* | MS [M + H]⁺# |
|---|---|---|---|---|---|
| 67 | I-67 | 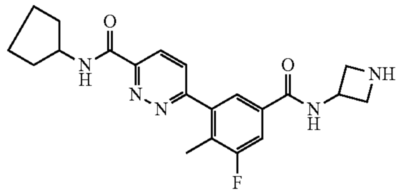 [SMILES: Cc1c(F)cc(C(=O)NC2CNC2)cc1-c1ccc(C(=O)NC2CCCC2)nn1] | White-like solid, with a yield of 11.4% | 1.568-1.592 (m, 2H), 1.667-1.760 (m, 4H), 1.925-1.952 (m, 2H), 2.300 (d, 3H), 4.111-4.194 (m, 4H), 4.339-4.376 (m, 1H), 4.821-4.846 (m, 1H), 7.840 (dd, 1H), 7.885 (d, 1H), 8.147 (d, 1H), 8.334 (d, 1H), 8.802 (s, 2H), 9.160 (d, 1H), 9.282 (d, 1H). | 398.9 |
| 68 | I-68 | 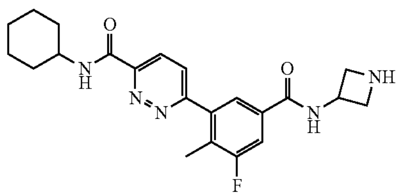 [SMILES: Cc1c(F)cc(C(=O)NC2CNC2)cc1-c1ccc(C(=O)NC2CCCCC2)nn1] | White-like solid, with a yield of 15.3% | 1.152-1.179 (m, 1H), 1.335-1.361 (m, 2H), 1.494-1.518 (m, 2H), 1.622-1.644 (m, 1H), 1.752-1.774 (m, 2H), 1.835-1.855 (m, 2H), 2.301 (d, 3H), 3.888-3.900 (m, 1H), 4.115-4.189 (m, 4H), 4.834-4.846 (m, 1H), 7.838-7.857 (m, 1H), 7.892 (d, 1H), 8.151 (d, 1H), 8.339 (d, 1H), 8.843 (s, 1H), 9.067 (d, 1H), 9.308 (m, 1H). | 412.3 |
| 69 | I-69 | 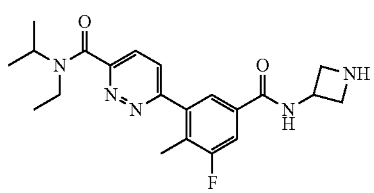 [SMILES: CCN(C(=O)c1ccc(-c2cc(C(=O)NC3CNC3)cc(F)c2C)nn1)C(C)C] | White-like solid, with a yield of 15.1% | CD₃OD: 1.308-1.450 (m, 9H), 2.358-2.374 (m, 3H), 3.451-3.618 (m, 2H), 4.025-4.070 (m, 1H), 4.272-4.348 (m, 4H), 4.883 (m, 1H), 7.795 (d, 1H), 7.902 (s, 1H), 7.998-8.018 (m, 1H), 8.071 (d, 1H). | 400.0 |
| 70 | I-70 | 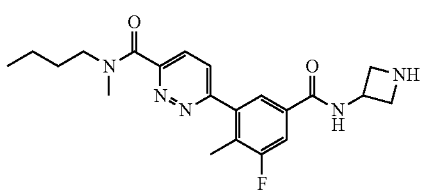 [SMILES: CCCCN(C)C(=O)c1ccc(-c2cc(C(=O)NC3CNC3)cc(F)c2C)nn1] | White-like solid, with a yield of 18.4% | 0.752-0.986 (m, 3H), 1.149-1.402 (m, 2H), 1.591-1.644 (m, 2H), 2.287-2.304 (m, 3H), 3.010-3.089 (m, 3H), 3.326 (t, 1H), 3.56 (t, 1H), 4.100-4.205 (m, 4H), 4.822-4.848 (m, 1H), 7.826 (d, 1H), 7.904 (d, 1H), 8.017 (dd, 1H), 8.097 (dd, 1H), 8.826 (s, 1H), 9.300 (m, 1H). | 399.9 |
| 71 | I-71 | 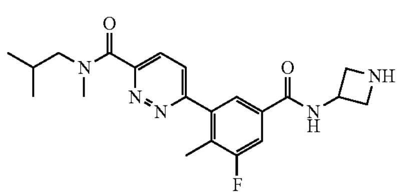 [SMILES: Cc1c(F)cc(C(=O)NC2CNC2)cc1-c1ccc(C(=O)N(C)CC(C)C)nn1] | White-like solid, with a yield of 20.0% | 0.756 (d, 3H), 0.976 (d, 3H), 1.995-2.176 (m, 1H), 2.291-2.306 (m, 3H), 3.008-3.093 (m, 3H), 3.235-3.415 (m, 2H), 4.119-4.194 (m, 4H), 4.826-4.864 (m, 1H), 7.824 (d, 1H), 7.911 (d, 1H), 8.008 (dd, 1H), 8.095 (dd, 1H), 9.309 (m, 1H). | 400.8 |
| 72 | I-72 | 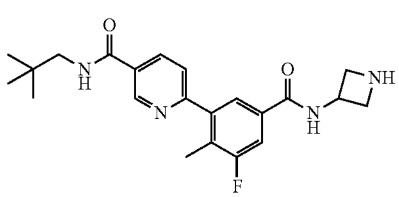 [SMILES: Cc1c(F)cc(C(=O)NC2CNC2)cc1-c1ccc(C(=O)NCC(C)(C)C)cn1] | White-like solid, with a yield of 15.9% | 0.9431 (s, 9H), 2.299 (d, 3H), 3.171 (d, 2H), 4.093-4.146 (m, 2H), 4.166-4.187 (m, 2H), 4.808-4.833 (m, 1H), 7.736-7.755 (m, 2H), 7.830 (d, 1H), 8.357 (dd, 1H), 8.650 (t, 1H), 9.139-9.144 (m, 1H), 9.225 (d, 1H). | 398.9 |
| 73 | I-73 | 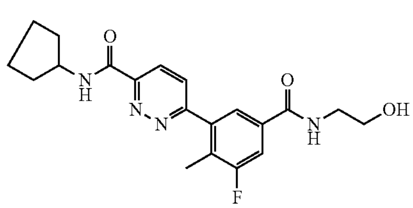 [SMILES: Cc1c(F)cc(C(=O)NCCO)cc1-c1ccc(C(=O)NC2CCCC2)nn1] | White solid, with a yield of 16.5% | CD₃OD: 1.694-1.714 (m, 4H), 1.836 (m, 2H), 2.086-2.097 (m, 2H), 2.313 (s, 3H), 3.507 (t, 2H), 3.7080, (t, 2H), 4.418-4.441 (m, 1H), 7.740 (d, 1H), 7.823 (s, 1H), 8.058 (d, 1H), 8.379 (d, 1H). | 387.1 |

-continued

| Example | Compound | Structure | Result | ¹HNMR (600 MHz, DMSO-d₆) δ* | MS [M + H]⁺# |
|---|---|---|---|---|---|
| 74 | I-74 | 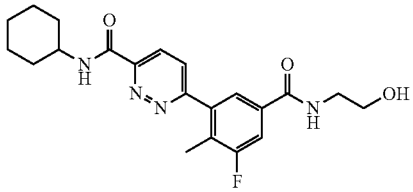 [SMILES: Cc1c(F)cc(C(=O)NCCO)cc1-c1ccc(C(=O)NC2CCCCC2)nn1] | White solid, with a yield of 28.9% | 1.151-1.200 (m, 2H), 1.300-1.401 (m, 2H), 1.469-1.529 (m, 2H), 1.742-1.764 (m, 2H), 1.828-1.845 (m, 2H), 2.285 (s, 3H), 3.292-3.355 (m, 2H), 3.501-3.530 (m, 2H), 3.856-3.908 (m, 1H), 4.734 (m, 1H), 7.810 (d, 1H), 7.877 (s, 1H), 8.144 (d, 1H), 8.322 (d, 1H), 8.624 (m, 1H), 9.062 (d, 1H). | 401.0 |
| 75 | I-75 | 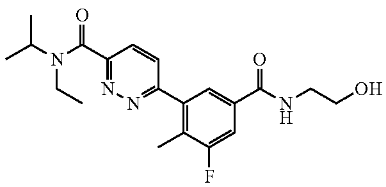 [SMILES: CCN(C(=O)c1ccc(-c2cc(C(=O)NCCO)cc(F)c2C)nn1)C(C)C] | White solid, with a yield of 17.2% | 1.171-1.325 (m, 9H), 2.290-2.302 (m, 3H), 3.304-3.482 (m, 4H), 3.515-3.536 (m, 2H), 3.886-3.908 (m, 1H), 4.732 (m, 1H), 7.781 (d, 1H), 7.896-7.905 (m, 1H), 7.990-8.013 (m, 1H), 8.087 (d, 1H), 8.638 (m, 1H). | 389.2 |
| 76 | I-76 | 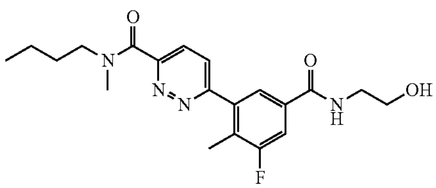 [SMILES: CCCCN(C)C(=O)c1ccc(-c2cc(C(=O)NCCO)cc(F)c2C)nn1] | White solid, with a yield of 18.9% | 0.724-0.977 (m, 3H), 1.127-1.405 (m, 2H), 1.568-1.648 (m, 2H), 2.283 (d, 3H), 3.003-3.080 (d, 3H), 3.308-3.358 (m, 3H), 3.505-3.564 (m, 3H), 4.728-4.747 (m, 1H), 7.799 (d, 1H), 7.889 (s, 1H), 8.001 (dd, 1H), 8.087 (d, 1H), 8.626 (s, 1H). | 389.1 |
| 77 | I-77 | 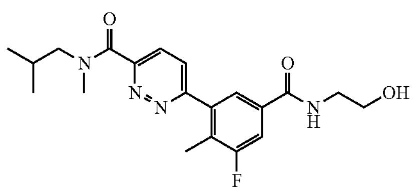 [SMILES: Cc1c(F)cc(C(=O)NCCO)cc1-c1ccc(C(=O)N(C)CC(C)C)nn1] | White solid, with a yield of 19.0% | 0.745 (d, 3H), 0.967 (d, 3H), 1.905-2.143 (m, 1H), 2.285 (d, 3H), 2.999-3.405 (m, 4H), 3.502-3.531 (m, 2H), 4.726-4.744 (m, 1H), 7.797 (d, 1H), 7.895 (d, 1H), 7.993 (dd, 1H), 8.084 (dd, 1H), 8.638 (m, 1H). | 389.2 |
| 78 | I-78 | 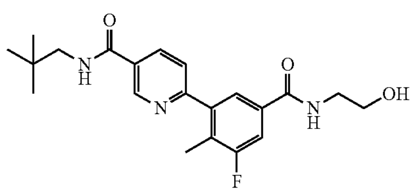 [SMILES: Cc1c(F)cc(C(=O)NCCO)cc1-c1ccc(C(=O)NCC(C)(C)C)cn1] | White solid, with a yield of 16.3% | 0.933 (s, 9H), 2.279 (d, 3H), 3.159 (d, 2H), 3.328-3.347 (m, 2H), 3.497-3.527 (m, 2H), 4.725 (t, 1H), 7.715-7.741 (m, 2H), 7.816 (s, 1H), 8.333 (dd, 1H), 8.581-8.624 (m, 2H), 9.100 (m, 1H). | 388.1 |
| 79 | I-79 | 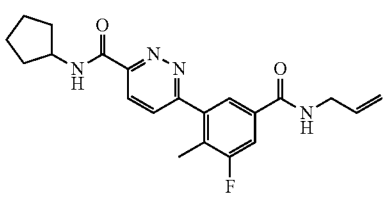 [SMILES: C=CCNC(=O)c1cc(F)c(C)c(-c2ccc(C(=O)NC3CCCC3)nn2)c1] | White solid, with a yield of 10.7% | 1.570-1.588 (m, 2H), 1.669-1.701 (m, 4H), 1.736-1.749 (m, 2H), 2.300 (d, 3H), 3.922-3.940 (m, 2H), 4.350-4.362 (m, 1H), 5.111 (dd, 1H), 5.196 (dd, 1H), 5.881-5.910 (m, 1H), 7.832 (d, 1H), 7.906 (s, 1H), 8.162 (d, 1H), 8.327 (d, 1H), 8.834-8.852 (m, 1H), 9.167 (d, 1H). | 381.1 [M − H]⁻ |
| 80 | I-80 | 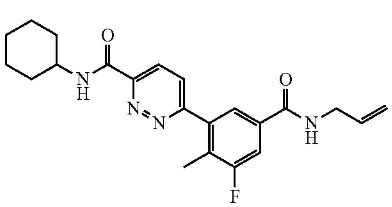 [SMILES: C=CCNC(=O)c1cc(F)c(C)c(-c2ccc(C(=O)NC3CCCCC3)nn2)c1] | White solid, with a yield of 10.6% | 1.171 (m, 1H), 1.337-1.359 (m, 2H), 1.494-1.518 (m, 2H), 1.611-1.632 (m, 1H), 1.750-1.773 (m, 2H), 1.837-1.853 (m, 2H), 2.300 (d, 3H), 3.921-3.939 (m, 3H), 5.111 (dd, 1H), 5.196 (dd, 1H), 5.881-5.910 (m, 1H), 7.832 (dd, 1H), 7.905 (d, 1H), 8.161 (d, 1H), 8.332 (d, 1H), 8.842-8.851 (m, 1H), 9.076 (d, 1H). | 395.1 [M − H]⁻ |

| Example | Compound | Structure | Result | $^1$HNMR (600 MHz, DMSO-d$_6$) δ* | MS [M + H]$^{+\#}$ |
|---|---|---|---|---|---|
| 81 | I-81 | 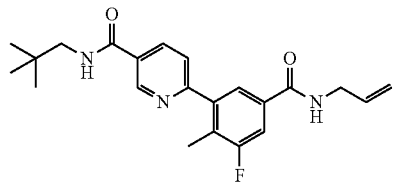 [SMILES: C=CCNC(=O)c1cc(F)c(C)c(-c2ccc(C(=O)NCC(C)(C)C)cn2)c1] | White solid, with a yield of 16.3% | CD$_3$OD: 1.031 (s, 9H), 2.315 (d, 3H), 3.328-3.338 (m, 2H), 4.013-4.028 (m, 2H), 5.153-5.175 (m, 1H), 5.256 (dd, 1H), 5.932-5.978 (m, 1H), 7.768-7.727 (m, 2H), 7.780 (d, 1H), 8.362 (dd, 1H), 9.095 (m, 1H). | 384.7 |

Note:
*represents that the used solvent was DMSO-d6 unless otherwise specified.

# represents [M+H]$^+$ unless otherwise specified.

Comparative Example

Preparation of 6-(5-(cyclopropylcarbamoyl)-3-fluoro-2-methylphenyl)-N-neopentylnicotinamide

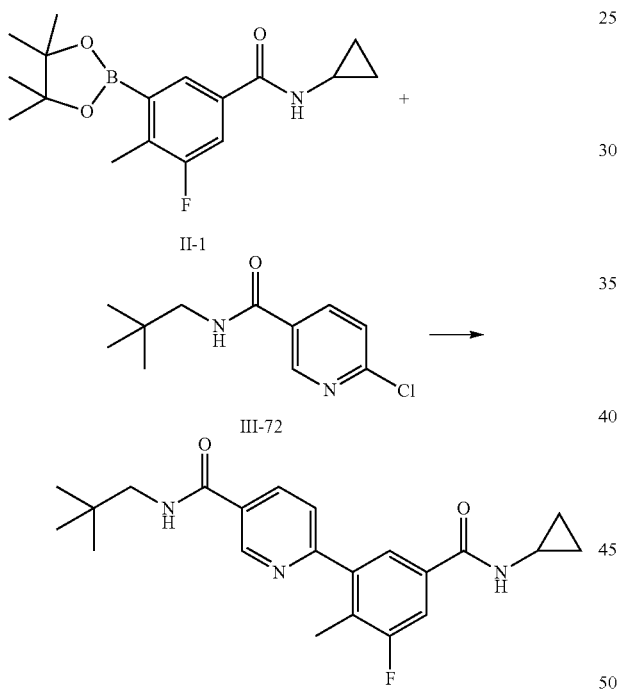

Compound III-72 (0.34 g, 1.5 mmol) and compound II (0.479 g, 1.5 mmol) were added in isopropyl alcohol (30 mL), 1M aqueous sodium bicarbonate (1.9 mL) and Pd(PPh$_3$)$_4$ (19 mg, 0.016 mmol) were added and refluxed at 90° C. for 10 hours. After completion of the reaction, the reaction solution was concentrated under reduced pressure. The residue was purified by column chromatography (petroleum ether:ethyl acetate=5:1) to give the target compound as a white solid (115 mg, 20%).

LC-MS (m/z): 384.2 [M+H]$^+$ $^1$HNMR (600 MHz, DMSO-d$_6$) δ: 0.582-0.587 (m, 2H), 0.683-0.715 (m, 2H), 0.933 (s, 9H), 2.258 (d, 3H), 2.822-2.905 (m, 1H), 3.164 (d, 2H), 7.733-7.681 (m, 2H), 7.762 (s, 1H), 8.335 (dd, 1H), 8.566 (d, 1H), 8.632 (t, 1H), 9.113 (d, 1H).

The invention claimed is:

1. A compound of formula I, or a tautomer, an optical isomer or a pharmaceutically acceptable salt thereof:

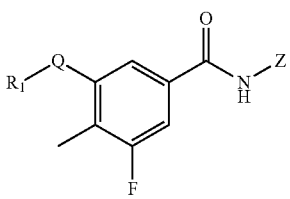

I wherein:
Q is selected from the group consisting of

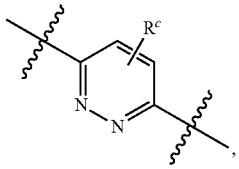

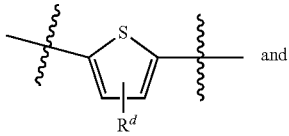 and

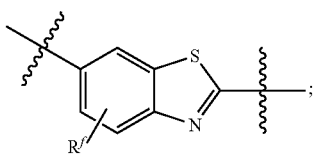;

R$^{c-f}$ is independently selected from the group consisting of H, halogen, hydroxyl, amino, C$_{1-6}$alkyl and C$_{1-6}$alkoxy, wherein the alkyl and the alkoxy may be optionally substituted by one or more substituents selected from the group consisting of halogen, hydroxyl and amino, the amino may be optionally substituted by one or two C$_{1-6}$alkyl;

$R_1$ is:

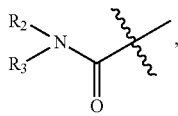
(1)

$R_2$ and $R_3$ are independently selected from the group consisting of H, $C_{1-6}$ alkyl, $(CH_2)_{0-3}$-3~7-membered cycloalkyl and heterocycloalkyl containing 1 or 2 heteroatoms, and $R_2$ and $R_3$ are not hydrogen at the same time; wherein the $C_{1-6}$alkyl may be optionally substituted by one or more substituents selected from the group consisting of halogen, hydroxyl, amino, cyano, $C_{1-6}$alkoxy, $(C_{0-6}$ alkyl) $(C_{0-6}$ alkyl) amino, $(C_{0-6}$ alkyl) thio, $(C_{1-6}$ alkyl)carbonyl and $(C_{1-6}$ alkyl) sulfonyl; the 3~7-membered cycloalkyl or heterocycloalkyl is substituted by one $R'''$, wherein the $R'''$ is selected from the group consisting of hydrogen, $C_{1-6}$alkyl, hydroxyl, halogen and amino, the heteroatom of the heterocycloalkyl is selected from O, N and S; or $R_2$ and $R_3$, together with the atoms attached thereto, form a 5, 6 or 7-membered ring, wherein, the 5, 6 or 7-membered ring is substituted by one $R''$, wherein the $R''$ is selected from hydrogen, $C_{1-6}$alkyl, hydroxyl, halogen and amino;

the 5, 6 or 7-membered ring, in addition to the N atom attaching to $R_2$ and $R_3$, further contains 0, 1 or 2 heteroatoms selected from O, N, and S; or

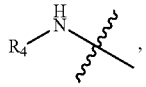
(2)

$R_4$ is selected from the group consisting of $C_{1-6}$alkyl, —$(CH_2)_{0-1}$-5~7-membered cycloalkyl, —$CO(CH_2)_{0-1}$—$R_5$ and —$CONH$—$R_6$, $R_5$ and $R_6$ are independently selected from $C_{1-6}$alkyl and $(CH_2)_{0-1}$-5~7-membered cycloalkyl;

Z is $(CH_2)_{0-3}$—Y; Y is selected from the group consisting of 3~7-membered cycloalkyl, heterocycloalkyl containing 1 or 2 heteroatoms, hydroxyl, $C_{1-6}$alkoxy, halogen, amino, cyano, nitro, alkenyl and alkynyl; wherein, the cycloalkyl, heterocycloalkyl, amino, alkenyl and alkynyl are optionally substituted by the substituents selected from the group consisting of $C_{1-6}$alkyl, $C_{1-6}$alkoxy, halogen, hydroxyl, amino, cyano and nitro; the heteroatom of the heterocycloalkyl is selected from N, S and O.

2. The compound of formula I, or the tautomer, the optical isomer or the pharmaceutically acceptable salt thereof according to claim 1, characterized in that:

Z is selected from the group consisting of:

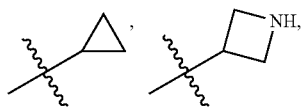

-continued

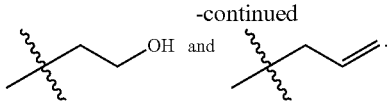

3. The compound of formula I, or the tautomer, the optical isomer or the pharmaceutically acceptable salt thereof according to claim 1, characterized in that:

Z is selected from the group consisting of:

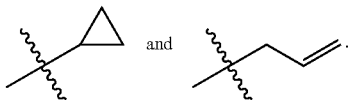

4. The compound of formula I, or the tautomer, the optical isomer or the pharmaceutically acceptable salt thereof according to claim 1, characterized in that:

Z is:

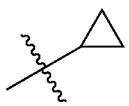

5. A compound of formula I, or a tautomer, an optical isomer or a pharmaceutically acceptable salt thereof:

wherein:

Q is selected from the group consisting of:

-continued

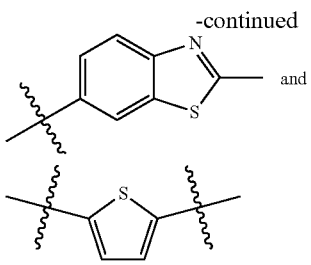
and $R_1$ is:

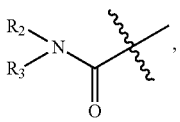  (1)

$R_2$ and $R_3$ are independently selected from the group consisting of H, $C_{1-6}$alkyl, $(CH_2)_{0-3}$-3~7-membered cycloalkyl and heterocycloalkyl containing 1 or 2 heteroatoms, and $R_2$ and $R_3$ are not hydrogen at the same time; wherein the $C_{1-6}$alkyl may be optionally substituted by one or more substituents selected from the group consisting of halogen, hydroxyl, amino, cyano, $C_{1-6}$alkoxy, $(C_{0-6}$ alkyl) $(C_{0-6}$ alkyl) amino, $(C_{0-6}$ alkyl) thio, $(C_{1-6}$ alkyl)carbonyl and $(C_{1-6}$ alkyl) sulfonyl; the 3~7-membered cycloalkyl or heterocycloalkyl is substituted by one $R'''$, wherein the $R'''$ is selected from the group consisting of hydrogen, $C_{1-6}$alkyl, hydroxyl, halogen and amino, the heteroatom of the heterocycloalkyl is selected from O, N and S; or $R_2$ and $R_3$, together with the atoms attached thereto, form a 5, 6 or 7-membered ring, wherein, the 5, 6 or 7-membered ring is substituted by one $R''$, wherein the $R''$ is selected from hydrogen, $C_{1-6}$alkyl, hydroxyl, halogen and amino;

the 5, 6 or 7-membered ring, in addition to the N atom attaching to $R_2$ and $R_3$, further contains 0, 1 or 2 heteroatoms selected from O, N, and S;

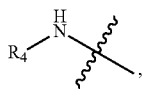  (2)

$R_4$ is selected from the group consisting of $C_{1-6}$alkyl, —$(CH_2)_{0-1}$-5~7-membered cycloalkyl, —CO $(CH_2)_{0-1}$—$R_5$ and —CONH—$R_6$, $R_5$ and $R_6$ are independently selected from $C_{1-6}$alkyl and $(CH_2)_{0-1}$-5~7-membered cycloalkyl;

Z is $(CH_2)_{0-3}$—Y; Y is selected from the group consisting of 3~7-membered cycloalkyl, heterocycloalkyl containing 1 or 2 heteroatoms, hydroxyl, $C_{1-6}$alkoxy, halogen, amino, cyano, nitro, alkenyl and alkynyl; wherein, the cycloalkyl, heterocycloalkyl, amino, alkenyl and alkynyl are optionally substituted by the substituents selected from the group consisting of $C_{1-6}$alkyl, $C_{1-6}$alkoxy, halogen, hydroxyl, amino, cyano and nitro; the heteroatom of the heterocycloalkyl is selected from N, S and O.

6. The compound of formula I, or the tautomer, the optical isomer or the pharmaceutically acceptable salt thereof according to claim 5, characterized in that:

Q is selected from the group consisting of:

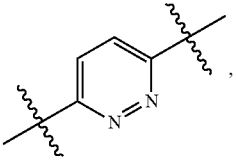,

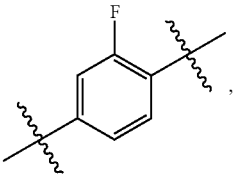, 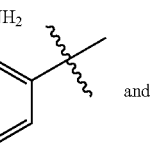 and

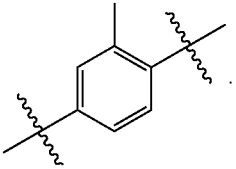.

7. The compound of formula I, or the tautomer, the optical isomer or the pharmaceutically acceptable salt thereof according to claim 5, characterized in that:

Q is selected from:

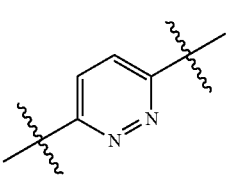 and 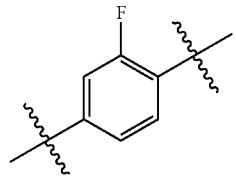.

8. The compound of formula I, or the tautomer, the optical isomer or the pharmaceutically acceptable salt thereof according to claim 1, characterized in that:

$R_1$ is:

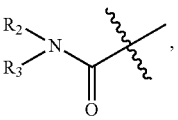, $R_2$ and $R_3$ are independently selected from the group consisting of H, $C_{1-6}$alkyl, $(CH_2)_{0-3}$-3~7-membered cycloalkyl and heterocycloalkyl containing 1 or 2 heteroatoms, and the $R_2$ and $R_3$ are not hydrogen at the same time; wherein the $C_{1-6}$alkyl may be substituted by one or more substituents selected from the group consisting of halogen, hydroxyl, amino, cyano, $C_{1-6}$alkoxy, $(C_{0-6}$ alkyl) $(C_{0-6}$ alkyl) amino, $(C_{0-6}$ alkyl) thio, $(C_{1-6}$ alkyl)carbonyl and $(C_{1-6}$ alkyl) sulfonyl; the 3~7-membered cycloalkyl or heterocycloalkyl is substituted by one $R'''$, wherein the $R'''$ is selected from the group consisting of hydrogen, $C_{1-6}$alkyl, hydroxyl, halogen and amino, the heteroatom of the heterocycloalkyl is selected from O, N, and S; or R$_2$ and R$_3$, together with the atoms attached thereto, form a 5, 6 or 7-membered ring, wherein, the 5-, 6- or 7-membered ring is substituted by one R", wherein the R" is selected from hydrogen, C$_{1-6}$alkyl, hydroxyl, halogen and amino;

the 5, 6 or 7-membered ring, in addition to the N atom attaching to R$_2$ and R$_3$, further contain 0, 1 or 2 heteroatoms selected from O, N, and S.

9. The compound of formula I, or the tautomer, the optical isomer or the pharmaceutically acceptable salt thereof according to claim 1, characterized in that:

R$_1$ is:

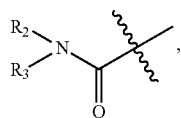

R$_2$ and R$_3$ are independently selected from the group consisting of H, C$_{1-6}$alkyl, (CH$_2$)$_{0-3}$-3~7-membered cycloalkyl, and R$_2$ and R$_3$ are not hydrogen at the same time; wherein the C$_{1-6}$alkyl may be substituted by one or more substituents selected from the group consisting of halogen, hydroxyl, amino, cyano, C$_{1-6}$alkoxy, (C$_{0-6}$ alkyl) (C$_{0-6}$ alkyl) amino, (C$_{0-6}$ alkyl) thio, (C$_{1-6}$ alkyl) carbonyl and (C$_{1-6}$ alkyl) sulfonyl; the 3~7-membered cycloalkyl is substituted by one R'", wherein the R'" is selected from the group consisting of hydrogen, C$_{1-6}$alkyl, hydroxyl, halogen and amino; or R$_2$ and R$_3$, together with the atoms attached thereto, form a 5, 6 or 7-membered ring, wherein, the 5-, 6- or 7-membered ring is substituted by one R", wherein the R" is selected from hydrogen, C$_{1-6}$alkyl, hydroxyl, halogen and amino.

10. The compound of formula I, or the tautomer, the optical isomer or the pharmaceutically acceptable salt thereof according to claim 1, characterized in that:

R$_1$ is:

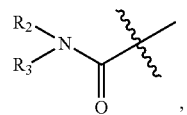

one of R$_2$ and R$_3$ is H, the other is selected from the group consisting of C$_{1-6}$alkyl, (CH$_2$)$_{0-3}$-3~7-membered cycloalkyl; wherein the C$_{1-6}$alkyl may be substituted by one or more substituents selected from the group consisting of halogen, hydroxyl, amino, cyano, C$_{1-6}$alkoxy, (C$_{0-6}$ alkyl) (C$_{0-6}$ alkyl) amino, (C$_{0-6}$ alkyl) thio, (C$_{1-6}$ alkyl)carbonyl and (C$_{1-6}$ alkyl) sulfonyl; the 3~7-membered cycloalkyl is substituted by one R'", wherein the R'" is selected from hydrogen, C$_{1-6}$alkyl, hydroxyl, halogen and amino.

11. The compound of formula I, or the tautomer, the optical isomer or the pharmaceutically acceptable salt thereof according to claim 1, characterized in that:

R$_1$ is selected from:

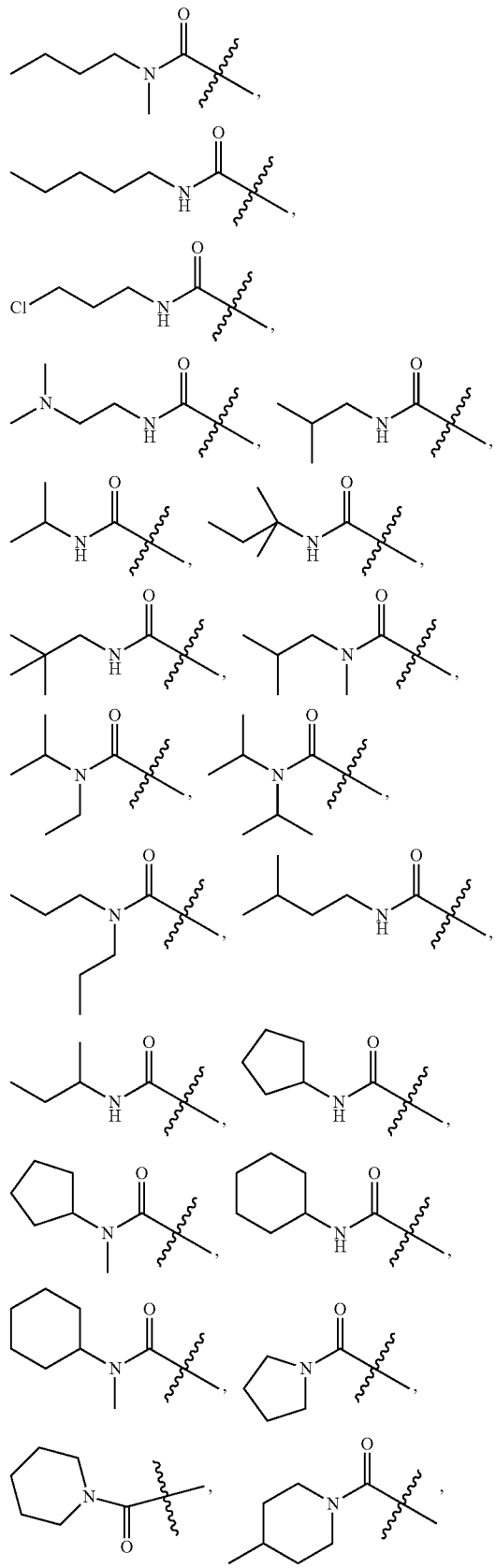

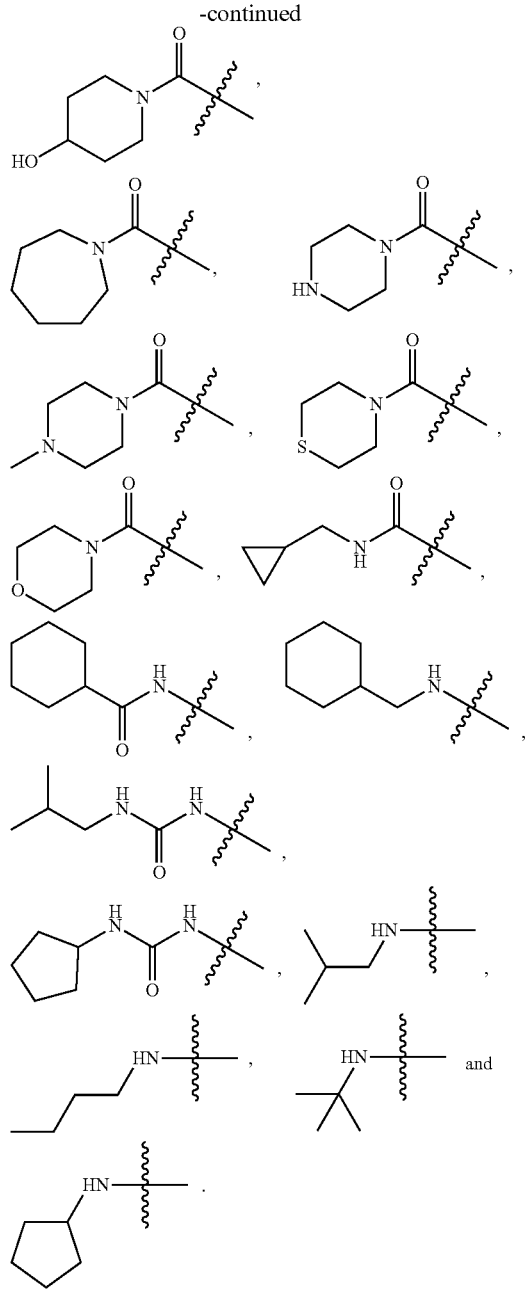
12. The compound of formula I, or the tautomer, the optical isomer or the pharmaceutically acceptable salt thereof according to claim 1, characterized in that:
R₁ is selected from:
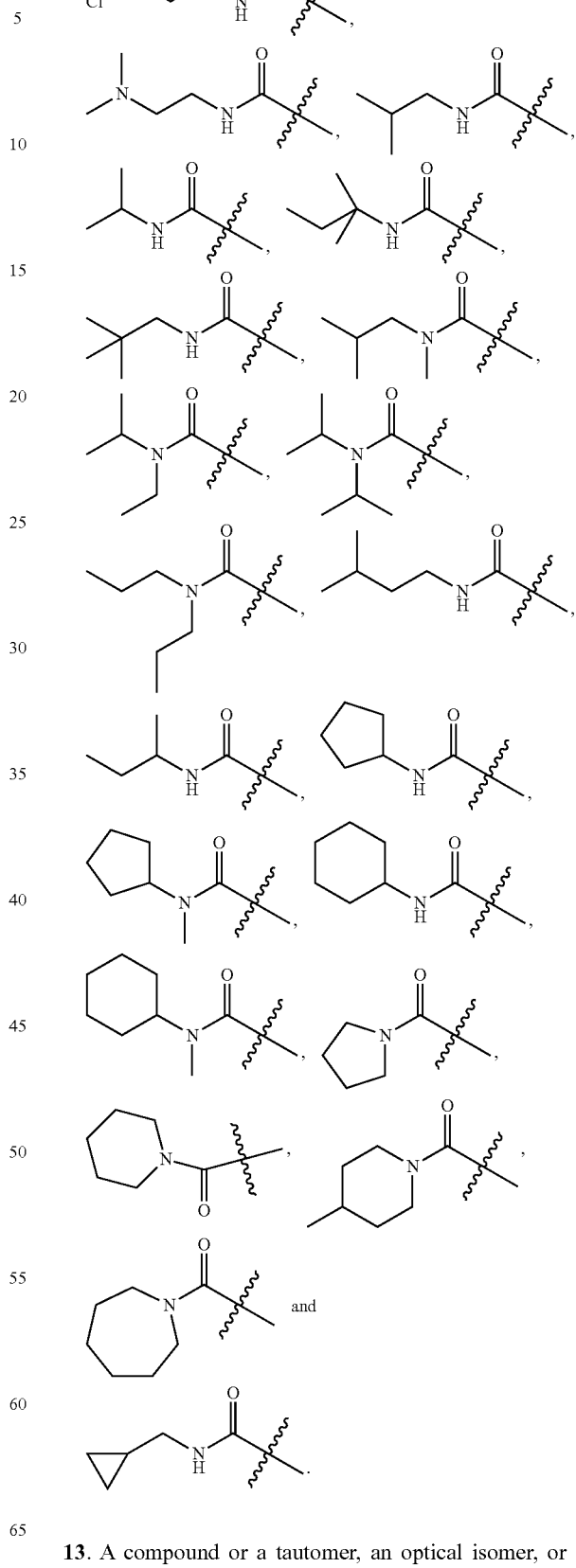
13. A compound or a tautomer, an optical isomer, or a pharmaceutically acceptable salt thereof, selected from:

109
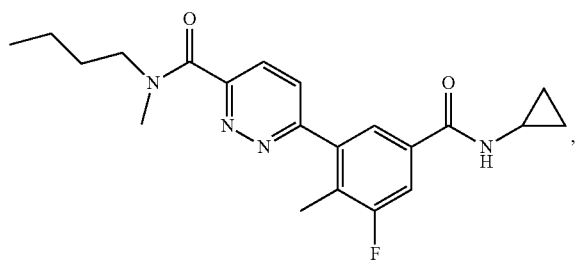
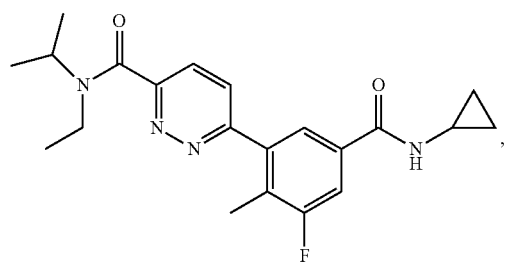
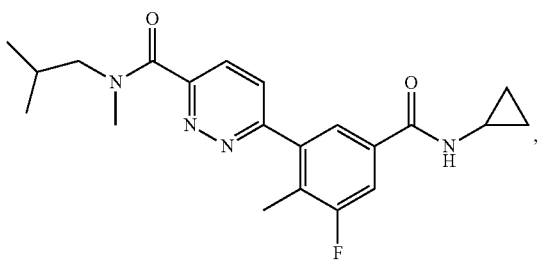
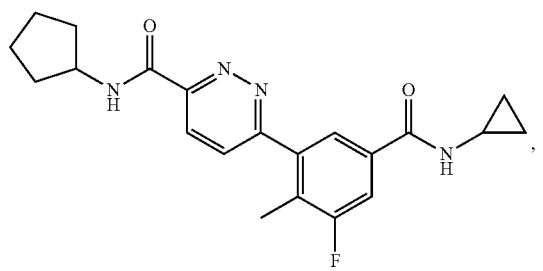
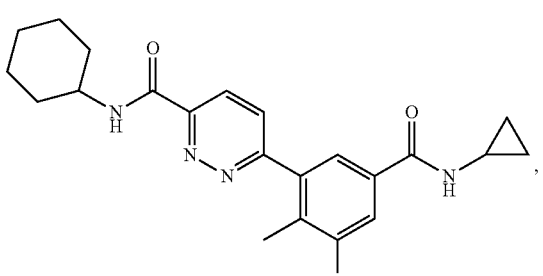
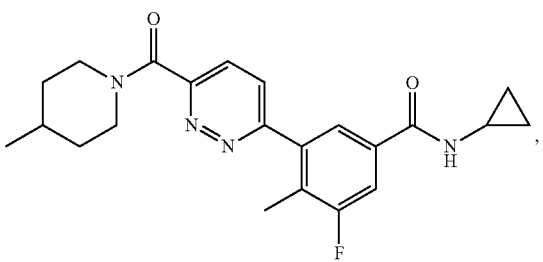
110
-continued
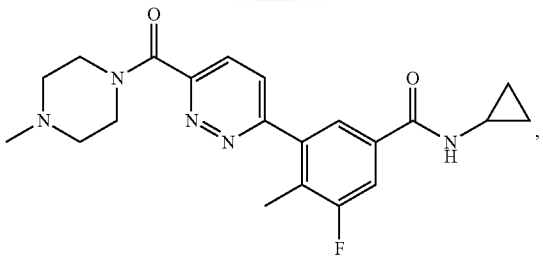
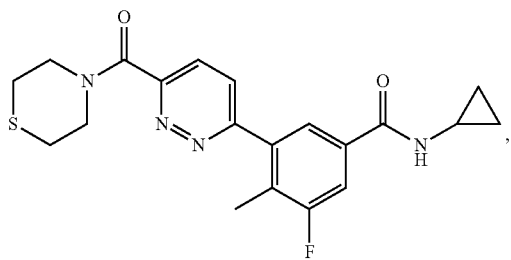
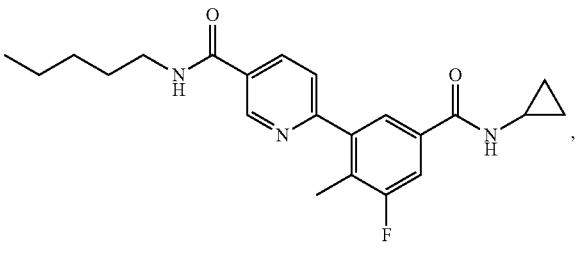
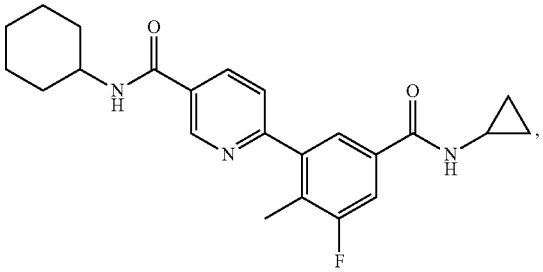
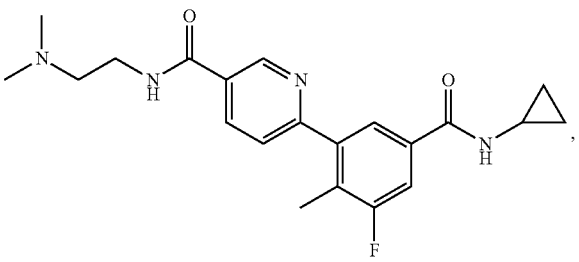
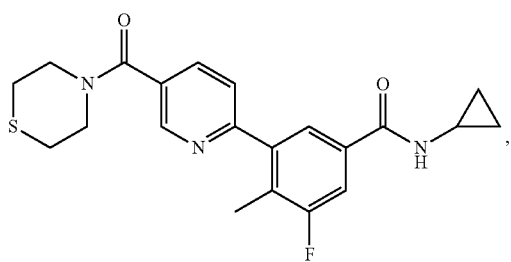

111
-continued
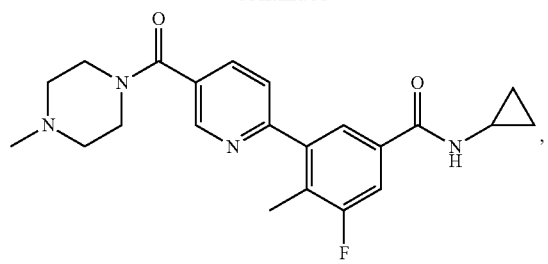
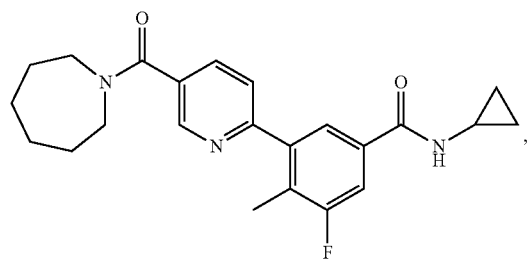
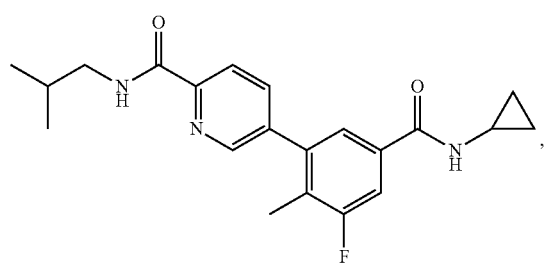
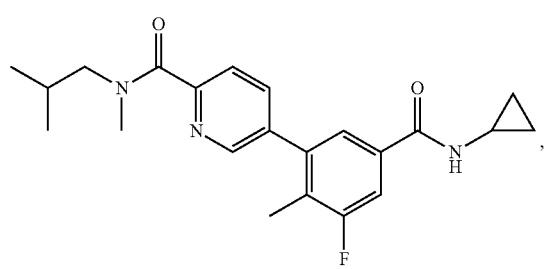
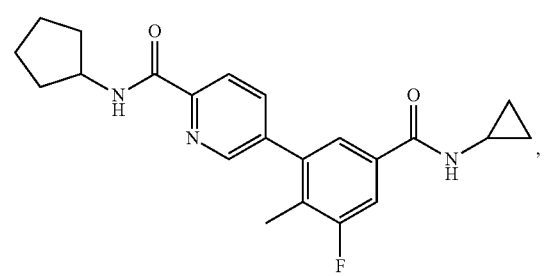
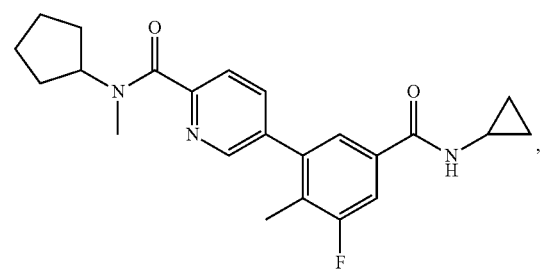
112
-continued
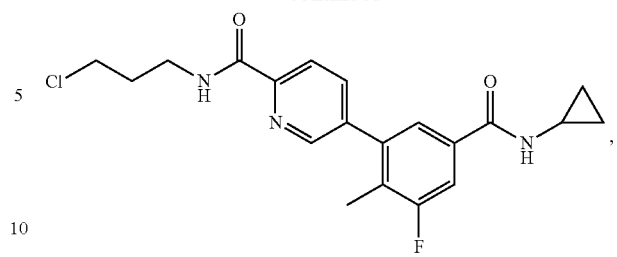
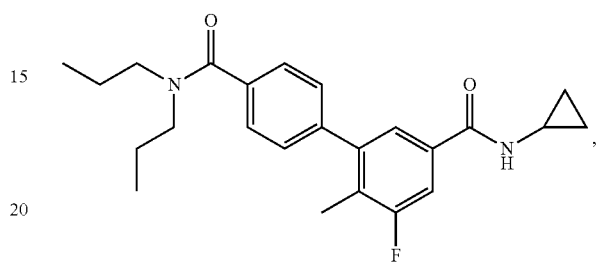
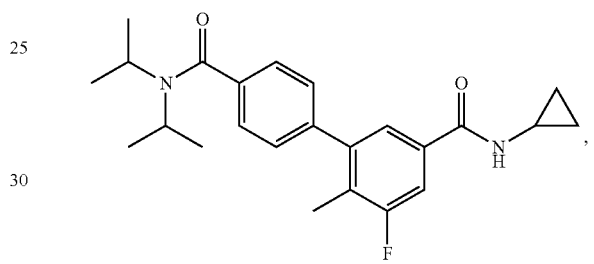
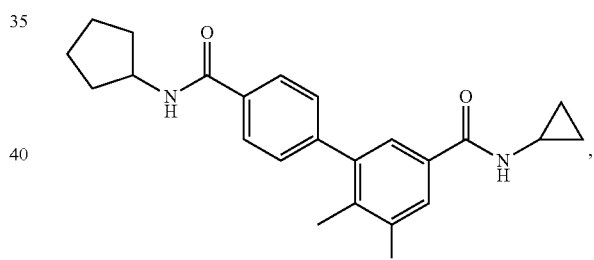
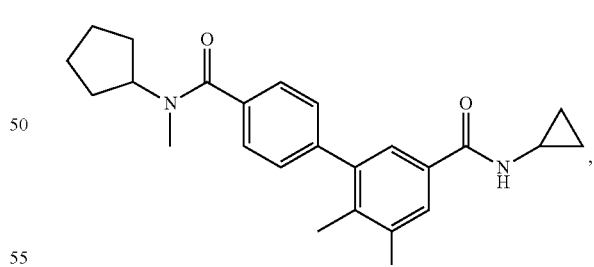
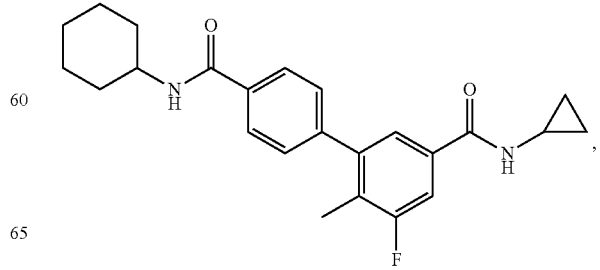

-continued

115
-continued
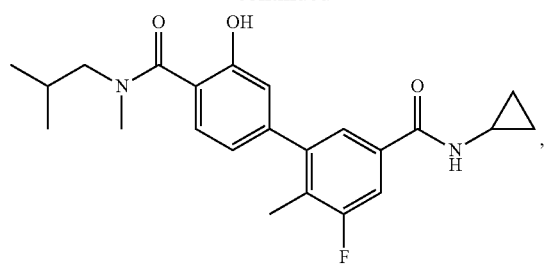
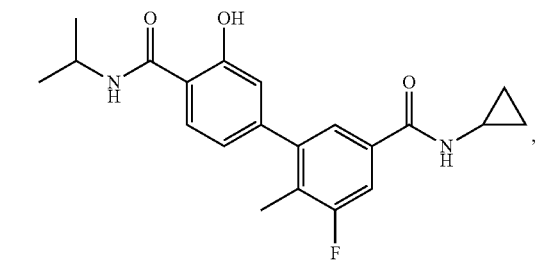
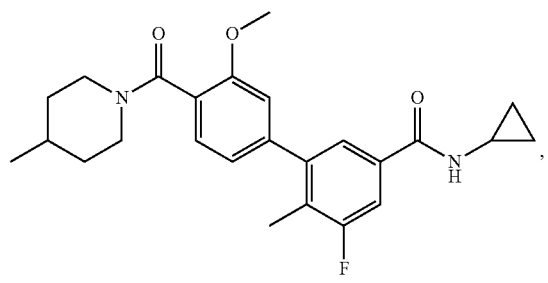
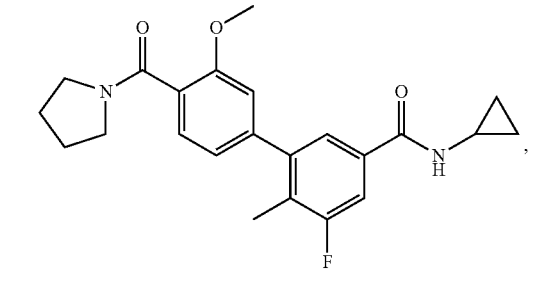
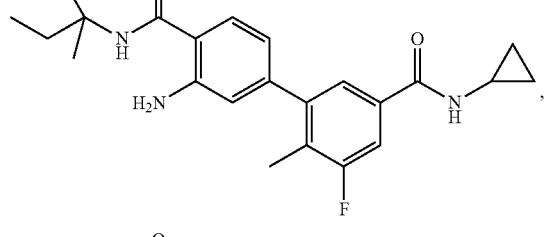
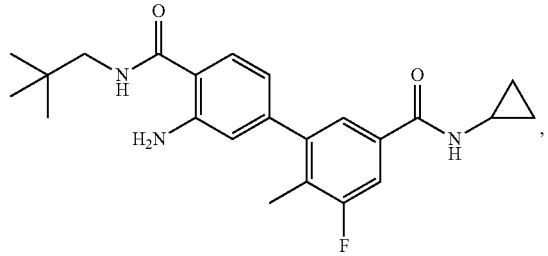
116
-continued
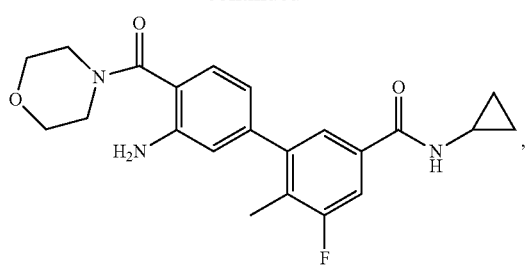
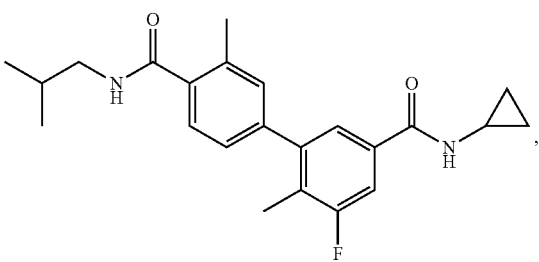
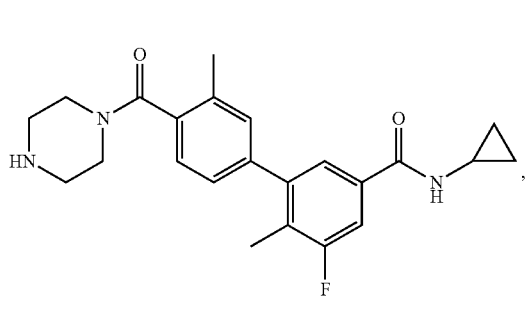
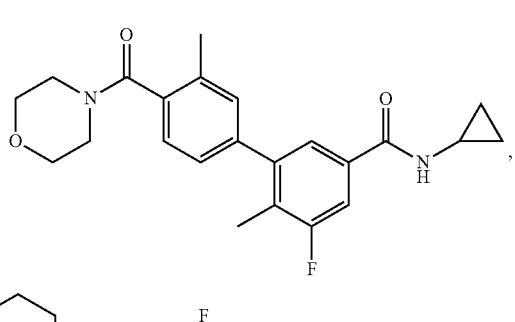
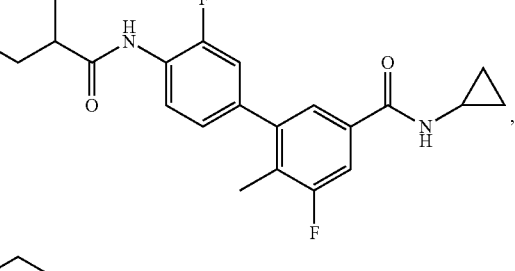
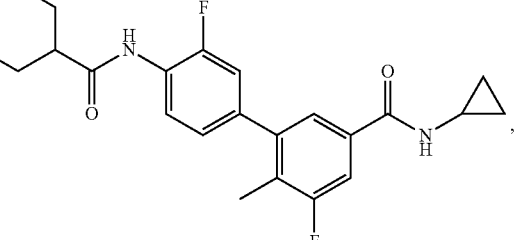

117
-continued
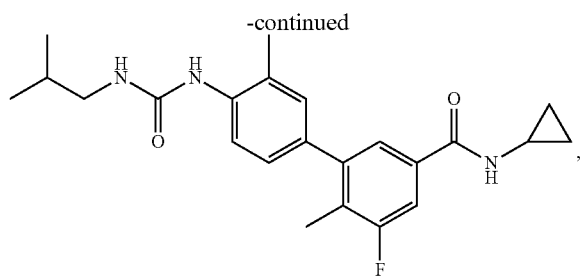,
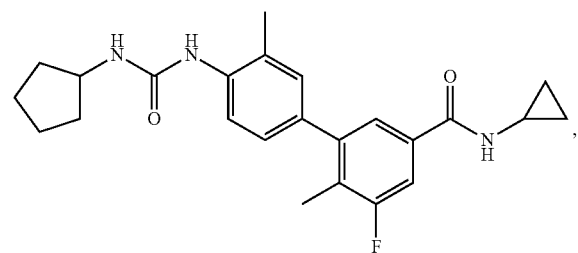,
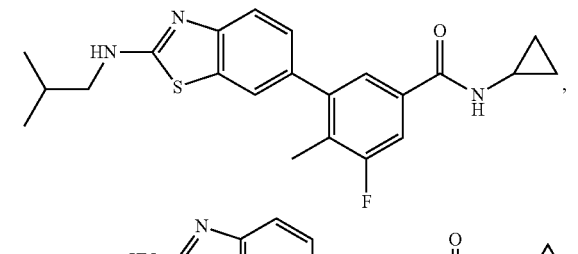,
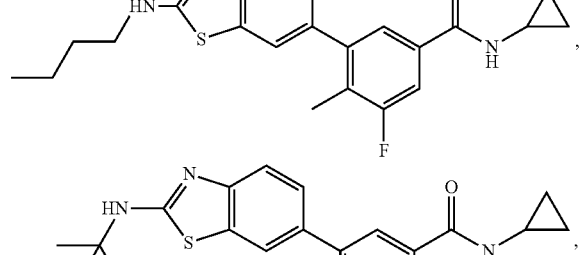,
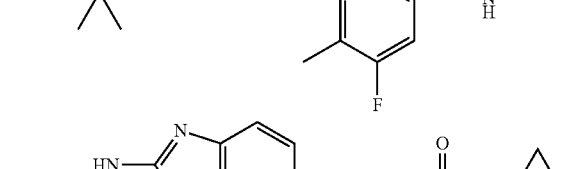,
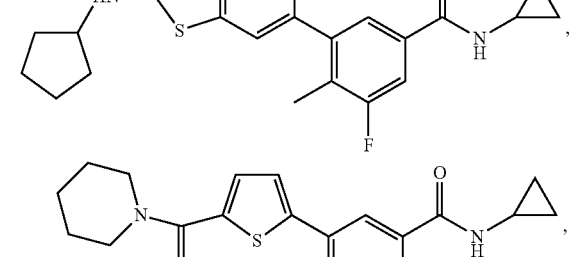,
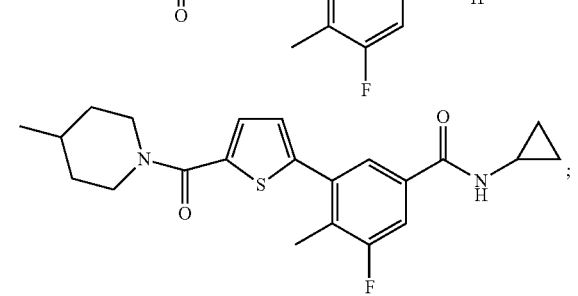;
118
-continued
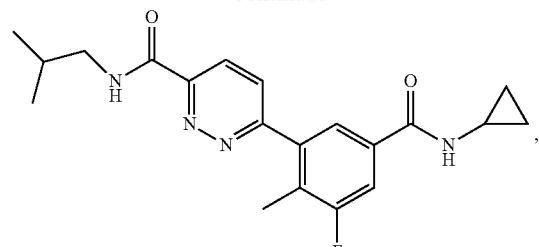,
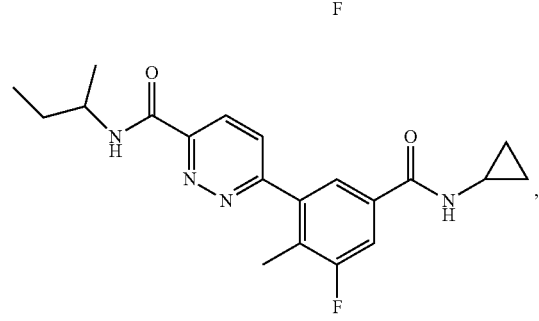,
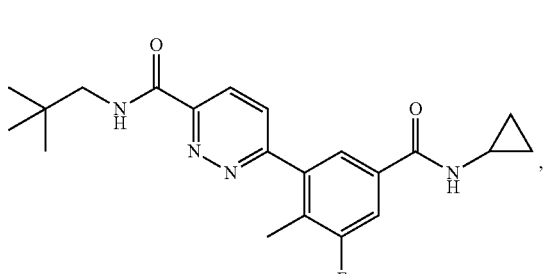,
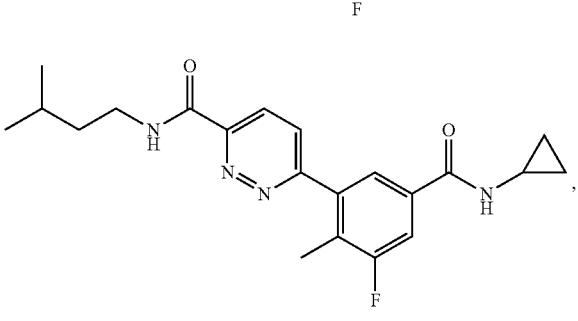,
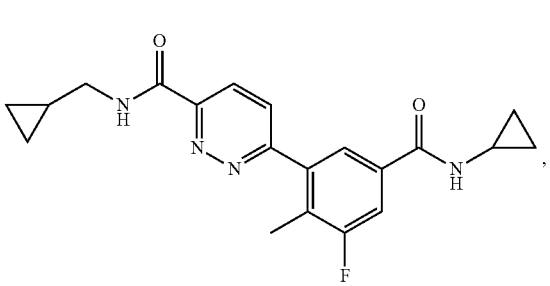,
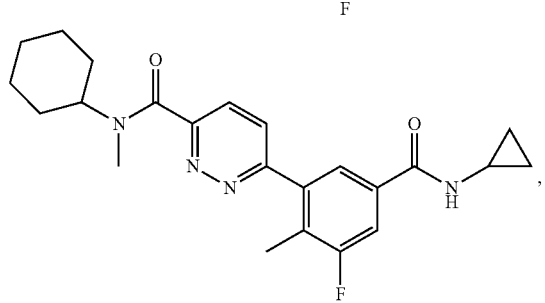, 119
-continued
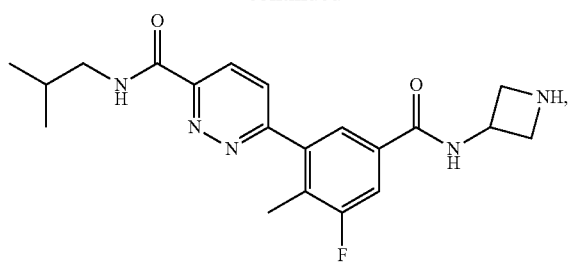
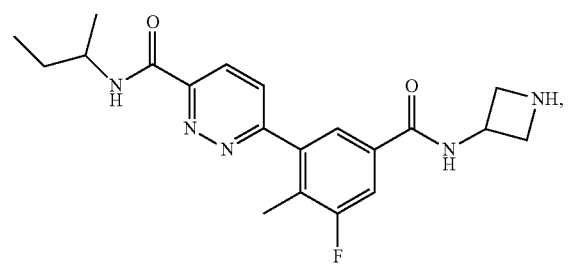
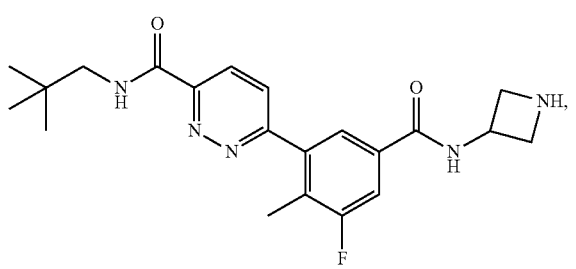
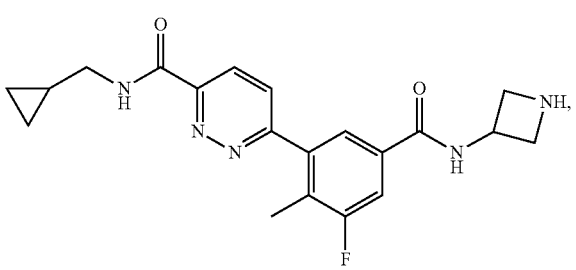
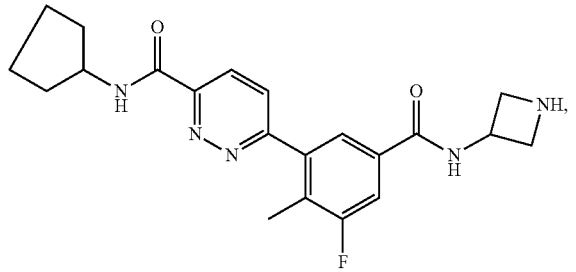
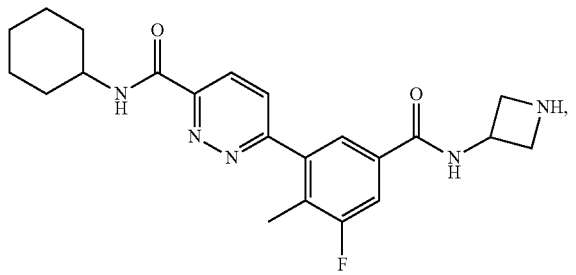
120
-continued
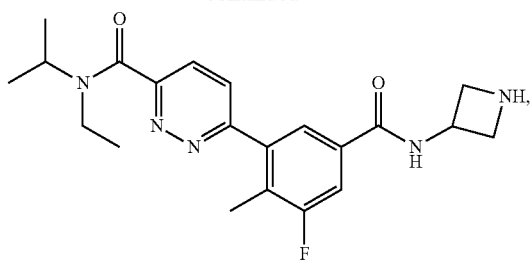
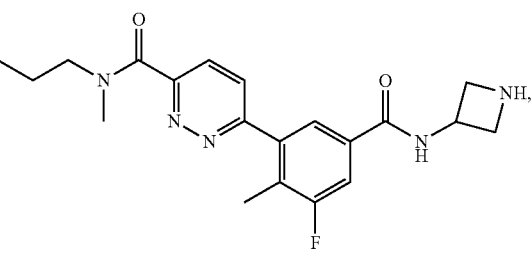
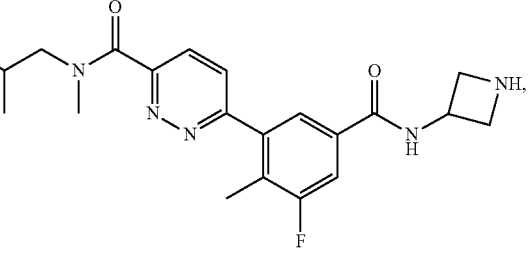
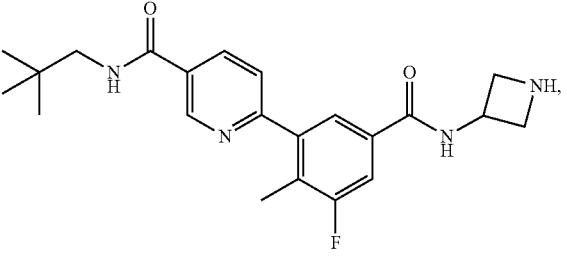
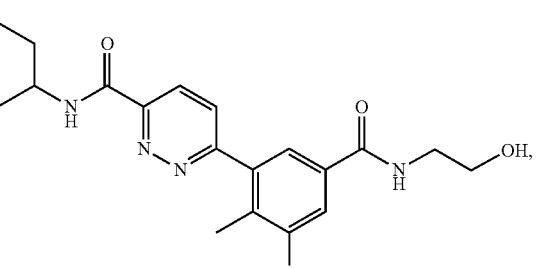
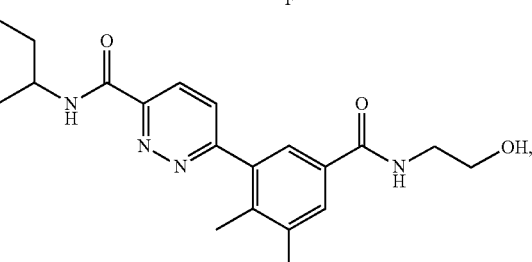

121
-continued

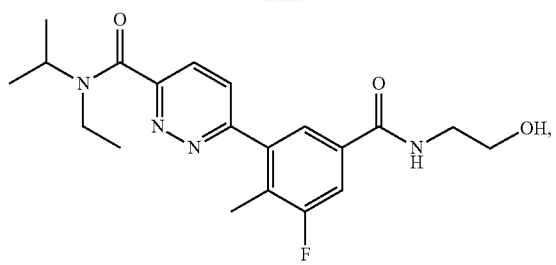

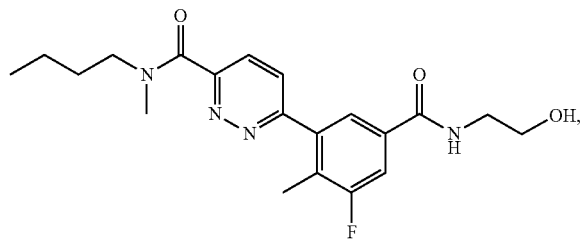

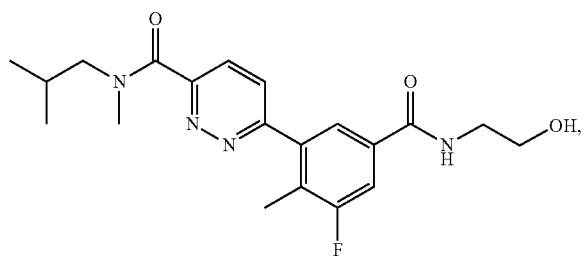

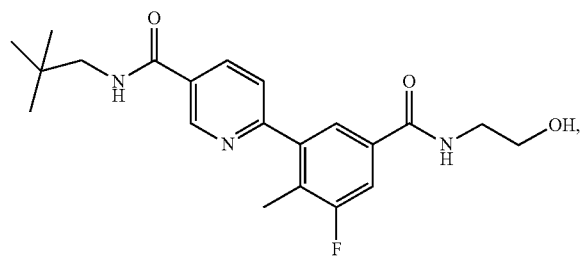

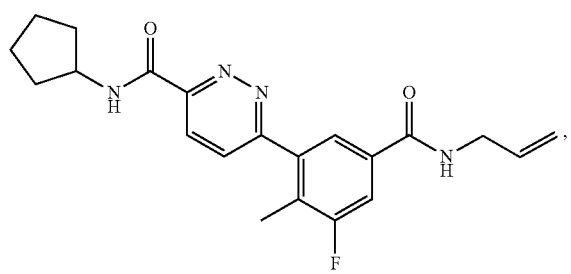

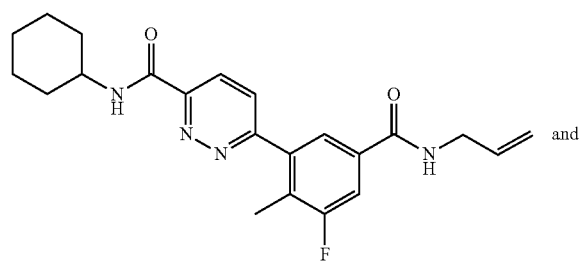 and

122
-continued

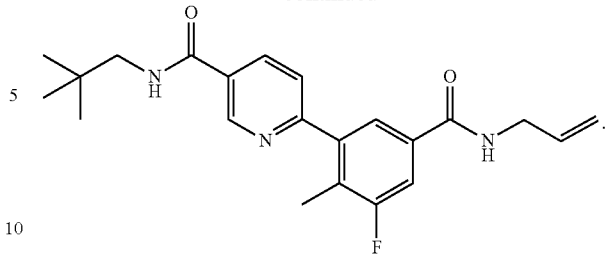

14. A pharmaceutical composition, comprising the compound of formula I, or the tautomer, the optical isomer or the pharmaceutically acceptable salt thereof according to claim 1.

15. A pharmaceutical composition, comprising the compound, or the tautomer, the optical isomer or the pharmaceutically acceptable salt thereof according to claim 13.

16. A method for treating symptoms or diseases mediated by p38 kinase activity or mediated by the cytokines produced by p38 kinase activity comprising administering to a subject a therapeutically effective amount of the compound of formula I, or the tautomer, the optical isomer or the pharmaceutically acceptable salt thereof according to claim 1.

17. A method for treating symptoms or diseases mediated by p38 kinase activity or mediated by the cytokines produced by p38 kinase activity comprising administering to a subject a therapeutically effective amount of the compound, or the tautomer, the optical isomer or the pharmaceutically acceptable salt thereof according to claim 13.

18. The method according to claim 16, wherein the disease is selected from inflammatory disease.

19. The method according to claim 17, wherein the disease is selected from inflammatory disease.

20. The method according to claim 16, wherein the disease is selected from rheumatoid arthritis, chronic lung obstruction, cardiovascular disease, gout, psoriasis, asthma, tumor, diabetes mellitus, arteriosclerosis and Crohn's disease.

21. The method according to claim 17, wherein the disease is selected from rheumatoid arthritis, chronic lung obstruction, cardiovascular disease, gout, psoriasis, asthma, tumor, diabetes mellitus, arteriosclerosis and Crohn's disease.

22. A method for preparing the compound of formula I, or the tautomer, the optical isomer or the pharmaceutically acceptable salt thereof according to claim 1, comprising condensing a compound of formula II and a compound of formula III to form the compound of formula I:

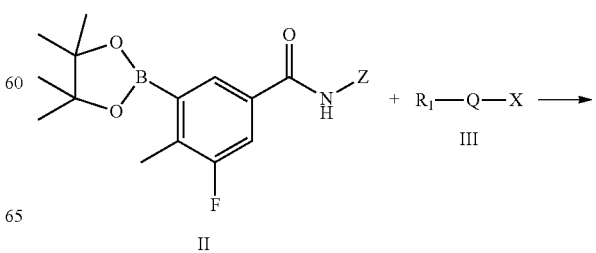

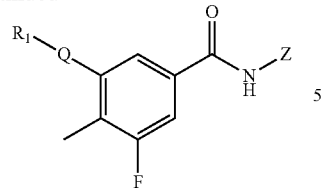
Q, Z and $R_1$ were defined as claim 1, X is halogen.
* * * * *